United States Patent
Liu

(10) Patent No.: US 11,447,563 B2
(45) Date of Patent: Sep. 20, 2022

(54) TUMOR SELECTIVE MACROPINOCYTOSIS-DEPENDENT RAPIDLY INTERNALIZING ANTIBODIES

(71) Applicant: The Regents of the University of California, Oakland, CA (US)

(72) Inventor: Bin Liu, San Francisco, CA (US)

(73) Assignee: The Regents of the University of California, Oakland, CA (US)

(*) Notice: Subject to any disclaimer, the term of this patent is extended or adjusted under 35 U.S.C. 154(b) by 0 days.

(21) Appl. No.: 16/714,566

(22) Filed: Dec. 13, 2019

(65) Prior Publication Data
US 2020/0216556 A1 Jul. 9, 2020

Related U.S. Application Data

(62) Division of application No. 15/321,684, filed as application No. PCT/US2015/039741 on Jul. 9, 2015, now Pat. No. 10,550,195.

(60) Provisional application No. 62/023,689, filed on Jul. 11, 2014.

(51) Int. Cl.

| | | |
|---|---|---|
| C40B 40/10 | (2006.01) | |
| C07K 16/30 | (2006.01) | |
| G01N 33/574 | (2006.01) | |
| C12N 15/10 | (2006.01) | |
| G01N 33/68 | (2006.01) | |
| A61K 47/68 | (2017.01) | |
| C07K 16/28 | (2006.01) | |
| A61K 45/06 | (2006.01) | |

(Continued)

(52) U.S. Cl.
CPC .............. *C07K 16/30* (2013.01); *A61K 45/06* (2013.01); *A61K 47/6801* (2017.08); *A61K 47/6851* (2017.08); *A61K 47/6889* (2017.08); *A61K 49/00* (2013.01); *C07K 16/005* (2013.01); *C07K 16/2866* (2013.01); *C07K 16/3069* (2013.01); *C12N 15/1037* (2013.01); *G01N 33/574* (2013.01); *G01N 33/6854* (2013.01); *C07K 2317/10* (2013.01); *C07K 2317/21* (2013.01); *C07K 2317/32* (2013.01); *C07K 2317/622* (2013.01); *C07K 2317/73* (2013.01); *C07K 2317/77* (2013.01); *C40B 40/10* (2013.01)

(58) Field of Classification Search
None
See application file for complete search history.

(56) References Cited

U.S. PATENT DOCUMENTS

| 10,550,195 B2 | 2/2020 | Liu |
| 2013/0065227 A1 | 3/2013 | Bates et al. |
| 2017/0137532 A1 | 5/2017 | Liu |

FOREIGN PATENT DOCUMENTS

| WO | WO 98/22149 A1 | 5/1998 |
| WO | WO 2007/030642 A2 | 3/2007 |

(Continued)

OTHER PUBLICATIONS

AU Office Action dated Mar. 20, 2020 issued in AU 2015287749.
(Continued)

*Primary Examiner* — Christian C Boesen
(74) *Attorney, Agent, or Firm* — Tom Hunter; Weaver Austin Villeneuve & Sampson LLP

(57) ABSTRACT

Methods are provided for identifying and selecting antibodies that are internalized into cells via the macropinocytosis pathway. Additionally antibodies that are internalized via this pathway are provided as well as immunoconjugates comprising such antibodies.

19 Claims, 29 Drawing Sheets

Specification includes a Sequence Listing.

(51) Int. Cl.
*A61K 49/00* (2006.01)
*C07K 16/00* (2006.01)

(56) References Cited

FOREIGN PATENT DOCUMENTS

WO WO 2012/012759 A2 1/2012
WO WO 2013/109580 A1 7/2013

OTHER PUBLICATIONS

EP Extended Search Report dated Jan. 2, 2018 issued in EP 15818722.9.
European Office Action dated Dec. 20, 2018 issued in EP 15818722.9.
PCT International Search Report and Written Opinion dated Sep. 21, 2015 issued in PCT/US2015/039741.
PCT International Preliminary Report on Patentability and Written Opinion dated Jan. 26, 2017 issued in PCT/US2015/039741.
U.S. Office Action [Restriction Requirement] dated Jan. 15, 2019 issued in U.S. Appl. No. 15/321,684.
U.S. Office Action dated Apr. 5, 2019 issued in U.S. Appl. No. 15/321,684.
U.S. Notice of Allowance dated Sep. 18, 2019 issued in U.S. Appl. No. 15/321,684.
Chakraborty et al. (2012) "Kaposi's sarcoma-associated herpesvirus interacts with EphrinA2 receptor to amplify signaling essential for productive infection" *PNAS* 109(19): E1163-E1172.
Ha et al. (2014) "High-content Analysis of Antibody Phage-display Library Selection Outputs Identifies Tumor Selective Macropinocytosis-dependent Rapidly Internalizing Antibodies" *Mo. Cell. Proteom.* 13(12):3320-3331.
Ha et al. (2016) "Macropinocytosis Exploitation by Cancers and Cancer Therapeutics" *Frontiers in Physiology* 7(381):1-10.
Hewlett et al. (1994) "The coated pit and macropinocytic pathways serve distinct endosome populations" *J. Cell Biol.* 124: 689-703.
Jackson et al. (2008) "A Human Antibody-Drug Conjugate Targeting EphA2 Inhibits Tumor Growth In vivo" *Cancer Res.* 68: 9367-9374.
Johns et al. (2002) "Novel monoclonal antibody specific for the de2-7 epidermal growth factor receptor (EGFR) that also recognizes the EGFR expressed in cells containing amplification of the EGFR" *International Journal of Cancer* 98: 398-408.
Kubo et al. (2008) "Identification of oligopeptide binding to colon cancer cells separated from patients using laser capture microdissection" *Journal of Drug Targeting* 16(5): 396-404.

Liu et al. (2004) "Mapping Tumor Epitope Space by Direct Selection of Single-Chain Fv Antibody Libraries on Prostate Cancer Cells" *Cancer Res.* 64: 704-710.
Poul et al. (2000) "Selection of tumor-specific internalizing human antibodies from phage libraries" *J. Mol. Biol.* 301: 1149-1161.
Reyes-Reyes et al. (2010) "A New Paradigm for Aptamer Therapeutic AS1411 Action: Uptake by Macropinocytosis and Its Stimulation by a Nucleolin-Dependent Mechanism" *Cancer Res.* 70: 8617-8629.
Ritchie et al. (2013) "Implications of receptor-mediated endocytosis and intracellular trafficking dynamics in the development of antibody drug conjugates" *Landes Bioscience* 5(1): 13-21.
Ruan et al. (2006) "Identification of Clinically Significant Tumor Antigens by Selecting Phage Antibody Library on Tumor Cells in Situ Using Laser Capture Microdissection" *Mol. Cell Proteomics.* 5: 2364-2373.
Rudnick et al. (2011) "Influence of Affinity and Antigen Internalization on the Uptake and Penetration of Anti-HER2 Antibodies in Solid Tumors" *Cancer Res.* 71: 2250-2259.
Shen et al. (2013) "Enhancing Chemotherapy Response with Sustained EphA2 Silencing Using Multistage Vector Delivery" *Clin. Cancer Res.* 19: 1806-1815.
Sutherland et al. (2006) "Lysosomal Trafficking and Cysteine Protease Metabolism Confer Target-specific Cytotoxicity by Peptide-linked Anti-CD30-Auristatin Conjugates" *J. Biol. Chem.* 281: 10540-10547.
Tanaka et al. (2010) "Sustained Small Interfering RNA Delivery by Mesoporous Silicon Particles" *Cancer Res.* 70: 3687-3696.
Tandon et al. (2011) "Emerging strategies for EphA2 receptor targeting for cancer therapeutics." *Expert Opin. Ther. Targets.* 15: 31-51 [NIH Public Access—Author Manuscript—31 pages] doi:10.1517/14728222.2011.538682.
Veithen et al. (1996) "v-Src induces constitutive macropinocytosis in rat fibroblasts." *J. Cell Sci.* 109(Pt 8): 2005-2012.
Wang et al. (2014) "Macropinosome quantitation assay" *MethodsX* 1: 36-41.
West et al. (1989) "Distinct endocytotic pathways in epidermal growth factor-stimulated human carcinoma A431 cells." *J. Cell Biol.* 109: 2731-2739).
Wykosky and Debinski (2008) "The EphA2 Receptor and EphrinA1 Ligand in Solid Tumors: Function and Therapeutic Targeting" *Mol. Cancer Res.* 6: 1795-1806.
Zhou et al. (2010) "Internalizing cancer antibodies from phage libraries selected on tumor cells and yeast-displayed tumor antigens." *J. Mol. Biol.* 404: 88-99 [NIH Public Access—Author Manuscript—24 pages] doi:10.1016/j.jmb.2010.09.006.
Zhu et al. (2010) "Identification of Internalizing Human Single-Chain Antibodies Targeting Brain Tumor Sphere Cells" *Mol. Cancer Ther.* 9: 2131-2141.
CA Office Action dated Jul. 5, 2021 issued in CA 2,954,041.

HCA clones

Heavy chain

| Clone | Frame 1 | CDR1 | Frame 2 | CDR2 | Frame 3 | CDR3 | Frame 4 |
|---|---|---|---|---|---|---|---|
| HCA-F1 | QVQLQESGG GLVQPGGSL RLSCAASGF TFS | SYSMN | WVRQAPGKG LEWVS | YISSSSSTI YYADSVKG | RFTISRDNA KNSLYLQMN SLRAEDTAV YYCAR | YRLPDFWSG YPNYGMDV | WGQGTTVTV SS |
| HCA-F2 | QVQLVESGG GLVQPGGSL RLSCAASGF TFS | SYAMS | WVRQAPGKG LEWVS | AISGSGGST YYADSVKG | RFTISRDNS KNTLYLQMN SLRAEDTAV YYCAT | LSVEWYGSG SYLGY | WGQGTLVTV SS |
| HCA-M1 | QVQLVESGG GVVQPGRSL RLSCAASGF TFS | SYAMH | WVRQAPGKG LEWVA | VISYDGSNK YYADSVKG | RFTISRDNS KNTLYLQMN SLRAEDTAV YYCAR | APAYSYGPF DY | WGQGTLVTV SS |
| HCA-S1 | QVQLQESGG GLVQPGGSL RLSCAASGF TFS | SYAMH | WVRQAPGKG LEWVA | VISYDGSNK YYADSVKG | RFTISRDNS KNTLYLQMN SLRAEDTAV YYCAR | FSSGWYYFD Y | WGQGTLVTV SS |

Light chain

| Clone | Frame 1 | CDR1 | Frame 2 | CDR2 | Frame 3 | CDR3 | Frame 4 |
|---|---|---|---|---|---|---|---|
| HCA-F1 | QSVLTQPPS VSGAPGQRV TISC | TGSSSNIGA GYDVH | WYQQLPGTA PKLLI | YGNSNRPS | GVPDRFSGS KSGTSASLA ITGLQAEDE ADYYC | QSYDSSLSG HVV | FGGGTKLTV L |
| HCA-F2 | NFMLTQDPA VSVALGQTV RITC | QGDSLRSYY AS | WYQQKPGQA PVLVI | YGKNNRPS | GIPDRFSGS SSGNTASLT ITGAQAEDE AHYYC | NSRDSSANH VV | FGGGTKVTV L |
| HCA-M1 | SSELTQDPA VSVALGQTV RITC | QGDSLRSYY AS | WYQQKPGQA PVLVI | YGKNNRPS | GIPDRFSGS SSGNTASLT ITGAQAEDE ADYYC | HSRDSSGTH LRV | FGGGTKVTV L |
| HCA-S1 | DIQMTQSPS FLSASVGDR ITITC | RASHDISSY FA | WYQQKPGKA PKPLI | YAASTLQS | GVPSRFSGS GSGTEFTLT ISSLQPEDF ATYYC | QQLGSYPLT | FGGGTKLEI K |

Fig. 1

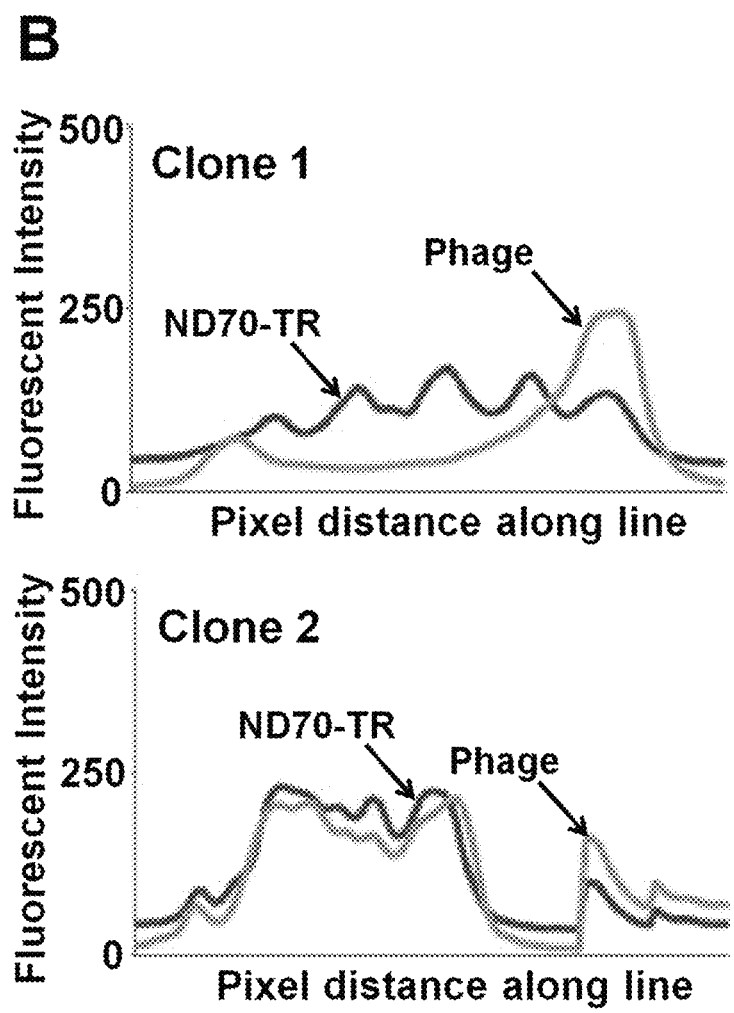
*Fig. 3, cont'd.*

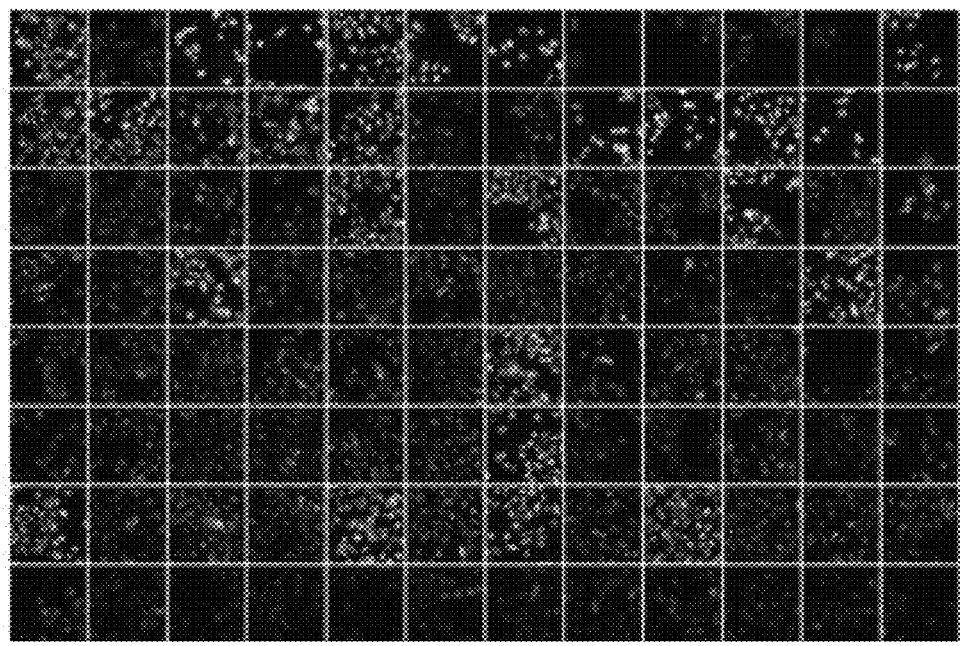
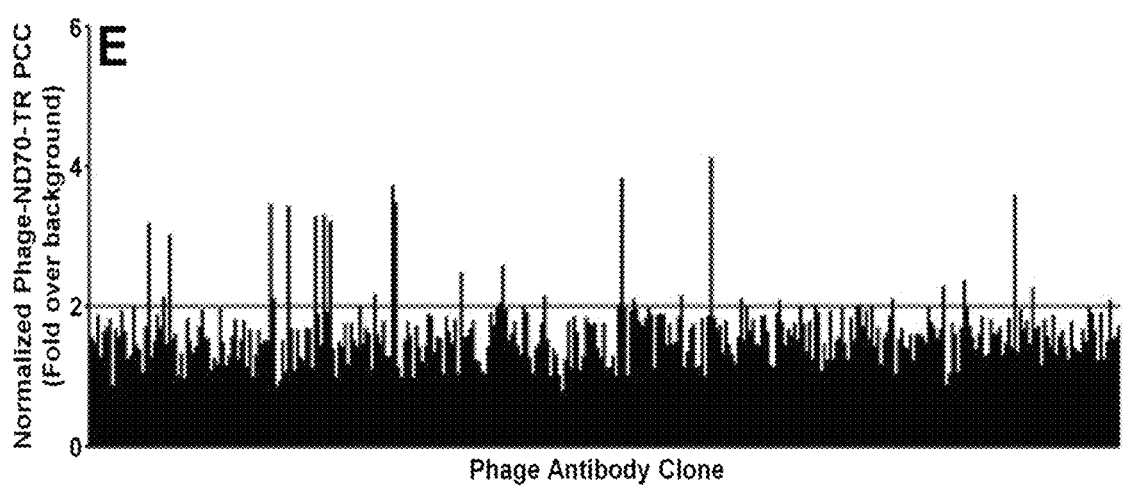
*Fig. 3, cont'd.*

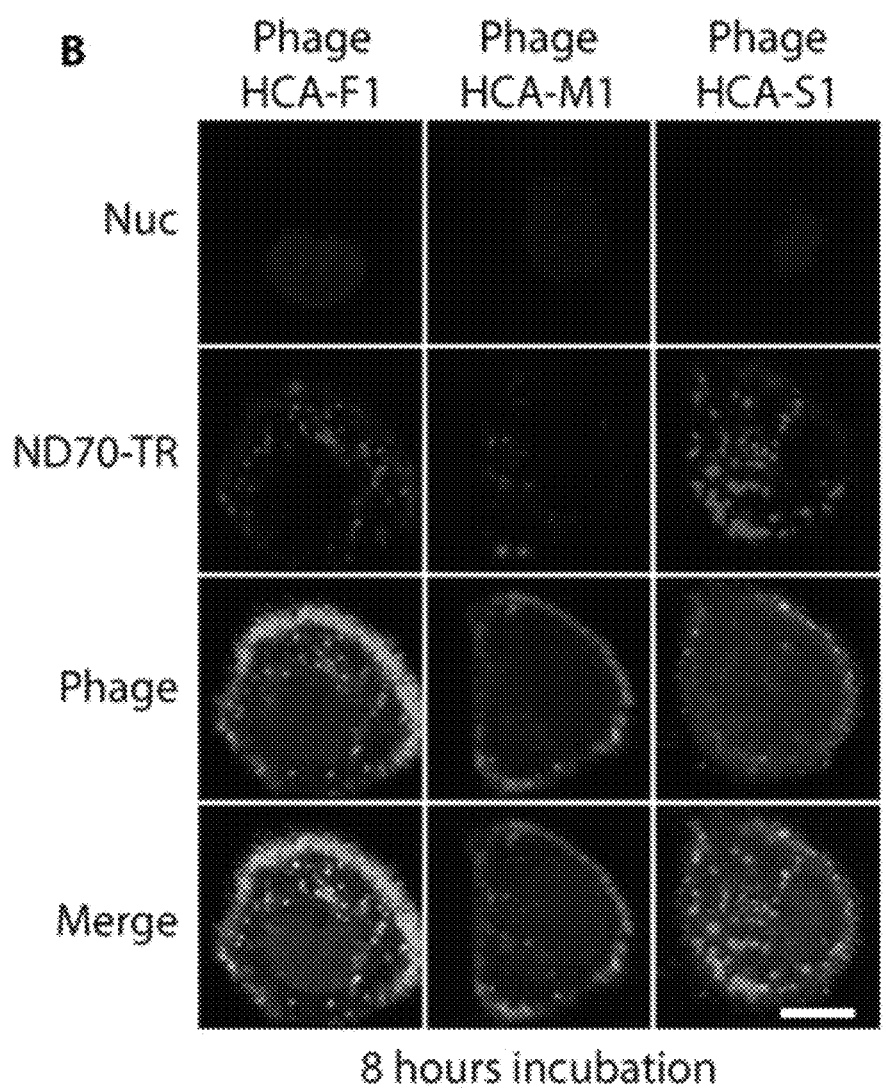
Fig. 4, cont'd.

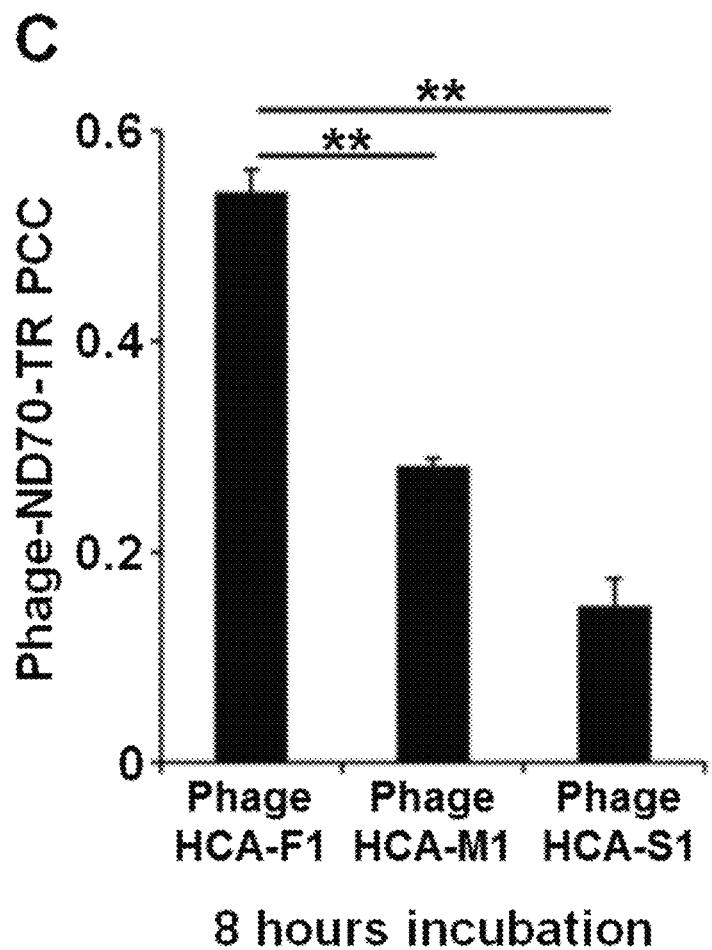
*Fig. 4, cont'd.*

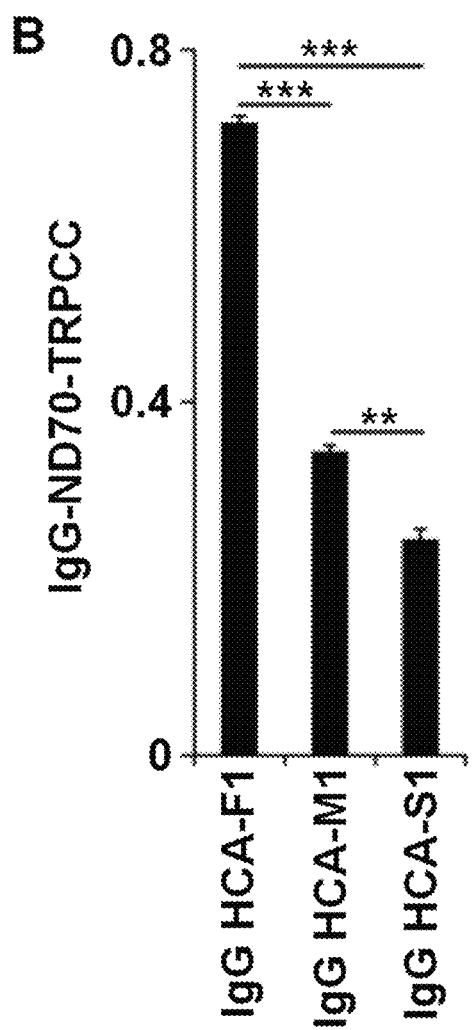
Fig. 5, cont'd.

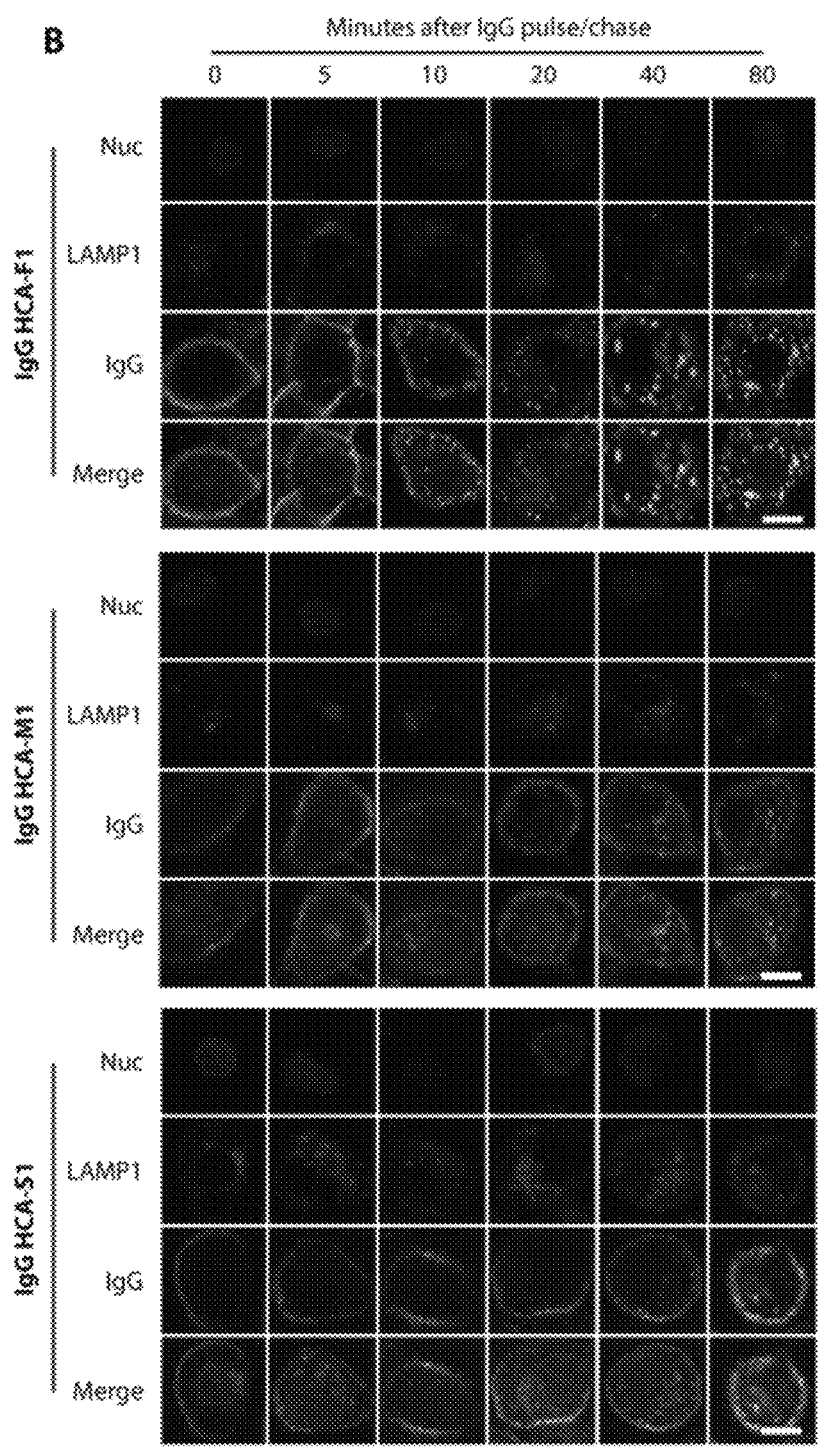
*Fig. 6, cont'd.*

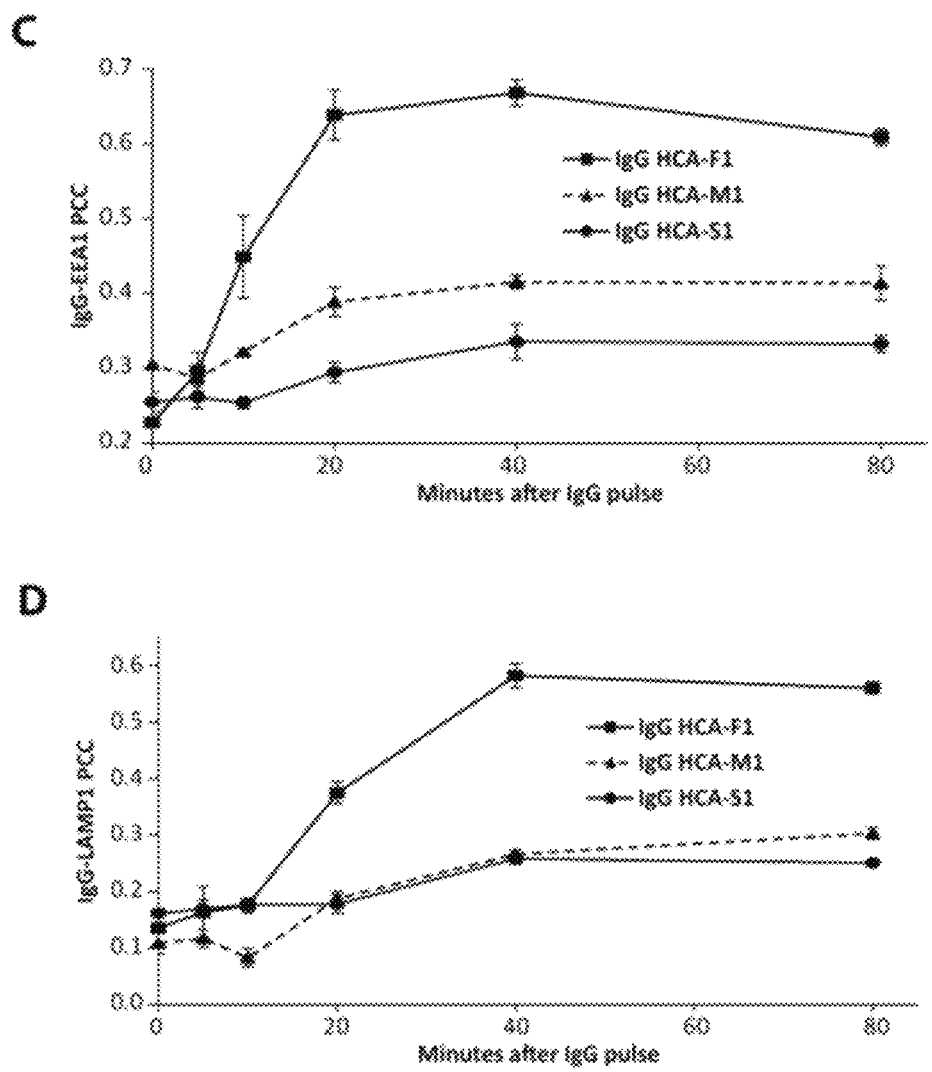
*Fig. 6, cont'd.*

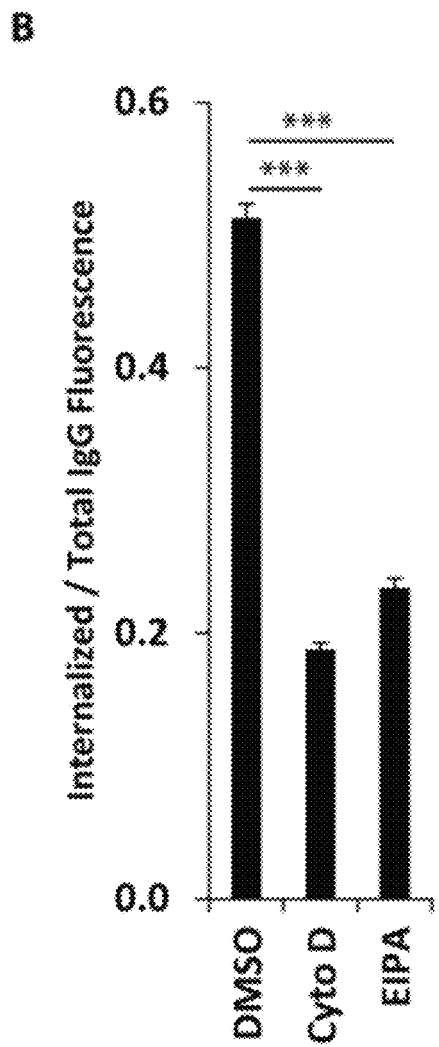
*Fig. 7, cont'd.*

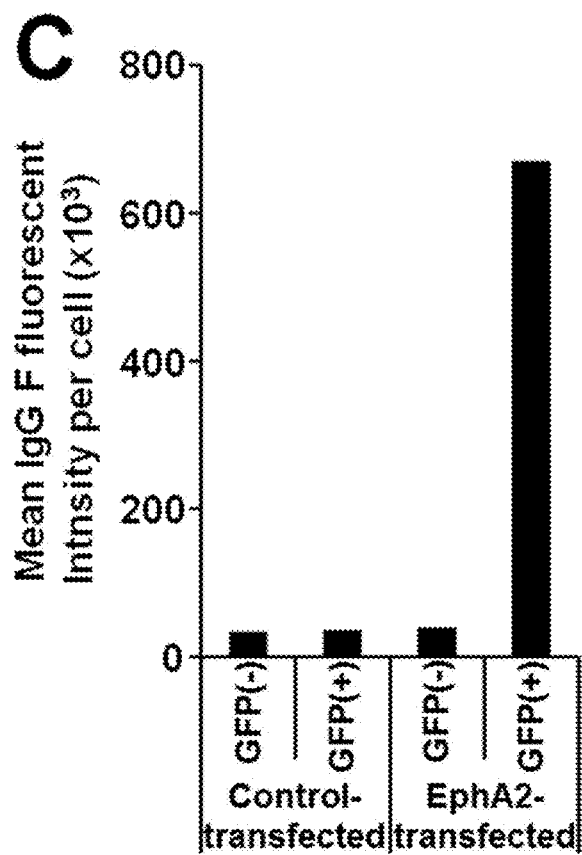
*Fig. 8, cont'd.*

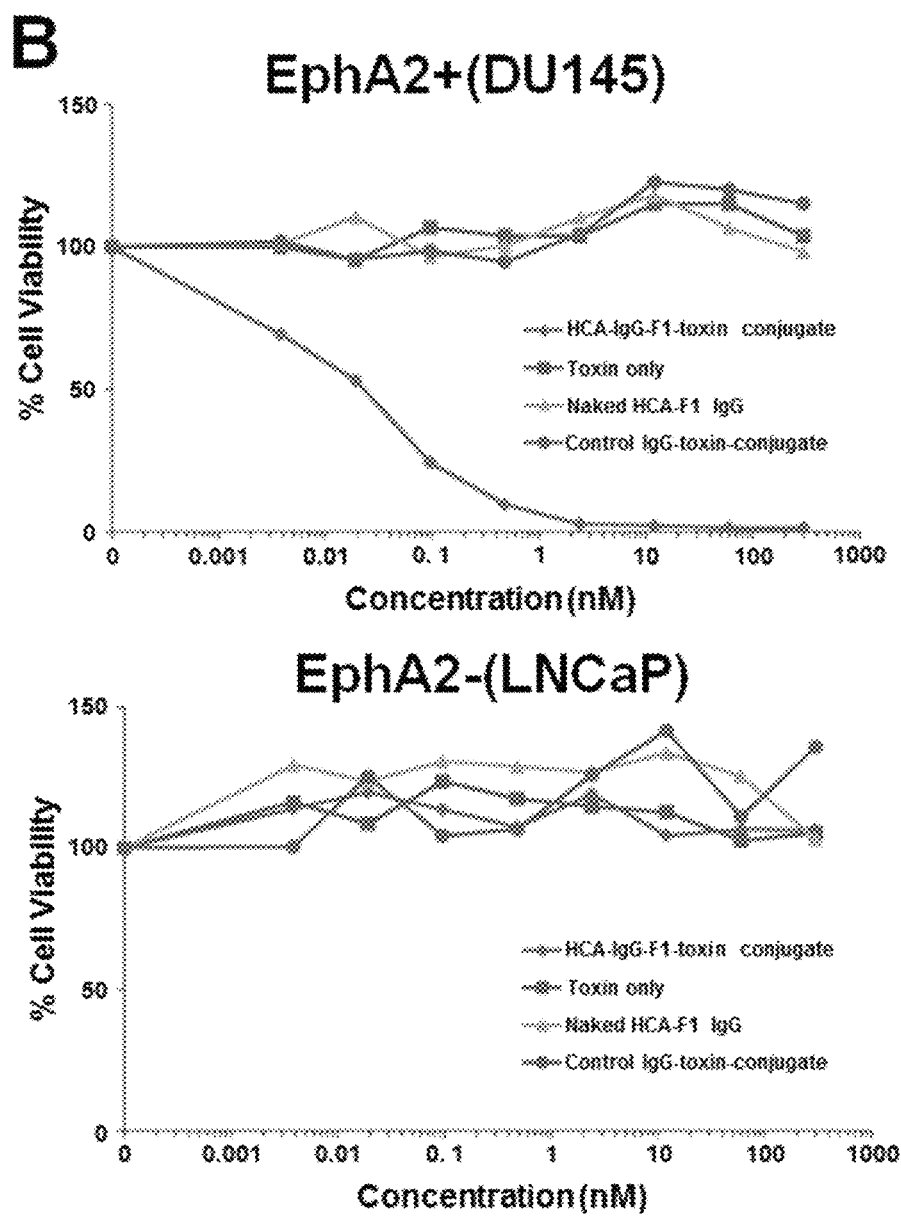
*Fig. 9, cont'd.*

SEQUENCE LISTING

<160> NUMBER OF SEQ ID NOS: 57

<210> SEQ ID NO 1
<211> LENGTH: 8
<212> TYPE: PRT
<213> ORGANISM: Artificial
<220> FEATURE:
<223> OTHER INFORMATION: Synthetic peptide epitope

<400> SEQUENCE: 1

Asp Tyr Lys Asp Asp Asp Asp Lys
1               5

<210> SEQ ID NO 2
<211> LENGTH: 126
<212> TYPE: PRT
<213> ORGANISM: Artificial
<220> FEATURE:
<223> OTHER INFORMATION: Synthetic antibody heavy chain

<400> SEQUENCE: 2

Gln Val Gln Leu Gln Glu Ser Gly Gly Gly Leu Val Gln Pro Gly Gly

```
            1               5                  10                 15
Ser Leu Arg Leu Ser Cys Ala Ala Ser Gly Phe Thr Phe Ser Ser Tyr
                20                  25                 30

Ser Met Asn Trp Val Arg Gln Ala Pro Gly Lys Gly Leu Glu Trp Val
                35                  40                 45

Ser Tyr Ile Ser Ser Ser Ser Thr Ile Tyr Tyr Ala Asp Ser Val
        50                  55                 60

Lys Gly Arg Phe Thr Ile Ser Arg Asp Asn Ala Lys Asn Ser Leu Tyr
 65                 70                  75                 80

Leu Gln Met Asn Ser Leu Arg Ala Glu Asp Thr Ala Val Tyr Tyr Cys
                85                  90                 95

Ala Arg Tyr Arg Leu Pro Asp Phe Trp Ser Gly Tyr Pro Asn Tyr Gly
                100                 105                110

Met Asp Val Trp Gly Gln Gly Thr Thr Val Thr Val Ser Ser
                115                 120                125
```

<210> SEQ ID NO 3
<211> LENGTH: 123
<212> TYPE: PRT
<213> ORGANISM: Artificial
<220> FEATURE:
<223> OTHER INFORMATION: Synthetic antibody heavy chain

<400> SEQUENCE: 3

```
Gln Val Gln Leu Val Glu Ser Gly Gly Gly Leu Val Gln Pro Gly Gly
 1               5                  10                 15

Ser Leu Arg Leu Ser Cys Ala Ala Ser Gly Phe Thr Phe Ser Ser Tyr
                20                  25                 30

Ala Met Ser Trp Val Arg Gln Ala Pro Gly Lys Gly Leu Glu Trp Val
                35                  40                 45

Ser Ala Ile Ser Gly Ser Gly Gly Ser Thr Tyr Tyr Ala Asp Ser Val
        50                  55                 60

Lys Gly Arg Phe Thr Ile Ser Arg Asp Asn Ser Lys Asn Thr Leu Tyr
 65                 70                  75                 80

Leu Gln Met Asn Ser Leu Arg Ala Glu Asp Thr Ala Val Tyr Tyr Cys
                85                  90                 95

Ala Thr Leu Ser Val Glu Trp Tyr Gly Ser Gly Ser Tyr Leu Gly Tyr
                100                 105                110

Trp Gly Gln Gly Thr Leu Val Thr Val Ser Ser
                115                 120
```

<210> SEQ ID NO 4
<211> LENGTH: 120
<212> TYPE: PRT
<213> ORGANISM: Artificial
<220> FEATURE:
<223> OTHER INFORMATION: Synthetic antibody heavy chain

<400> SEQUENCE: 4

```
Gln Val Gln Leu Val Glu Ser Gly Gly Gly Val Val Gln Pro Gly Arg
 1               5                  10                 15

Ser Leu Arg Leu Ser Cys Ala Ala Ser Gly Phe Thr Phe Ser Ser Tyr
                20                  25                 30

Ala Met His Trp Val Arg Gln Ala Pro Gly Lys Gly Leu Glu Trp Val
                35                  40                 45

Ala Val Ile Ser Tyr Asp Gly Ser Asn Lys Tyr Tyr Ala Asp Ser Val
        50                  55                 60
```

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Ala Pro Ala Tyr Ser Tyr Gly Pro Phe Asp Tyr Trp Gly Gln
            100                 105                 110

Gly Thr Leu Val Thr Val Ser Ser
        115                 120

<210> SEQ ID NO 5
<211> LENGTH: 119
<212> TYPE: PRT
<213> ORGANISM: Artificial
<220> FEATURE:
<223> OTHER INFORMATION: Synthetic antibody heavy chain

<400> SEQUENCE: 5

Gln Val Gln Leu Gln Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
             20                  25                  30

Ala Met His Trp Val Arg Gln Ala Pro Gly Lys Gly Leu Glu Trp Val
         35                  40                  45

Ala Val Ile Ser Tyr Asp Gly Ser Asn Lys Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Phe Ser Ser Gly Trp Tyr Tyr Phe Asp Tyr Trp Gly Gln Gly
            100                 105                 110

Thr Leu Val Thr Val Ser Ser
        115

<210> SEQ ID NO 6
<211> LENGTH: 112
<212> TYPE: PRT
<213> ORGANISM: Artificial
<220> FEATURE:
<223> OTHER INFORMATION: Synthetic antibody light chain

<400> SEQUENCE: 6

Gln Ser Val Leu Thr Gln Pro Pro Ser Val Ser Gly Ala Pro Gly Gln
  1               5                  10                  15

Arg Val Thr Ile Ser Cys Thr Gly Ser Ser Ser Asn Ile Gly Ala Gly
             20                  25                  30

Tyr Asp Val His Trp Tyr Gln Gln Leu Pro Gly Thr Ala Pro Lys Leu
         35                  40                  45

Leu Ile Tyr Gly Asn Ser Asn Arg Pro Ser Gly Val Pro Asp Arg Phe
 50                  55                  60

Ser Gly Ser Lys Ser Gly Thr Ser Ala Ser Leu Ala Ile Thr Gly Leu
 65                  70                  75                  80

Gln Ala Glu Asp Glu Ala Asp Tyr Tyr Cys Gln Ser Tyr Asp Ser Ser
                 85                  90                  95

Leu Ser Gly His Val Val Phe Gly Gly Gly Thr Lys Leu Thr Val Leu
            100                 105                 110

<210> SEQ ID NO 7
```

<211> LENGTH: 108
<212> TYPE: PRT
<213> ORGANISM: Artificial
<220> FEATURE:
<223> OTHER INFORMATION: Synthetic antibody light chain

<400> SEQUENCE: 7

```
Asn Phe Met Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala His Tyr Tyr Cys Asn Ser Arg Asp Ser Ser Ala Asn His
                85                  90                  95

Val Val Phe Gly Gly Gly Thr Lys Val Thr Val Leu
            100                 105
```

<210> SEQ ID NO 8
<211> LENGTH: 109
<212> TYPE: PRT
<213> ORGANISM: Artificial
<220> FEATURE:
<223> OTHER INFORMATION: Synthetic antibody light chain

<400> SEQUENCE: 8

```
Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys His Ser Arg Asp Ser Ser Gly Thr His
                85                  90                  95

Leu Arg Val Phe Gly Gly Gly Thr Lys Val Thr Val Leu
            100                 105
```

<210> SEQ ID NO 9
<211> LENGTH: 107
<212> TYPE: PRT
<213> ORGANISM: Artificial
<220> FEATURE:
<223> OTHER INFORMATION: Synthetic antibody light chain

<400> SEQUENCE: 9

```
Asp Ile Gln Met Thr Gln Ser Pro Ser Phe Leu Ser Ala Ser Val Gly
1               5                   10                  15

Asp Arg Ile Thr Ile Thr Cys Arg Ala Ser His Asp Ile Ser Ser Tyr
            20                  25                  30

Phe Ala Trp Tyr Gln Gln Lys Pro Gly Lys Ala Pro Lys Pro Leu Ile
        35                  40                  45
```

-continued

```
Tyr Ala Ala Ser Thr Leu Gln Ser Gly Val Pro Ser Arg Phe Ser Gly
        50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Gln Gln Leu Gly Ser Tyr Pro Leu
                 85                  90                  95

Thr Phe Gly Gly Gly Thr Lys Leu Glu Ile Lys
                100                 105
```

<210> SEQ ID NO 10
<211> LENGTH: 15
<212> TYPE: PRT
<213> ORGANISM: Artificial
<220> FEATURE:
<223> OTHER INFORMATION: Synthetic peptide linker

<400> SEQUENCE: 10

```
Gly Gly Gly Gly Ser Gly Gly Gly Gly Ser Gly Gly Gly Gly Ser
 1               5                  10                  15
```

<210> SEQ ID NO 11
<211> LENGTH: 15
<212> TYPE: PRT
<213> ORGANISM: Artificial
<220> FEATURE:
<223> OTHER INFORMATION: Synthetic pepitde fragment of EphA2

<400> SEQUENCE: 11

```
Arg Asp Cys Asn Ser Phe Pro Gly Gly Ala Ser Ser Cys Lys Glu
 1               5                  10                  15
```

<210> SEQ ID NO 12
<211> LENGTH: 26
<212> TYPE: PRT
<213> ORGANISM: Artificial
<220> FEATURE:
<223> OTHER INFORMATION: Synthetic pepitde fragment of EphA2

<400> SEQUENCE: 12

```
Arg Met His Cys Ala Val Asp Gly Glu Trp Leu Val Pro Ile Gly Gln
 1               5                  10                  15

Cys Leu Cys Gln Ala Gly Tyr Glu Lys Val
                20                  25
```

<210> SEQ ID NO 13
<211> LENGTH: 16
<212> TYPE: PRT
<213> ORGANISM: Artificial
<220> FEATURE:
<223> OTHER INFORMATION: Synthetic pepitde fragment of EphA2

<400> SEQUENCE: 13

```
Lys Val Glu Asp Ala Cys Gln Ala Cys Ser Pro Gly Phe Phe Lys Phe
 1               5                  10                  15
```

<210> SEQ ID NO 14
<211> LENGTH: 16
<212> TYPE: PRT
<213> ORGANISM: Artificial
<220> FEATURE:
<223> OTHER INFORMATION: Synthetic pepitde fragment of EphA2

<400> SEQUENCE: 14

```
Lys Val Glu Asp Ala Cys Gln Ala Cys Ser Pro Gly Phe Phe Lys Phe
 1               5                  10                  15
```

<210> SEQ ID NO 15
<211> LENGTH: 35
<212> TYPE: PRT
<213> ORGANISM: Artificial
<220> FEATURE:
<223> OTHER INFORMATION: Synthetic pepitde fragment of EphA2

<400> SEQUENCE: 15

Lys Phe Glu Ala Ser Glu Ser Pro Cys Leu Glu Cys Pro Glu His Thr
1               5                   10                  15

Leu Pro Ser Pro Glu Gly Ala Thr Ser Cys Glu Cys Glu Glu Gly Phe
            20                  25                  30

Phe Arg Ala
        35

<210> SEQ ID NO 16
<211> LENGTH: 12
<212> TYPE: PRT
<213> ORGANISM: Artificial
<220> FEATURE:
<223> OTHER INFORMATION: Synthetic pepitde fragment of EphA2

<400> SEQUENCE: 16

Arg Tyr Ser Glu Pro Pro His Gly Leu Thr Arg Thr
1               5                   10

<210> SEQ ID NO 17
<211> LENGTH: 12
<212> TYPE: PRT
<213> ORGANISM: Artificial
<220> FEATURE:
<223> OTHER INFORMATION: Synthetic pepitde fragment of EphA2

<400> SEQUENCE: 17

Arg Asn Gly Val Ser Gly Leu Val Thr Ser Arg Ser
1               5                   10

<210> SEQ ID NO 18
<211> LENGTH: 15
<212> TYPE: PRT
<213> ORGANISM: Artificial
<220> FEATURE:
<223> OTHER INFORMATION: Synthetic pepitde fragment of EphA2

<400> SEQUENCE: 18

Arg Thr Ala Ser Val Ser Ile Asn Gln Thr Glu Pro Pro Lys Val
1               5                   10                  15

<210> SEQ ID NO 19
<211> LENGTH: 17
<212> TYPE: PRT
<213> ORGANISM: Artificial
<220> FEATURE:
<223> OTHER INFORMATION: Synthetic pepitde fragment of EphA2

<400> SEQUENCE: 19

Arg Thr Ala Ser Val Ser Ile Asn Gln Thr Glu Pro Pro Lys Val Arg
1               5                   10                  15

Leu

<210> SEQ ID NO 20
<211> LENGTH: 20
<212> TYPE: PRT
<213> ORGANISM: Artificial

```
<220> FEATURE:
<223> OTHER INFORMATION: Synthetic pepitde fragment of EphA2

<400> SEQUENCE: 20

Arg Ser Thr Thr Ser Leu Ser Val Ser Trp Ser Ile Pro Pro Pro Gln
1               5                   10                  15

Gln Ser Arg Val
            20

<210> SEQ ID NO 21
<211> LENGTH: 11
<212> TYPE: PRT
<213> ORGANISM: Artificial
<220> FEATURE:
<223> OTHER INFORMATION: Synthetic pepitde fragment of EphA2

<400> SEQUENCE: 21

Arg Val Trp Lys Tyr Glu Val Thr Tyr Arg Lys
1               5                   10

<210> SEQ ID NO 22
<211> LENGTH: 13
<212> TYPE: PRT
<213> ORGANISM: Artificial
<220> FEATURE:
<223> OTHER INFORMATION: Synthetic pepitde fragment of EphA2

<400> SEQUENCE: 22

Arg Lys Lys Gly Asp Ser Asn Ser Tyr Asn Val Arg Arg
1               5                   10

<210> SEQ ID NO 23
<211> LENGTH: 12
<212> TYPE: PRT
<213> ORGANISM: Artificial
<220> FEATURE:
<223> OTHER INFORMATION: Synthetic pepitde fragment of EphA2

<400> SEQUENCE: 23

Arg Gln Ser Pro Glu Asp Val Tyr Phe Ser Lys Ser
1               5                   10

<210> SEQ ID NO 24
<211> LENGTH: 14
<212> TYPE: PRT
<213> ORGANISM: Artificial
<220> FEATURE:
<223> OTHER INFORMATION: Synthetic pepitde fragment of EphA2

<400> SEQUENCE: 24

Lys Phe Thr Thr Glu Ile His Pro Ser Cys Val Thr Arg Gln
1               5                   10

<210> SEQ ID NO 25
<211> LENGTH: 16
<212> TYPE: PRT
<213> ORGANISM: Artificial
<220> FEATURE:
<223> OTHER INFORMATION: Synthetic pepitde fragment of EphA2

<400> SEQUENCE: 25

Arg Gln Lys Val Ile Gly Ala Gly Glu Phe Gly Glu Val Tyr Lys Gly
1               5                   10                  15

<210> SEQ ID NO 26
<211> LENGTH: 14
```

```
<212> TYPE: PRT
<213> ORGANISM: Artificial
<220> FEATURE:
<223> OTHER INFORMATION: Synthetic pepitde fragment of EphA2

<400> SEQUENCE: 26

Lys Val Ile Gly Ala Gly Glu Phe Gly Glu Val Tyr Lys Gly
1               5                   10

<210> SEQ ID NO 27
<211> LENGTH: 24
<212> TYPE: PRT
<213> ORGANISM: Artificial
<220> FEATURE:
<223> OTHER INFORMATION: Synthetic pepitde fragment of EphA2

<400> SEQUENCE: 27

Lys Gln Arg Val Asp Phe Leu Gly Glu Ala Gly Ile Met Gly Gln Phe
1               5                   10                  15

Ser His His Asn Ile Ile Arg Leu
            20

<210> SEQ ID NO 28
<211> LENGTH: 22
<212> TYPE: PRT
<213> ORGANISM: Artificial
<220> FEATURE:
<223> OTHER INFORMATION: Synthetic pepitde fragment of EphA2

<400> SEQUENCE: 28

Arg Val Asp Phe Leu Gly Glu Ala Gly Ile Met Gly Gln Phe Ser His
1               5                   10                  15

His Asn Ile Ile Arg Leu
            20

<210> SEQ ID NO 29
<211> LENGTH: 13
<212> TYPE: PRT
<213> ORGANISM: Artificial
<220> FEATURE:
<223> OTHER INFORMATION: Synthetic pepitde fragment of EphA2

<400> SEQUENCE: 29

Arg Asn Ile Leu Val Asn Ser Asn Leu Val Cys Lys Val
1               5                   10

<210> SEQ ID NO 30
<211> LENGTH: 18
<212> TYPE: PRT
<213> ORGANISM: Artificial
<220> FEATURE:
<223> OTHER INFORMATION: Synthetic pepitde fragment of EphA2

<400> SEQUENCE: 30

Arg Val Leu Glu Asp Asp Pro Glu Ala Thr Tyr Thr Thr Ser Gly Gly
1               5                   10                  15

Lys Ile

<210> SEQ ID NO 31
<211> LENGTH: 22
<212> TYPE: PRT
<213> ORGANISM: Artificial
<220> FEATURE:
<223> OTHER INFORMATION: Synthetic pepitde fragment of EphA2

<400> SEQUENCE: 31
```

```
Arg Val Leu Glu Asp Asp Pro Glu Ala Thr Tyr Thr Thr Ser Gly Gly
1               5                   10                  15

Lys Ile Pro Ile Arg Trp
            20

<210> SEQ ID NO 32
<211> LENGTH: 12
<212> TYPE: PRT
<213> ORGANISM: Artificial
<220> FEATURE:
<223> OTHER INFORMATION: Synthetic pepitde fragment of EphA2

<400> SEQUENCE: 32

Arg Trp Thr Ala Pro Glu Ala Ile Ser Tyr Arg Lys
1               5                   10

<210> SEQ ID NO 33
<211> LENGTH: 12
<212> TYPE: PRT
<213> ORGANISM: Artificial
<220> FEATURE:
<223> OTHER INFORMATION: Synthetic pepitde fragment of EphA2

<400> SEQUENCE: 33

Lys Phe Ala Asp Ile Val Ser Ile Leu Asp Lys Leu
1               5                   10

<210> SEQ ID NO 34
<211> LENGTH: 19
<212> TYPE: PRT
<213> ORGANISM: Artificial
<220> FEATURE:
<223> OTHER INFORMATION: Synthetic pepitde fragment of EphA2

<400> SEQUENCE: 34

Arg Val Ser Ile Arg Leu Pro Ser Thr Ser Gly Ser Glu Gly Val Pro
1               5                   10                  15

Phe Arg Thr

<210> SEQ ID NO 35
<211> LENGTH: 15
<212> TYPE: PRT
<213> ORGANISM: Artificial
<220> FEATURE:
<223> OTHER INFORMATION: Synthetic pepitde fragment of EphA2

<400> SEQUENCE: 35

Arg Leu Pro Ser Thr Ser Gly Ser Glu Gly Val Pro Phe Arg Thr
1               5                   10                  15

<210> SEQ ID NO 36
<211> LENGTH: 13
<212> TYPE: PRT
<213> ORGANISM: Artificial
<220> FEATURE:
<223> OTHER INFORMATION: Synthetic pepitde fragment of EphA2

<400> SEQUENCE: 36

Lys Val Val Gln Met Thr Asn Asp Asp Ile Lys Arg Ile
1               5                   10

<210> SEQ ID NO 37
<211> LENGTH: 11
<212> TYPE: PRT
<213> ORGANISM: Artificial
```

```
<220> FEATURE:
<223> OTHER INFORMATION: Synthetic pepitde fragment of EphA2

<400> SEQUENCE: 37

Arg Ile Ala Tyr Ser Leu Leu Gly Leu Lys Asp
1               5                   10

<210> SEQ ID NO 38
<211> LENGTH: 5
<212> TYPE: PRT
<213> ORGANISM: Artificial
<220> FEATURE:
<223> OTHER INFORMATION: Antibody CDR sequence

<400> SEQUENCE: 38

Ser Tyr Ser Met Asn
1               5

<210> SEQ ID NO 39
<211> LENGTH: 17
<212> TYPE: PRT
<213> ORGANISM: Artificial
<220> FEATURE:
<223> OTHER INFORMATION: Antibody CDR sequence

<400> SEQUENCE: 39

Tyr Ile Ser Ser Ser Ser Ser Thr Ile Tyr Tyr Ala Asp Ser Val Lys
1               5                   10                  15

Gly

<210> SEQ ID NO 40
<211> LENGTH: 17
<212> TYPE: PRT
<213> ORGANISM: Artificial
<220> FEATURE:
<223> OTHER INFORMATION: Antibody CDR sequence

<400> SEQUENCE: 40

Tyr Arg Leu Pro Asp Phe Trp Ser Gly Tyr Pro Asn Tyr Gly Met Asp
1               5                   10                  15

Val

<210> SEQ ID NO 41
<211> LENGTH: 5
<212> TYPE: PRT
<213> ORGANISM: Artificial
<220> FEATURE:
<223> OTHER INFORMATION: Antibody CDR sequence

<400> SEQUENCE: 41

Ser Tyr Ala Met Ser
1               5

<210> SEQ ID NO 42
<211> LENGTH: 17
<212> TYPE: PRT
<213> ORGANISM: Artificial
<220> FEATURE:
<223> OTHER INFORMATION: Antibody CDR sequence

<400> SEQUENCE: 42

Ala Ile Ser Gly Ser Gly Gly Ser Thr Tyr Tyr Ala Asp Ser Val Lys
1               5                   10                  15

Gly
```

```
<210> SEQ ID NO 43
<211> LENGTH: 14
<212> TYPE: PRT
<213> ORGANISM: Artificial
<220> FEATURE:
<223> OTHER INFORMATION: Antibody CDR sequence

<400> SEQUENCE: 43

Leu Ser Val Glu Trp Tyr Gly Ser Gly Ser Tyr Leu Gly Tyr
1               5                   10

<210> SEQ ID NO 44
<211> LENGTH: 5
<212> TYPE: PRT
<213> ORGANISM: Artificial
<220> FEATURE:
<223> OTHER INFORMATION: Antibody CDR sequence

<400> SEQUENCE: 44

Ser Tyr Ala Met His
1               5

<210> SEQ ID NO 45
<211> LENGTH: 17
<212> TYPE: PRT
<213> ORGANISM: Artificial
<220> FEATURE:
<223> OTHER INFORMATION: Antibody CDR sequence

<400> SEQUENCE: 45

Val Ile Ser Tyr Asp Gly Ser Asn Lys Tyr Tyr Ala Asp Ser Val Lys
1               5                   10                  15

Gly

<210> SEQ ID NO 46
<211> LENGTH: 11
<212> TYPE: PRT
<213> ORGANISM: Artificial
<220> FEATURE:
<223> OTHER INFORMATION: Antibody CDR sequence

<400> SEQUENCE: 46

Ala Pro Ala Tyr Ser Tyr Gly Pro Phe Asp Tyr
1               5                   10

<210> SEQ ID NO 47
<211> LENGTH: 10
<212> TYPE: PRT
<213> ORGANISM: Artificial
<220> FEATURE:
<223> OTHER INFORMATION: Antibody CDR sequence

<400> SEQUENCE: 47

Phe Ser Ser Gly Trp Tyr Tyr Phe Asp Tyr
1               5                   10

<210> SEQ ID NO 48
<211> LENGTH: 14
<212> TYPE: PRT
<213> ORGANISM: Artificial
<220> FEATURE:
<223> OTHER INFORMATION: Antibody CDR sequence

<400> SEQUENCE: 48

Thr Gly Ser Ser Ser Asn Ile Gly Ala Gly Tyr Asp Val His
1               5                   10
```

```
<210> SEQ ID NO 49
<211> LENGTH: 8
<212> TYPE: PRT
<213> ORGANISM: Artificial
<220> FEATURE:
<223> OTHER INFORMATION: Antibody CDR sequence

<400> SEQUENCE: 49

Tyr Gly Asn Ser Asn Arg Pro Ser
1               5

<210> SEQ ID NO 50
<211> LENGTH: 12
<212> TYPE: PRT
<213> ORGANISM: Artificial
<220> FEATURE:
<223> OTHER INFORMATION: Antibody CDR sequence

<400> SEQUENCE: 50

Gln Ser Tyr Asp Ser Ser Leu Ser Gly His Val Val
1               5                   10

<210> SEQ ID NO 51
<211> LENGTH: 11
<212> TYPE: PRT
<213> ORGANISM: Artificial
<220> FEATURE:
<223> OTHER INFORMATION: Antibody CDR sequence

<400> SEQUENCE: 51

Gln Gly Asp Ser Leu Arg Ser Tyr Tyr Ala Ser
1               5                   10

<210> SEQ ID NO 52
<211> LENGTH: 8
<212> TYPE: PRT
<213> ORGANISM: Artificial
<220> FEATURE:
<223> OTHER INFORMATION: Antibody CDR sequence

<400> SEQUENCE: 52

Tyr Gly Lys Asn Asn Arg Pro Ser
1               5

<210> SEQ ID NO 53
<211> LENGTH: 11
<212> TYPE: PRT
<213> ORGANISM: Artificial
<220> FEATURE:
<223> OTHER INFORMATION: Antibody CDR sequence

<400> SEQUENCE: 53

Asn Ser Arg Asp Ser Ser Ala Asn His Val Val
1               5                   10

<210> SEQ ID NO 54
<211> LENGTH: 12
<212> TYPE: PRT
<213> ORGANISM: Artificial
<220> FEATURE:
<223> OTHER INFORMATION: Antibody CDR sequence

<400> SEQUENCE: 54

His Ser Arg Asp Ser Ser Gly Thr His Leu Arg Val
1               5                   10
```

```
<210> SEQ ID NO 55
<211> LENGTH: 11
<212> TYPE: PRT
<213> ORGANISM: Artificial
<220> FEATURE:
<223> OTHER INFORMATION: Antibody CDR sequence

<400> SEQUENCE: 55

Arg Ala Ser His Asp Ile Ser Ser Tyr Phe Ala
1               5                   10

<210> SEQ ID NO 56
<211> LENGTH: 8
<212> TYPE: PRT
<213> ORGANISM: Artificial
<220> FEATURE:
<223> OTHER INFORMATION: Antibody CDR sequence

<400> SEQUENCE: 56

Tyr Ala Ala Ser Thr Leu Gln Ser
1               5

<210> SEQ ID NO 57
<211> LENGTH: 9
<212> TYPE: PRT
<213> ORGANISM: Artificial
<220> FEATURE:
<223> OTHER INFORMATION: Antibody CDR sequence

<400> SEQUENCE: 57

Gln Gln Leu Gly Ser Tyr Pro Leu Thr
1               5
```

TUMOR SELECTIVE MACROPINOCYTOSIS-DEPENDENT RAPIDLY INTERNALIZING ANTIBODIES

CROSS-REFERENCE TO RELATED APPLICATIONS

This application is a divisional of U.S. Ser. No. 15/321,684, filed on Dec. 22, 2016, which is a US 371 National phase of PCT/US2015/039741, filed Jul. 9, 2015, which claims benefit of and priority to U.S. Ser. No. 62/023,689, filed on Jul. 11, 2014, all of which are incorporated herein by reference in their entirety for all purposes.

STATEMENT OF GOVERNMENTAL SUPPORT

This invention was made with government support under Grants No. R01 CA118919, R01 CA129491 and R01 CA171315 awarded by the National Institutes of Health. The Government has certain rights in this invention.

INCORPORATION BY REFERENCE OF SEQUENCE LISTING PROVIDED AS A TEXT FILE

This application contains references to nucleic acid sequences that have been submitted concurrently herewith as the sequence listing text file "UCSF-P036D1UScorrST25.txt", file size 20,890 bytes, created on Apr. 17, 2022, which is incorporated by reference in its entirety pursuant to 37 C.F.R. § 1.52(e)(5).

BACKGROUND

There is significant interest in the development of targeted therapeutics such as antibody drug conjugates that have the potential to improve the therapeutic window of cytotoxic drugs by delivering them specifically and intracellularly to cancer cells (Austin et al. (2004) *Mol. Biol. Cell.* 15: 5268-5282; Burris et al. (2011) *Clin. Breast Cancer.* 11: 275-282; Sievers and Senter (2013) *Annu. Rev. Med.* 64: 15-29; Behrens and Liu (2013) MAbs, 6(1): 46-53; Sutherland et al. (2006) *J Biol. Chem.* 281: 10540-10547). The pathway by which the targeted agent enters tumor cells can influence both the uptake efficiency and the intracellular fate of the internalized agent, both of which contribute to the cytotoxic potency (Sutherland et al. (2006) *J. Biol. Chem.* 281: 10540-10547; Erickson et al. (2006) *Cancer Res.* 66: 4426-4433).

Endocytosis pathways can be subdivided into four categories: 1) clathrin-mediated endocytosis, 2) caveolae, 3) macropinocytosis, and 4) phagocytosis. Clathrin-mediated endocytosis is mediated by small (approx. 100 nm in diameter) vesicles that have a morphologically characteristic coat made up of a complex of proteins that are mainly associated with the cytosolic protein clathrin. Clathrin-coated vesicles (CCVs) are found in virtually all cells and form domains of the plasma membrane termed clathrin-coated pits. Coated pits can concentrate large extracellular molecules that have different receptors responsible for the receptor-mediated endocytosis of ligands, e.g. low density lipoprotein, transferrin, growth factors, antibodies and many others.

Caveolae are the most common reported non-clathrin-coated plasma membrane buds, which exist on the surface of many, but not all cell types. They consist of the cholesterol-binding protein caveolin (Vip21) with a bilayer enriched in cholesterol and glycolipids. Caveolae are small (approximately 50 nm in diameter) flask-shape pits in the membrane that resemble the shape of a cave (hence the name caveolae). They can constitute up to a third of the plasma membrane area of the cells of some tissues, being especially abundant in smooth muscle, type I pneumocytes, fibroblasts, adipocytes, and endothelial cells (Burris et al. (2011) *Clin. Breast Cancer.* 11: 275-282). Uptake of extracellular molecules is also believed to be specifically mediated via receptors in caveolae.

Macropinocytosis, which usually occurs from highly ruffled regions of the plasma membrane, is the invagination of the cell membrane to form a pocket, which then pinches off into the cell to form a vesicle (~0.5-5 µm in diameter) filled with a large volume of extracellular fluid and molecules within it (equivalent to ~100 CCVs). The filling of the pocket occurs in a non-specific manner. The vesicle then travels into the cytosol and fuses with other vesicles such as endosomes and lysosomes.

Phagocytosis is the process by which cells bind and internalize particulate matter larger than around 0.75 µm in diameter, such as small-sized dust particles, cell debris, micro-organisms and even apoptotic cells, which only occurs in specialized cells. These processes involve the uptake of larger membrane areas than clathrin-mediated endocytosis and caveolae pathway.

SUMMARY

Macropinocytosis was investigated as an intriguing pathway for cellular entry because it is a form of bulk uptake and can therefore efficiently and rapidly internalize targeting agents. Macropinosomes comprise large, endocytic vesicles that range from 0.2 µm to 3 µm in size, which are up to 30-fold larger than the 0.1 µm average size of protein-coated, endocytic vesicles (Hewlett et al. (1994) *J. Cell Biol.* 124: 689-703). Additionally, studies have shown that macropinocytosis is selectively upregulated in Ras-transformed cancers (a common oncogenic mutation in human cancers) and plays an important role in tumor cell homeostasis by serving as an amino acid supply route (Commisso et al. (2013) *Nature.* 497: 633-637), suggesting that targeted therapeutics based on antibodies that internalize via the macropinocytosis pathway may provide additional tumor-specificity against a wide variety of human cancers.

To therapeutically explore the utility of antibodies that gain entry into tumor cells via receptor-dependent macropinocytosis, a generally applicable method was developed that readily identifies such antibodies. While phage antibody display libraries have been extensively used to select for antibodies that internalize into tumor cells, it is believed that no methods have been previously developed to uncover antibodies capable of cellular entry through the macropinocytosis pathway.

To this end, a high content analysis (HCA)-based screening strategy was developed that employs automated image-based analysis to identify phage antibodies that colocalize with a macropinocytosis marker (e.g., Texas Red-conjugated 70 kDa neutral dextran (ND70-TR)). The HCA protocol was used to screen single chain variable fragment (scFv) phage antibody display libraries that were previously generated by laser capture microdissection (LCM)-based selection on live tumor cells and tumor tissues, which are highly enriched for internalizing phage antibodies binding to prostate tumor cells in situ residing in their tissue microenvironment (Ruan et al. (2006)*Mol. Cell* Proteomics. 5: 2364-2373), and identified antibodies that are capable of efficient internalization via macropinocytosis. Kinetics and subcellular colocalization studies were performed for phage antibodies as well as full-length immunoglobulin G (IgG) molecules derived from the parental scFvs and identified a highly active, macropinocytosing antibody that rapidly internalizes and colocalizes with early endosomal and lysosomal markers. The target antigen was identified as EphA2 by immunoprecipitation and mass spectrometry. To confirm internalization by an independent functional assay and to demonstrate therapeutic potential, an antibody-toxin conjugate was created and it showed potent and specific cytotoxic activity against a panel of EphA2-positive tumor cell lines. It is believed this is the first description of a generally applicable screening strategy to uncover macropinocytosing antibodies, enabling further exploration of this class of antibody-antigen pairs for the development of effective antibody-targeted therapeutics.

Various embodiments contemplated herein may include, but need not be limited to, one or more of the following:

Embodiment 1: A method of preparing antibodies that are internalized into a cell by a macropinocytosis pathway, said method comprising:
  contacting target cells with members of an antibody library and with a marker for macropinocytosis;
  identifying internalized antibodies that co-localize in said target cells with said marker for macropinocytosis; and
  selecting those antibodies that co-localize with said marker for macropinocytosis.

Embodiment 2: The method of embodiment 1, wherein said members of an antibody library are members of a phage display library.

Embodiment 3: The method of embodiment 1, wherein said members of an antibody library are members of a yeast display library.

Embodiment 4: The method according to any one of embodiments 1-3, wherein said antibody library is an antibody library that is enriched for antibodies that bind to tumor cells.

Embodiment 5: The method of embodiment 4, wherein said antibody library is an antibody library that is enriched for antibodies that bind to tumor cells and said enrichment is by laser capture microdissection (LCM) of antibodies that bind to tumor cells.

Embodiment 6: The method according to any one of embodiments 1-5, wherein said antibody library is an antibody library that is enriched for antibodies that are internalized into tumor cells.

Embodiment 7: The method according to any one of embodiments 1-6, wherein said marker for macropinocytosis includes a marker selected from the group consisting of high molecular weight dextran, latex beads, glass beads, Lucifer yellow, and soluble enzymes such as horseradish peroxidase.

Embodiment 8: The method of embodiment 7, wherein said marker for macropinocytosis includes labeled high molecular weight dextran.

Embodiment 9: The method of embodiment 8, wherein said marker for macropinocytosis includes labeled high molecular weight dextran having a molecular weight that ranges from about 60 kDa to about 80 kDa.

Embodiment 10: The method of embodiment 8, wherein said marker for macropinocytosis includes labeled high molecular weight dextran having a molecular weight of about 70 kDa.

Embodiment 11: The method of embodiment 7, wherein, wherein said marker for macropinocytosis includes latex beads or glass beads.

Embodiment 12: The method of embodiment 11, wherein said latex beads or glass beads are approximately 20 nm in diameter.

Embodiment 13: The method according to any one of embodiments 1-12, wherein said marker for macropinocytosis is labeled with a detectable label.

Embodiment 14: The method of embodiment 13, wherein said marker for macropinocytosis is labeled with a fluorescent label.

Embodiment 15: The method of embodiment 14, wherein said marker for macropinocytosis is labeled with fluorescein isothiocyanate (FITC) or tetrarhodamine isothiocyanate (TRITC).

Embodiment 16: The method of embodiment 7, wherein, wherein said marker for macropinocytosis includes Lucifer yellow.

Embodiment 17: The method according to any one of embodiments 1-16, wherein said target cells comprise cells of tumor cell lines.

Embodiment 18: The method of embodiment 17, wherein said target cells are selected from the group consisting of PC3, DU145, HeLa, MDA-MB-231, Hs5786, MDA-435, BT549, SKOV3, HeyA8, OVCAR3, PANC1, MIAPaCa2, BxPC3, T24, TCCSUP, UMUC-3, TE1, AGS, SGC-7901, M28, VAMT-1, A549, A431, A172MG, DBTRG-5MG, U-251MG, U87MG, T84, THP1, U373, U937, VCaP, SiHa, FM3, DuCaP, A253, A172, 721, SiHa, and LNCaP.

Embodiment 19: The method according to any one of embodiments 1-18, wherein said contacting includes incubating said members of an antibody library and/or said marker for macropinocytosis with said cells.

Embodiment 20: The method according to any one of embodiments 1-19, wherein said contacting includes incubating said members of an antibody library and/or said marker for macropinocytosis with said cells for a period of at least 1 hour, or at least 2 hours, or at least 3 hours, or at least 4 hours, or at least 6 hours, or at least 8 hours, or at least 10 hours, or at least 12 hours, or at least 16 hours, or at least 20 hours, or at least 24 hours.

Embodiment 21: The method according to any one of embodiments 1-19, wherein said identifying includes high content screening (HCS) of said cells.

Embodiment 22: The method of embodiment 21, wherein said high content screening is performed using a fluorescent microscope and automated digital microscopy.

Embodiment 23: The method according to any one of embodiments 1-22, wherein said colocalized antibody is labeled with a fluorescent label attached to a second antibody that binds said colocalized antibody.

Embodiment 24: The method of embodiment 23, wherein said second antibody includes an anti-fd bacteriophage.

Embodiment 25: The method according to any one of embodiments 1-24, wherein said method further includes selecting internalized antibodies that colocalize with a lysosomal marker.

Embodiment 26: The method of embodiment 25, wherein said antibody colocalizes with LAMP1.

Embodiment 27: The method according to any one of embodiments 1-26, wherein said selecting comprises recovering the antibody from the sample used in the HCS analysis.

Embodiment 28: The method according to any one of embodiments 1-26, wherein said selecting comprises selecting the antibodies from the library corresponding to the antibodies identified in the HCS analysis.

Embodiment 29: The method according to any one of embodiments 1-28, wherein said selecting comprises determining the amino acid sequence of said antibody.

Embodiment 30: The method according to any one of embodiments 1-29, wherein said selecting comprises converting said antibody into an intact immunoglobulin.

Embodiment 31: The method of embodiment 30, wherein said selecting comprises converting said antibody into an IgG.

Embodiment 32: The method of embodiment 30, wherein said selecting comprises converting said antibody into an IgA.

Embodiment 33: An isolated antibody that is internalized into a cell via a macropinocytosis pathway, wherein said antibody is an antibody that binds to ephrin type A receptor 2 (EphA2).

Embodiment 34: The antibody of embodiment 33, wherein said antibody is an antibody that is identified using the method of embodiments 1-32.

Embodiment 35: The antibody according to any one of embodiments 33-34, wherein said antibody is a human antibody.

Embodiment 36: The antibody according to any one of embodiments 33-35, wherein said antibody is an antibody selected from the group consisting of an intact immunoglobulin, a Fab, a (Fab')$_2$, an scFv, and an (ScFv')$_2$.

Embodiment 37: The antibody of embodiment 36, wherein said antibody is an intact immunoglobulin.

Embodiment 38: The antibody of embodiment 37, wherein said antibody is an IgG or an IgA.

Embodiment 39: The antibody according to any one of embodiments 33-38, wherein said antibody is a monoclonal antibody.

Embodiment 40: The antibody according to any one of embodiments 33-39, wherein said antibody is internalized via a macropinocytosis pathway in a cell in which macropinocytosis is upregulated.

Embodiment 41: The antibody of embodiment 40, wherein said cell is a cancer cell.

Embodiment 42: The antibody of embodiment 41, wherein said cell is a Ras-transformed cancer cell.

Embodiment 43: The antibody of embodiment 41, wherein said cell is a cancer cell selected from the group consisting of PC3, DU145, HeLa, MDA-MB-231, Hs5786, MDA-435, BT549, SKOV3, HeyA8, OVCAR3, PANC1, MIAPaCa2, BxPC3, T24, TCCSUP, UMUC-3, TE1, AGS, SGC-7901, M28, VAMT-1, A549, A431, A172MG, DBTRG-5MG, U-251MG, U87MG, T84, THP1, U373, U937, VCaP, SiHa, FM3, DuCaP, A253, A172, 721, SiHa, and LNCaP.

Embodiment 44: The antibody according to any one of embodiments 33-43, wherein said antibody competes with one or more antibodies selected from the group consisting of HCA-F1, and HCA-F2 for binding EphA2.

Embodiment 45: The antibody of embodiment 44, wherein said antibody competes with HCA-F1 for binding EphA2.

Embodiment 46: The antibody of embodiment 44, wherein said antibody competes with HCA-F2 for binding EphA2.

Embodiment 47: The antibody of embodiment 44, wherein said antibody binds the same epitope bound by HCA-F1.

Embodiment 48: The antibody of embodiment 44, wherein said antibody binds the same epitope bound by HCA-F2.

Embodiment 49: The antibody according to any one of embodiments 33-48, wherein said antibody includes VH CDR1, VH CDR2, and VH CDR3 of HCA-F1.

Embodiment 50: The antibody according to any one of embodiments 33-48, or embodiment 49, wherein said antibody includes VL CDR1, VL CDR2, and VL CDR3 of HCA-F1.

Embodiment 51: The antibody according to any one of embodiments 33-48, wherein said antibody includes VH CDR1, VH CDR2, and VH CDR3 of HCA-F2.

Embodiment 52: The antibody according to any one of embodiments 33-48, or embodiment 51, wherein said antibody includes VL CDR1, VL CDR2, and VL CDR3 of HCA-F2.

Embodiment 53: The antibody according to any one of embodiments 33-48, wherein said antibody includes the VH and/or the VL domain of HCA-F1.

Embodiment 54: The antibody of embodiment 53, wherein said antibody includes the VH and the VL domain of HCA-F1.

Embodiment 55: The antibody according to any one of embodiments 33-48, wherein said antibody includes the VH and/or the VL domain of HCA-F2.

Embodiment 56: The antibody of embodiment 55, wherein said antibody includes the VH and the VL domain of HCA-F2.

Embodiment 57: An isolated antibody that binds to a tumor cell.

Embodiment 58: The antibody of embodiment 57, wherein said antibody is a human antibody.

Embodiment 59: The antibody according to any one of embodiments 57-58, wherein said antibody is a monoclonal antibody.

Embodiment 60: The antibody according to any one of embodiments 57-59, wherein said cell is a cancer cell.

Embodiment 61: The antibody of embodiment 60, wherein said cell is a cancer cell selected from the group consisting of PC3, DU145, HeLa, MDA-MB-231, Hs5786, MDA-435, BT549, SKOV3, HeyA8, OVCAR3, PANC1, MIAPaCa2, BxPC3, T24, TCCSUP, UMUC-3, TE1, AGS, SGC-7901, M28, VAMT-1, A549, A431, A172MG, DBTRG-5MG, U-251MG, U87MG, T84, THP1, U373, U937, VCaP, SiHa, FM3, DuCaP, A253, A172, 721, SiHa, and LNCaP.

Embodiment 62: The antibody according to any one of embodiments 57-61, wherein said antibody includes VH CDR1, VH CDR2, and VH CDR3 of HCA-M1.

Embodiment 63: The antibody according to any one of embodiments 57-61, or embodiment 62, wherein said antibody includes VL CDR1, VL CDR2, and VL CDR3 of HCA-M1.

Embodiment 64: The antibody according to any one of embodiments 57-61, wherein said antibody includes VH CDR1, VH CDR2, and VH CDR3 of HCA-S1.

Embodiment 65: The antibody according to any one of embodiments 57-61, or embodiment 64, wherein said antibody includes VL CDR1, VL CDR2, and VL CDR3 of HCA-S1.

Embodiment 66: The antibody according to any one of embodiments 57-61, wherein said antibody includes the VH and/or the VL domain of HCA-M1.

Embodiment 67: The antibody of embodiment 66, wherein said antibody includes the VH and the VL domain of HCA-M1.

Embodiment 68: The antibody according to any one of embodiments 57-61, wherein said antibody includes the VH and/or the VL domain of HCA-S1.

Embodiment 69: The antibody of embodiment 68, wherein said antibody includes the VH and the VL domain of HCA-S1.

Embodiment 70: The antibody according to any one of embodiments 33-69, wherein said antibody is a substantially intact immunoglobulin.

Embodiment 71: The antibody of embodiment 70, wherein said antibody includes an IgA, IgE, or IgG.

Embodiment 72: The antibody of embodiment 70, wherein said antibody includes an IgG1.

Embodiment 73: The antibody according to any one of embodiments 33-56, wherein said antibody is an antibody fragment selected from the group consisting of Fv, Fab, (Fab')$_2$, (Fab')$_3$, IgGACH2, and a minibody.

Embodiment 74: The antibody according to any one of embodiments 33-69, wherein said antibody is a single chain antibody.

Embodiment 75: The antibody of embodiment 74, wherein the VL region of said antibody is attached to the VH region of said antibody by an amino acid linker ranging in length from about 3 amino acids up to about 15 amino acids.

Embodiment 76: The antibody of embodiment 74, wherein the VL region of said antibody is attached to the VH region of said antibody by linker having the amino acid sequence (Gly$_4$Ser)$_3$ SEQ ID NO:10.

Embodiment 77: An immunoconjugate including an antibody according to any one of embodiments 33-76 attached to an effector wherein said effector is selected from the group consisting of a second antibody, a detectable label, a cytotoxin or cytostatic agent, a liposome containing a drug, a radionuclide, a drug, a prodrug, a viral particle, a cytokine, a chelate, and an siRNA.

Embodiment 78: The immunoconjugate of embodiment 77, wherein said antibody is attached to an siRNA.

Embodiment 79: The immunoconjugate of embodiment 78, wherein said siRNA carried by a liposome or mesoporous silica.

Embodiment 80: The immunoconjugate of embodiments 78-79, wherein said siRNA is an EphA2-targeted siRNA.

Embodiment 81: The immunoconjugate of embodiment 77, wherein said antibody is attached to a cytotoxin.

Embodiment 82: The immunoconjugate of embodiment 81, wherein said antibody is attached to a cytotoxin selected from the group consisting of a Diphtheria toxin, a *Pseudomonas* exotoxin, a ricin, an abrin, saporin, and a thymidine kinase.

Embodiment 83: The immunoconjugate of embodiment 77, wherein said antibody is attached to a cytotoxic and/or cytostatic drug.

Embodiment 84: The immunoconjugate of embodiment 83, wherein said antibody is attached directly or through a linker to one or more of the following: said drug a lipid or liposome containing said drug; a polymeric drug carrier including said drug; and a nanoparticle drug carrier including said drug.

Embodiment 85: The immunoconjugate according to any one of embodiments 83-84, wherein said drug is an anticancer drug.

Embodiment 86: The immunoconjugate according to any one of embodiments 83-84, wherein said drug is selected from the group consisting of a tubulin inhibitor (e.g., auristatin, dolastatin, maytansine, colchicine, combretastatin, and the like), a DNA interacting agent (e.g., calicheamicins, duocarmycins, pyrrolobenzodiazepines (PBDs), and the like), and a pathway or enzyme inhibitor (e.g., mTOR/PI3K inhibitors, kinase and phosphatase inhibitors, RNA splicing inhibitors, RNA polymerase inhibitors, DNA polymerase inhibitors, topoisomerase inhibitors, ribosome inhibitors, proteosome inhibitors, and the like).

Embodiment 87: The immunoconjugate according to any one of embodiments 83-84, wherein said drug is selected from the group consisting of auristatin, dolastatin, colchicine, combretastatin, and mTOR/PI3K inhibitors.

Embodiment 88: The immunoconjugate according to any one of embodiments 83-84, wherein said drug an auristatin is selected from the group consisting of Auristatin E (AE), Monomethylauristatin E (MMAE), Auristatin F (MMAF), vcMMAE, and vcMMAF.

Embodiment 89: The immunoconjugate according to any one of embodiments 83-84, wherein said drug is monomethyl auristatin F.

Embodiment 90: The immunoconjugate of embodiment 89, wherein said auristatin F is conjugated to said antibody via a maleimidocaproyl-valine-citrulline-p-aminobenzyloxycarbonyl (MC-vcPAB) linker.

Embodiment 91: The immunoconjugate according to any one of embodiments 83-84, wherein said drug is selected from the group consisting of flourouracil (5-FU), capecitabine, 5-trifluoromethyl-2'-deoxyuridine, methotrexate sodium, raltitrexed, pemetrexed, cytosine Arabinoside, 6-mercaptopurine, azathioprine, 6-thioguanine (6-TG), pentostatin, fludarabine phosphate, cladribine, floxuridine (5-fluoro-2), ribonucleotide reductase inhibitor (RNR), cyclophosphamide, neosar, ifosfamide, thiotepa, 1,3-bis(2-chloroethyl)-1-nitosourea (BCNU), 1,-(2-chloroethyl)-3-cyclohexyl-lnitrosourea, methyl (CCNU), hexamethylmelamine, busulfan, procarbazine HCL, dacarbazine (DTIC), chlorambucil, melphalan, cisplatin, carboplatin, oxaliplatin, bendamustine, carmustine, chloromethine, dacarbazine (DTIC), fotemustine, lomustine, mannosulfan, nedaplatin, nimustine, prednimustine, ranimustine, satraplatin, semustine, streptozocin, temozolomide, treosulfan, triaziquone, triethylene melamine, thioTEPA, triplatin tetranitrate, trofosfamide, uramustine, doxorubicin, daunorubicin citrate, mitoxantrone, actinomycin D, etoposide, topotecan HCL, teniposide (VM-26), irinotecan HCL (CPT-11), camptothecin, belotecan, rubitecan, vincristine, vinblastine sulfate, vinorelbine tartrate, vindesine sulphate, paclitaxel, docetaxel, nanoparticle paclitaxel, abraxane, ixabepilone, larotaxel, ortataxel, tesetaxel, and vinflunine.

Embodiment 92: The immunoconjugate according to any one of embodiments 83-84, wherein said drug is selected from the group consisting of carboplatin, cisplatin, cyclophosphamide, docetaxel, doxorubicin, erlotinib, etoposide, gemcitabine, imatinib mesylate, irinotecan, methotrexate, sorafinib, sunitinib, topotecan, vinblastine, and vincristine.

Embodiment 93: The immunoconjugate according to any one of embodiments 83-84, wherein said drug is selected from the group consisting of retinoic acid, a retinoic acid derivative, doxirubicin, vinblastine, vincristine, cyclophosphamide, ifosfamide, cisplatin, 5-fluorouracil, a camptothecin derivative, interferon, tamoxifen, and taxol. In certain embodiments the anti-cancer compound is selected from the group consisting of abraxane, doxorubicin, pamidronate disodium, anastrozole, exemestane, cyclophosphamide, epirubicin, toremifene, letrozole, trastuzumab, megestroltamoxifen, paclitaxel, docetaxel, capecitabine, goserelin acetate, and zoledronic acid.

Embodiment 94: The immunoconjugate of embodiment 77, wherein said antibody is attached to a chelate including an isotope selected from the group consisting of $^{99}$Tc, $^{203}$Pb, $^{67}$Ga, $^{68}$Ga, $^{72}$As, $^{111}$In, $^{113}$In, $^{97}$Ru, $^{62}$Cu, $^{641}$Cu, $^{52}$Fe, $^{52}$Mn, $^{51}$Cr, $^{186}$Re, $^{188}$Re, $^{77}$As, $^{90}$Y, $^{67}$Cu, $^{169}$Er, $^{121}$Sn, $^{127}$Te, $^{142}$Pr, $^{143}$Pr, $^{198}$Au, $^{199}$Au, $^{161}$Tb, $^{109}$Pd, $^{165}$D, $^{149}$Pm, $^{151}$Pm, $^{153}$Sm, $^{157}$Gd, $^{159}$Gd, $^{166}$Ho, $^{172}$Tm, $^{169}$Yb, $^{175}$Yb, $^{177}$Lu, $^{105}$Rh and $^{111}$Ag.

Embodiment 95: The immunoconjugate of embodiment 77, wherein said antibody is attached to an alpha emitter.

Embodiment 96: The immunoconjugate of embodiment 95, wherein said alpha emitter is bismuth 213.

Embodiment 97: The immunoconjugate of embodiment 77, wherein said antibody is attached to a lipid or a liposome complexed with or containing an anti-cancer drug.

Embodiment 98: The immunoconjugate of embodiment 77, wherein said antibody is attached to a detectable label.

Embodiment 99: The immunoconjugate of embodiment 98, wherein said antibody is attached to a detectable label selected from the group consisting of a radioactive label, a radio-opaque label, an MRI label, and a PET label.

Embodiment 100: A pharmaceutical formulation said formulation including: a pharmaceutically acceptable excipient and an antibody according to any one of embodiments 33-76; and/or a pharmaceutically acceptable excipient and a immunoconjugate according to any one of embodiments 77-99.

Embodiment 101: The pharmaceutical formulation of embodiment 100, wherein said formulation is a unit dosage formulation.

Embodiment 102: The formulation according to any one of embodiments 100-101, wherein said formulation is formulated for administration via a route selected from the group consisting of oral administration, nasal administration, rectal administration, intraperitoneal injection, intravascular injection, subcutaneous injection, transcutaneous administration, and intramuscular injection.

Embodiment 103: A method of inhibiting the growth and/or proliferation of a cancer cell, said method including: contacting said cancer cell with an antibody according to any one of embodiments 33-76 and/or an immunoconjugate according to any one of embodiments 77-99.

Embodiment 104: The method of embodiment 103, wherein said cancer cell is a cancer cell in which macropinocytosis is upregulated.

Embodiment 105: The method according to any one of embodiments 103-104, wherein said cancer cell is a Ras-transformed cancer cell.

Embodiment 106: The method according to any one of embodiments 103-105, wherein said cancer cell is selected from the group consisting of ovarian cancer, breast cancer, lung cancer, prostate cancer, colon cancer, kidney cancer, pancreatic cancer, mesothelioma, lymphoma, liver cancer, urothelial cancer, melanoma, stomach cancer, and cervical cancer.

Embodiment 107: The method according to any one of embodiments 103-106, wherein said cell is a metastatic cell.

Embodiment 108: The method according to any one of embodiments 103-107, wherein said cell is a solid tumor cell.

Embodiment 109: The method according to any one of embodiments 103-108, wherein said antibody and/or immunoconjugate is administered in a pharmaceutical composition including a pharmaceutical acceptable carrier.

Embodiment 110: The method according to any one of embodiments 103-109, wherein said administering includes administering to a human.

Embodiment 111: The method according to any one of embodiments 103-109, wherein said administering includes administering to a non-human mammal.

Embodiment 112: The method according to any one of embodiments 103-111, wherein said administering includes administering parenterally.

Embodiment 113: The method according to any one of embodiments 103-111, wherein said administering includes administering into a tumor or a surgical site.

Embodiment 114: The method according to any one of embodiments 103-113, wherein said immunoconjugate is administered as an adjunct therapy to surgery and/or radiotherapy.

Embodiment 115: The method according to any one of embodiments 103-113, wherein said immunoconjugate is administered in conjunction with another anti-cancer drug and/or a hormone.

Embodiment 116: A method of detecting a cancer cell, said method including: contacting said cancer cell with a immunoconjugate of embodiment 99; and detecting the presence and/or location of said detectable label where the presence and/or location is an indicator of the location and/or presence of a prostate cancer cell.

Embodiment 117: The method of embodiment 116, wherein detecting includes a modality selected from the group consisting of said label includes a label selected from the group consisting of a x-ray, CAT scan, MRI, PET scan, and radioimaging.

Embodiment 118: The method of embodiment 116, wherein said detectable label is selected from the group consisting of a gamma-emitter, a positron-emitter, an x-ray emitter, an alpha emitter, and a fluorescence-emitter.

Embodiment 119: The method according to any one of embodiments 116-118, wherein said cancer cell is selected from the group consisting of ovarian cancer, breast cancer, lung cancer, prostate cancer, colon cancer, kidney cancer, pancreatic cancer, mesothelioma, lymphoma, liver cancer, urothelial cancer, stomach cancer, and cervical cancer.

Embodiment 120: The method according to any one of embodiments 116-119, wherein said contacting includes administering said immunoconjugate to a non-human mammal.

Embodiment 121: The method according to any one of embodiments 116-119, wherein said contacting includes administering said immunoconjugate to a human.

Embodiment 122: The method according to any one of embodiments 120-121, wherein said detecting includes detecting said label in vivo.

Embodiment 123: A nucleic acid encoding an antibody or a fragment (e.g., a binding fragment) of an antibody according to any of embodiments 33-76.

Embodiment 124: An expression vector comprising the nucleic acid of embodiment 123.

Embodiment 125: A cell containing the expression vector of embodiment 124.

Definitions

As used herein, an "antibody" refers to a protein consisting of one or more polypeptides substantially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD, and IgE, respectively.

A typical immunoglobulin (antibody) structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist as intact immunoglobulins or as a number of well characterized fragments produced by digestion with various peptidases. Thus, for example, pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region thereby converting the (Fab')$_2$ dimer into a Fab' monomer. The Fab' monomer is essentially a Fab with part of the hinge region (see, *Fundamental Immunology*, W. E. Paul, ed., Raven Press, N.Y. (1993), for a more detailed description of other antibody fragments). While various antibody fragments are defined in terms of the digestion of an intact antibody, one of skill will appreciate that such Fab' fragments may be synthesized de novo either chemically or by utilizing recombinant DNA methodology. Thus, the term antibody, as used herein also includes antibody fragments either produced by the modification of whole antibodies or synthesized de novo using recombinant DNA methodologies. Preferred antibodies include single chain antibodies (antibodies that exist as a single polypeptide chain), more preferably single chain Fv antibodies (sFv or scFv) in which a variable heavy and a variable light chain are joined together (directly or through a peptide linker) to form a continuous polypeptide. The single chain Fv antibody is a covalently linked $V_H$-$V_L$ heterodimer which may be expressed from a nucleic acid including $V_H$- and $V_L$-encoding sequences either joined directly or joined by a peptide-encoding linker. Huston, et al. (1988) *Proc. Nat. Acad. Sci. USA*, 85: 5879-5883. While the $V_H$ and $V_L$ are connected to each as a single polypeptide chain, the $V_H$ and $V_L$ domains associate non-covalently. The first functional antibody molecules to be expressed on the surface of filamentous phage were single-chain Fv's (scFv), however, alternative expression strategies have also been successful. For example Fab molecules can be displayed on phage if one of the chains (heavy or light) is fused to g3 capsid protein and the complementary chain exported to the periplasm as a soluble molecule. The two chains can be encoded on the same or on different replicons; the important point is that the two antibody chains in each Fab molecule assemble post-translationally and the dimer is incorporated into the phage particle via linkage of one of the chains to, e.g., g3p (see, e.g., U.S. Pat. No. 5,733,743). The scFv antibodies and a number of other structures converting the naturally aggregated, but chemically separated light and heavy polypeptide chains from an antibody V region into a molecule that folds into a three dimensional structure substantially similar to the structure of an antigen-binding site are known to those of skill in the art (see e.g., U.S. Pat. Nos. 5,091,513, 5,132,405, and 4,956,778). Particularly preferred antibodies should include all that have been displayed on phage (e.g., scFv, Fv, Fab and disulfide linked Fv (Reiter et al. (1995) *Protein Eng.* 8: 1323-1331).

The term "specifically binds", as used herein, when referring to a biomolecule (e.g., protein, nucleic acid, antibody, etc.), refers to a binding reaction that is determinative of the presence biomolecule in heterogeneous population of molecules (e.g., proteins and other biologics). Thus, under designated conditions (e.g. immunoassay conditions in the case of an antibody or stringent hybridization conditions in the case of a nucleic acid), the specified ligand or antibody binds to its particular "target" molecule and does not bind in a significant amount to other molecules present in the sample.

An "effector" refers to any molecule or combination of molecules whose activity it is desired to deliver/into and/or localize at cell. Effectors include, but are not limited to labels, cytotoxins, enzymes, growth factors, transcription factors, drugs, etc.

A "reporter" is an effector that provides a detectable signal (e.g. is a detectable label). In certain embodiments, the reporter need not provide the detectable signal itself, but can simply provide a moiety that subsequently can bind to a detectable label.

The term "conservative substitution" is used in reference to proteins or peptides to reflect amino acid substitutions that do not substantially alter the activity (specificity or binding affinity) of the molecule. Typically, conservative amino acid substitutions involve substitution of one amino acid for another amino acid with similar chemical properties (e.g. charge or hydrophobicity). The following six groups each contain amino acids that are typical conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W).

The terms "epitope tag" or "affinity tag" are used interchangeably herein, and used refers to a molecule or domain of a molecule that is specifically recognized by an antibody or other binding partner. The term also refers to the binding partner complex as well. Thus, for example, biotin or a biotin/avidin complex are both regarded as an affinity tag. In addition to epitopes recognized in epitope/antibody interactions, affinity tags also comprise "epitopes" recognized by other binding molecules (e.g. ligands bound by receptors), ligands bound by other ligands to form heterodimers or homodimers, His6 bound by Ni-NTA, biotin bound by avidin, streptavidin, or anti-biotin antibodies, and the like.

Epitope tags are well known to those of skill in the art. Moreover, antibodies specific to a wide variety of epitope tags are commercially available. These include but are not limited to antibodies against the DYKDDDDK (SEQ ID NO:1) epitope, c-myc antibodies (available from Sigma, St. Louis), the HNK-1 carbohydrate epitope, the HA epitope, the HSV epitope, the His4, His5, and His6 epitopes that are recognized by the His epitope specific antibodies (see, e.g., Qiagen), and the like. In addition, vectors for epitope tagging proteins are commercially available. Thus, for example, the pCMV-Tag1 vector is an epitope tagging vector designed for gene expression in mammalian cells. A target gene inserted into the pCMV-Tag1 vector can be tagged with the FLAG® epitope (N-terminal, C-terminal or internal tagging), the c-myc epitope (C-terminal) or both the FLAG (N-terminal) and c-myc (C-terminal) epitopes.

"High-content screening" (HCS) in cell-based systems is a method that typically uses living cells as to elucidate the workings of normal and diseased cells. High-content screening technology is mainly based on automated digital microscopy and, optionally, flow cytometry, typically in combination with IT-systems for the analysis and storage of the data. "High-content" or visual biology technology has two purposes, first to acquire spatially or temporally resolved information on an event and second to automatically quantify it. Spatially resolved instruments are typically automated microscopes, and temporal resolution still requires some form of fluorescence measurement in most cases. This means that many HCS instruments are (fluorescence) microscopes that are connected to some form of image analysis package. These take care of all the steps in taking fluorescent images of cells and provide rapid, automated and unbiased assessment of experiments.

BRIEF DESCRIPTION OF THE DRAWINGS

FIG. 1. Amino acid sequences of VH domains of HCA-F1 (SEQ ID NO:2), HCA-F2 (SEQ ID NO:3), HCA-M1 (SEQ ID NO:4), and HCA-S1 (SEQ ID NO:5) antibodies and amino acid sequences of VL domains of HCA-F1 (SEQ ID NO:6), HCA-F2 (SEQ ID NO:7), HCA-M1 (SEQ ID NO:8), and HCA-S1 (SEQ ID NO:9) antibodies.

FIG. 2A) Schematic of HCA screening to identify macropinocytosis-dependent antibodies. HCA instruments allow automated high throughput detection of antibody colocalization with a macropinocytosis marker. The starting materials for the screening are sublibraries generated previously by us from LCM-based phage antibody library selection [1] that are enriched for internalizing phage antibodies binding to tumor cells in situ. FIG. 2B) DU145 cells were incubated in 96-well plates with phage-containing supernatants for 24 hours at 37° C. in complete DMEM/10% FBS. Nuclei were stained with Hoechst 33342. Bound phages were immunolabeled with anti-Fd antibodies (green). Zoomed insert portrays software-based, automated cell analysis, measuring mean fluorescence intensities (MFI) of immunolabeled phages. Over 300 cells were quantified for each phage clone. FIG. 2C) Plot of MFI values of immunolabeled phage binding to cell for 1,439 phage clones. Red horizontal line represents MFI of ~250,000, the threshold for prioritizing clones for further internalization analysis.

DETAILED DESCRIPTION

In various embodiments, methods are provided for identifying and selecting antibodies that are internalized into cells via the macropinocytosis pathway. Additionally antibodies that are internalized via this pathway are provided as well as immunoconjugates comprising such antibodies.
Methods of Identifying Antibodies Internalized by the Macropinocytosis Pathway.

In various embodiments, methods of preparing antibodies that are internalized into a cell by a macropinocytosis pathway are provided. In one illustrative, but non-limiting embodiment, the method involves contacting target cells with members of an antibody library and with marker(s) for macropinocytosis; identifying internalized antibodies that co-localize in the target cells with the marker(s) for macropinocytosis; and selecting those antibodies that co-localize with the marker(s) for macropinocytosis. In various embodiments, the members of an antibody library are members of a phage display library or members of a yeast display library. In certain embodiments the antibody library is an antibody library that is enriched for antibodies that bind to tumor cells and said enrichment is by laser capture microdissection (LCM) of antibodies that bind to tumor cells (e.g., as described in Ruan et al. (2006)*Mol. Cell Proteomics.* 5: 2364-2373, and in U.S. Ser. No. 12/724,282 and PCT/US2008/076704 which are incorporated herein by reference for the LCM enrichment methods described therein). In certain embodiments, the methods involve selecting internalized antibodies that colocalize with a lysosomal marker (e.g., LAMP1). As described herein and illustrated in the examples, the method is facilitated by the use of high content analysis (HCA) using digital microscopy and a data acquisition system.

Figure 2A:
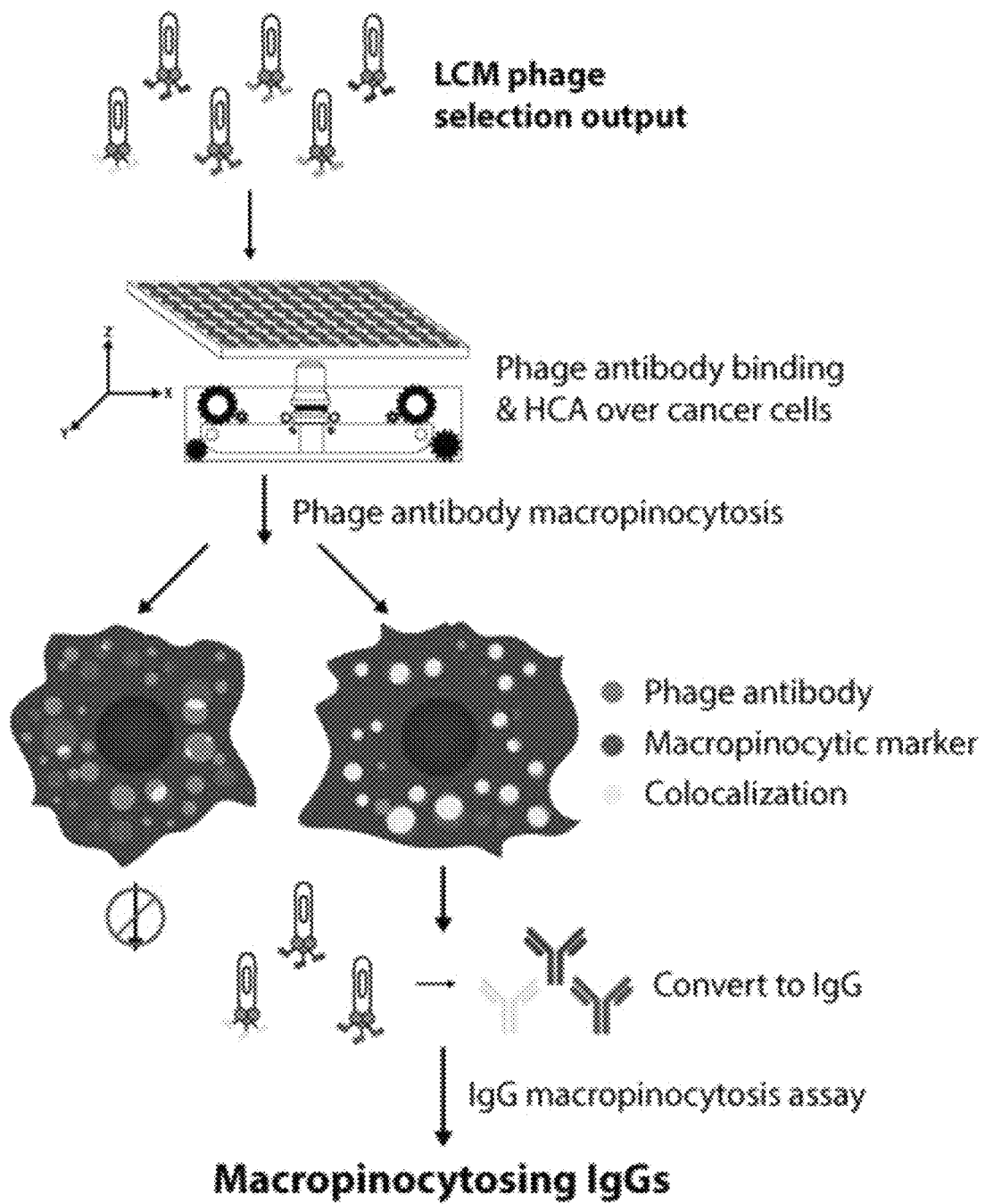
FIGS. 2A-2C. Outline of screening strategy and data from the first step of the screening, i.e., phage binding to DU145 cells.

One illustrative, but non-limiting embodiment of the HCA-based strategy that used to identify antibodies capable of internalizing into tumor cells via macropinocytosis is outlined in FIG. 2A. An HCA platform was developed that allows quantitative measurement of colocalization between phage antibodies and a macropinocytic marker (e.g., ND70-TR, FITC-dextran, latex or glass beads, Lucifer yellow, etc.). To identify clinically relevant macropinocytosing antibodies, we screened phage antibody libraries that we have generated previously by laser capture microdissection (LCM)-based selection, which are highly enriched for internalizing antibodies that bind to prostate tumor cells in situ residing in the tumor tissue microenvironment [1]. More particularly, the HCA protocol was used to screen single chain variable fragment (scFv) phage antibody display libraries that were previously generated by laser capture microdissection (LCM)-based selection on live tumor cells and tumor tissues, which are highly enriched for internalizing phage antibodies binding to prostate tumor cells in situ residing in their tissue microenvironment [1], and identified antibodies that are capable of efficient internalization via macropinocytosis.

Antibodies Internalized by the Macropinocytosis Pathway.

In certain embodiments antibodies that are internalized into cells by the macropinocytosis pathway are provided. The antibodies were identified by selecting human antibody gene diversity libraries directly on the surface of prostate cancer cells in vivo using laser microdissection methods as described above and in the examples. Antibodies were identified that specifically bind and enter prostate cancer cells, with little or no binding to control cells.

For the selection process, the antibodies in the library were expressed as single chain Fv (scFv) antibodies comprising a variable heavy ($V_H$) region linked to a variable light ($V_L$) region by a peptide linker, although it will be recognized that using the antibody sequence presented herein other forms of the antibodies can be provided.

Representative antibodies (e.g. VH and VL domains) are illustrated in Table 1 and FIG. 1.

TABLE 1

Amino acid sequences of VL and VH domains of HCA-F1 and HCA-F2 antibodies internalized by the macropinocytosis pathway. HCA-M1 is internalized at a moderate rate while HCA-S1 is slowly internalized in contrast to the macropinocytosing antibodies (HCA-F1 and HCA-F2). HCA-M1 and HCA-S1 do not bind to EphA2, but they are useful for other applications where non-internalizing antibodies are desired (such as bispecific mAbs for T cell capture etc.).

| Clone | Frame 1 | CDR1 | Frame 2 | CDR2 | Frame 3 | CDR3 | Frame 4 |
|---|---|---|---|---|---|---|---|
| Heavy chain | | | | | | | |
| HCA-F1 SEQ ID NO: 2 | QVQLQE SGGGLV QPGGSL RLSCAA SGFTFS | SYSM N SEQ ID NO: 38 | WVRQAYISS PGKGLSSST EWVS IYYA | RFTISR DNAKNS LYLQMN DSVKG SEQ ID NO: 39 | YRL PDF WSG SLRAED TAVYYC AR | WGQGTT VTVSS YPN YGM DV SEQ ID NO: 40 | |
| HCA-F2 SEQ ID NO: 3 | QVQLVE SGGGLV QPGGSL RLSCAA SGFTFS | SYAMS SEQ ID NO: 41 | WVRQAAISG PGKGLSGGS EWVS TYYA | RFTISR DNSKNT LYLQMN DSVKG SEQ ID NO: 42 | LSV EWY GSG SLRAED TAVYYC AT | WGQGTL VTVSS GSY SYL GY SEQ ID NO: 43 | |
| HCA-M1 SEQ ID NO: 4 | QVQLVE SGGGVV QPGRSL RLSCAA SGFTFS | SYAMH SEQ ID NO: 44 | WVRQAVISY PGKGLDGSN EWVA KYYA | RFTISR DNSKNT LYLQMN DSVKG SEQ ID NO: 45 | APA YSY GPF SLRAED TAVYYC AR | WGQGTL VTVSS SEQ ID NO: 46 | |
| HCA-S1 SEQ ID NO: 5 | QVQLQE SGGGLV QPGGSL RLSCAA SGFTFS | SYAM H NO: 44 | WVRQAVISY PGKGLDGSN EWVA KYYA | RFTISR DNSKNT LYLQMN DSVK G SEQ ID NO: 45 | FSS GWY YFDY SLRAED TAVYY AR | WGQGTL VTVSS SEQ ID NO: 47 | |
| Light chain | | | | | | | |
| HCA-F1 SEQ ID NO: 6 | QSVLTQ PPSVSG APGQRV TISC | TGSS SNIG AGYD VH SEQ ID NO: 48 | WYQQLYGNS PGTAPNRPS KLLI SEQ ID NO: 49 | GVPDRF SGSKSG TSASLA ITGLQA EDEADY YC | QSY DSS LSG HVV SEQ ID NO: 50 | FGGGTK LTVL | |
| HCA-F2 SEQ ID NO: 7 | NFMLTQ DPAVSV ALGQTV RITC | QGDS LRSY YAS SEQ ID NO: 51 | WYQQKYGKN PGQAPNRPS VLVI SEQ ID NO: 52 | GIPDRF SGSSSG NTASLT ITGAQA EDEAHY YC | NSR DSS ANH VV | FGGGTK VTVL SEQ ID NO: 53 | |
| HCA-M1 SEQ ID NO: 8 | SSELTQ DPAVSV ALGQTV RITC | QGDS LRSY YAS SEQ ID NO: 51 | WYQQKYGKN PGQAPNRPS VLVI SEQ ID NO: 52 | GIPDRF SGSSSG NTASLT ITGAQA EDEADY YC | HSR DSS GTH LRV SEQ ID NO: 54 | FGGGTK VTVL | |
| HCA-S1 SEQ ID NO: 9 | DIQMTQ SPSFLS ASVGDR ITITC | RASH DISS YFA SEQ ID NO: 55 | WYQQKYAAS PGKAPTLQA KPLI SEQ ID NO: 56 | GVPSRF SGSGSG TEFTLT ISSLQP EDFATY YC | QQL GSY PLT SEQ ID NO: 57 | FGGGTK LEIK | |

In certain embodiments, for single chain Fv antibodies the variable heavy (VH) region is coupled to the variable light ($V_L$) either directly, or more preferably by a peptide linker (e.g., $(Gly_4Ser)_3$, SEQ ID NO:10).

Using the sequence information provided in Table 1 and/or FIG. 1, antibodies macropinocytosing antibodies HCA-F1, and HCA-F2, or HCA-M1, and HCA-S1, or antibodies comprising one or more of the CDRs comprising these antibodies, or antibodies comprising the VH and/or VL domain(s) of these antibodies can readily be prepared using standard methods (e.g. chemical synthesis methods and/or recombinant expression methods) well known to those of skill in the art.

In addition, other "related" antibodies that are internalized by the macropinocytosis pathway can be identified by screening for antibodies that bind to the same epitope (e.g. that compete with the listed antibodies for binding to ephrin type-A receptor 2 (EphA2) and/or by modification of the antibodies identified herein to produce libraries of modified antibody and then rescreening antibodies in the library for improved internalization by the macropinocytosis pathway, and/or by screening of various libraries on cancer cells, e.g., as illustrated in Example 1.

A) Chemical Synthesis.

Using the sequence information provided herein, the antibodies internalized by the macropinocytosis pathway (e.g., HCA-F1, HCA-F2, etc.), or variants thereof, can be chemically synthesized using well known methods of peptide synthesis. Solid phase synthesis in which the C-terminal amino acid of the sequence is attached to an insoluble support followed by sequential addition of the remaining amino acids in the sequence is one preferred method for the chemical synthesis of single chain antibodies. Techniques for solid phase synthesis are described by Barany and Merrifield, *Solid Phase Peptide Synthesis;* pp. 3-284 in *The Peptides: Analysis, Synthesis, Biology.* Vol. 2: *Special Methods in Peptide Synthesis*, Part A., Merrifield et al. (1963) *J. Am. Chem. Soc.*, 85: 2149-2156, and Stewart et al. (1984) *Solid Phase Peptide Synthesis*, 2nd ed. Pierce Chem. Co., Rockford, Ill.

B) Recombinant Expression of Prostate Cancer-Specific Antibodies.

In certain preferred embodiments, the antibodies internalized by the macropinocytosis pathway (e.g., HCA-F1, HCA-F2, etc.), or variants thereof, are prepared using standard techniques well known to those of skill in the art. Using the sequence information provided herein, nucleic acids encoding the desired antibody can be chemically synthesized according to a number of standard methods known to those of skill in the art. Oligonucleotide synthesis, is preferably carried out on commercially available solid phase oligonucleotide synthesis machines (Needham-VanDevanter et al. (1984) *Nucleic Acids Res.* 12: 6159-6168) or manually synthesized using the solid phase phosphoramidite triester method described by Beaucage et. al. (1981) *Tetrahedron Letts.* 22(20): 1859-1862. Alternatively, nucleic acids encoding the antibody can be amplified and/or cloned according to standard methods.

Molecular cloning techniques to achieve these ends are known in the art. A wide variety of cloning and in vitro amplification methods are suitable for the construction of recombinant nucleic acids. Examples of these techniques and instructions sufficient to direct persons of skill through many cloning exercises are found in Berger and Kimmel, *Guide to Molecular Cloning Techniques, Methods in Enzymology* volume 152 Academic Press, Inc., San Diego, Calif. (Berger); Sambrook et al. (1989) *Molecular Cloning—A Laboratory Manual* (2nd ed.) Vol. 1-3, Cold Spring Harbor Laboratory, Cold Spring Harbor Press, NY, (Sambrook); and *Current Protocols in Molecular Biology*, F. M. Ausubel et al., eds., Current Protocols, a joint venture between Greene Publishing Associates, Inc. and John Wiley & Sons, Inc., (1994 Supplement) (Ausubel). Methods of producing recombinant immunoglobulins are also known in the art. See, Cabilly, U.S. Pat. No. 4,816,567; and Queen et al. (1989) *Proc. Natl Acad. Sci. USA* 86: 10029-10033. In addition, detailed protocols for the expression of antibodies are also provided by Liu et al. (2004) *Cancer Res.* 64: 704-710, Poul et al. (2000) *J. Mol. Biol.* 301: 1149-1161, and the like.

C) Identification of Other Antibodies Binding the Same Target as Antibodies HCA-F1, HCA-F2, HCA-M1, and/or HCA-S1.

Having identified useful antibodies internalized by the macropinocytosis pathway (e.g., HCA-F1, HCA-F2), other "related" antibodies internalized by the macropinocytosis pathway can be identified by screening for antibodies that cross-react with the identified antibodies, e.g., at ephrin type-A receptor 2 (EphA2) or at the epitope of EphA2 bound by HCA-F1, HCA-F2, HCA-M1, and/or HCA-S1 and/or with an idiotypic antibody raised against HCA-F1, HCA-F2, HCA-M1, and/or HCA-S1 antibody.

1) Cross-Reactivity with Anti-Idiotypic Antibodies.

The idiotype represents the highly variable antigen-binding site of an antibody and is itself immunogenic. During the generation of an antibody-mediated immune response, an individual will develop antibodies to the antigen as well as anti-idiotype antibodies, whose immunogenic binding site (idiotype) mimics the antigen.

Anti-idiotypic antibodies can be raised against the variable regions of the antibodies identified herein using standard methods well known to those of skill in the art. Briefly, anti-idiotype antibodies can be made by injecting the antibodies of this invention, or fragments thereof (e.g., CDRs) into an animal thereby eliciting antisera against various antigenic determinants on the antibody, including determinants in the idiotypic region.

Methods for the production of anti-analyte antibodies are well known in the art. Large molecular weight antigens (greater than approx. 5000 Daltons) can be injected directly into animals, whereas small molecular weight compounds (less than approx. 5000 Daltons) are preferably coupled to a high molecular weight immunogenic carrier, usually a protein, to render them immunogenic. The antibodies produced in response to immunization can be utilized as serum, ascites fluid, an immunoglobulin (Ig) fraction, an IgG fraction, or as affinity-purified monospecific material.

Polyclonal anti-idiotype antibodies can be prepared by immunizing an animal with the antibodies of this invention prepared as described above. In general, it is desirable to immunize an animal which is species and allotype-matched with the animal from which the antibody (e.g. phage-display library) was derived. This minimizes the production of antibodies directed against non-idiotypic determinants. The antiserum so obtained is then usually absorbed extensively against normal serum from the same species from which the phage-display library was derived, thereby eliminating antibodies directed against non-idiotypic determinants. Absorption can be accomplished by passing antiserum over a gel formed by crosslinking normal (nonimmune) serum proteins with glutaraldehyde. Antibodies with anti-idiotypic specificity will pass directly through the gel, while those having specificity for non-idiotypic determinants will bind to the gel. Immobilizing nonimmune serum proteins on an insoluble polysaccharide support (e.g., sepharose) also provides a suitable matrix for absorption.

Monoclonal anti-idiotype antibodies can be produced using the method of Kohler et al. (1975) *Nature* 256: 495. In particular, monoclonal anti-idiotype antibodies can be prepared using hybridoma technology which comprises fusing (1) spleen cells from a mouse immunized with the antigen or hapten-carrier conjugate of interest (i.e., the antibodies or this invention or subsequences thereof) to (2) a mouse myeloma cell line which has been selected for resistance to a drug (e.g., 8-azaguanine). In general, it is desirable to use a myeloma cell line which does not secrete an immunoglobulin. Several such lines are known in the art. One generally preferred cell line is P3X63Ag8.653. This cell line is on deposit at the American Type Culture Collection as CRL-1580.

Fusion can be carried out in the presence of polyethylene glycol according to established methods (see, e.g., *Monoclonal Antibodies*, R. Kennett, J. McKearn & K. Bechtol, eds. N.Y., Plenum Press, 1980, and *Current Topics in Microbiology & Immunology, Vol.* 81, F. Melchers, M. Potter & N. L. Warner, eds., N.Y., Springer-Verlag, 1978). The resultant mixture of fused and unfused cells is plated out in hypoxanthine-aminopterin-thymidine (HAT) selective medium. Under these conditions, only hybrid cells will grow.

When sufficient cell growth has occurred, (typically 10-14 days post-fusion), the culture medium is harvested and screened for the presence of monoclonal idiotypic, anti-analyte antibody by any one of a number of methods which include solid phase RIA and enzyme-linked immunosorbent assay. Cells from culture wells containing antibody of the desired specificity are then expanded and recloned. Cells from those cultures that remain positive for the antibody of interest are then usually passed as ascites tumors in susceptible, histocompatible, pristane-primed mice.

Ascites fluid is harvested by tapping the peritoneal cavity, retested for antibody, and purified as described above. If a nonsecreting myeloma line is used in the fusion, affinity purification of the monoclonal antibody is not usually necessary since the antibody is already homogeneous with respect to its antigen-binding characteristics. All that is necessary is to isolate it from contaminating proteins in ascites, i.e., to produce an immunoglobulin fraction.

Alternatively, the hybrid cell lines of interest can be grown in serum-free tissue culture and the antibody harvested from the culture medium. In general, this is a less desirable method of obtaining large quantities of antibody because the yield is low. It is also possible to pass the cells intravenously in mice and to harvest the antibody from serum. This method is generally not preferred because of the small quantity of serum which can be obtained per bleed and because of the need for extensive purification from other serum components. However, some hybridomas will not grow as ascites tumors and therefore one of these alternative methods of obtaining antibody must be used.

2) Cross-reactivity with the HCA-F1, HCA-F2, HCA-M1, and/or HCA-S1 antibodies.

In another approach, other antibodies internalized by the macropinocytosis pathway can be identified by the fact that they bind ephrin type-A receptor 2 (EphA2) or at the epitope of EphA2 bound by "prototypic" antibodies described herein (e.g., HCA-F1, HCA-F2, etc.).

Methods of determining antibody cross-reactivity are well known to those of skill in the art. Generally the epitope bound by the prototypic antibodies of this invention is determined e.g. by epitope mapping techniques. Methods of epitope mapping are well known to those of skill in the art (see, e.g., Reyes et al. (1992) *Hepatitis E Virus (HEV): Epitope Mapping and Detection of Strain Variation*, Elsevier Science Publisher Shikata et al. eds., Chapter 43:237-245; Li et al. (1993) *Nature* 363: 85-88). Epitope mapping can be performed using Novatope system, a kit for which is commercially available from Novagen, Inc.

In certain embodiments, cross-reactive antibodies internalized by the macropinocytosis pathway show at least 60%, preferably 80%, more preferably 90%, and most preferably at least 95% or at least 99% cross-reactivity with one or more of HCA-F1, HCA-F2, HCA-M1, and/or HCA-S1.

D) Phage Display Methods to Select Other "Related" Antibodies Internalized by the Macropinocytosis Pathway.

1) Chain Shuffling Methods.

One approach to creating modified single-chain antibody (scFv) gene repertoires has been to replace the original $V_H$ or $V_L$ gene with a repertoire of V-genes to create new partners (chain shuffling) (Clackson et al. (1991) *Nature*. 352: 624-628). Using chain shuffling and phage display (or yeast display) as well as the screening/selection method described above for identifying antibodies internalized by the macropinocytosis pathway, other suitable internalizing antibodies can readily be identified.

Thus, for example a mutant scFv gene repertoire can be created containing a $V_H$ gene of the prototypic antibodies (e.g. as shown in Table 1 and/or FIG. 1) antibody and a human $V_L$ gene repertoire (light chain shuffling). The scFv gene repertoire can be cloned into a phage display vector, e.g., pHEN-1 (Hoogenboom et al. (1991) *Nucleic Acids Res.*, 19: 4133-4137) or other vectors, and after transformation a library of transformants is obtained.

Similarly, for heavy chain shuffling, the antibodies internalized by the macropinocytosis pathway (e.g., HCA-F1, HCA-F2, HCA-M1, and/or HCA-S1, etc.) VH CDR1 and/or CDR2, and/or CDR3 and light chain (see, e.g., Table 1) are cloned into a vector containing a human VH gene repertoire to create a phage antibody library transformants. For detailed descriptions of chain shuffling to increase antibody affinity see, e.g., Schier et al. (1996) *J. Mol. Biol.*, 255: 28-43, and the like.

2) Site-Directed Mutagenesis to Improve Binding Affinity.

The majority of antigen contacting amino acid side chains are typically located in the complementarity determining regions (CDRs), three in the $V_H$ (CDR1, CDR2, and CDR3) and three in the $V_L$ (CDR1, CDR2, and CDR3) (Chothia et al. (1987) *J. Mol. Biol.*, 196: 901-917; Chothia et al. (1986) *Science*, 233: 755-8; Nhan et al. (1991) *J. Mol. Biol.*, 217: 133-151). These residues contribute the majority of binding energetics responsible for antibody affinity for antigen. In other molecules, mutating amino acids which contact ligand has been shown to be an effective means of increasing the affinity of one protein molecule for its binding partner (Lowman et al. (1993) *J. Mol. Biol.*, 234: 564-578; Wells (1990) *Biochemistry*, 29: 8509-8516). Site-directed mutagenesis of CDRs of the antibodies described herein and screening for internalization via the macropinocytosis pathway as described herein can produce additional suitable antibodies.

3) CDR Randomization to Produce Higher Affinity Human scFv.

In an extension of simple site-directed mutagenesis, mutant antibody libraries can be created where partial or entire CDRs are randomized ($V_L$ CDR1 CDR2 and/or CDR3 and/or $V_H$ CDR1, CDR2 and/or CDR3). In one embodiment, each CDR is randomized in a separate library, using a known antibody (e.g., HCA-F1, HCA-F2, HCA-M1, and/or HCA-S1) as a template. The CDR sequences of the best internalizing mutants from each CDR library can be combined to obtain additional antibodies.

$V_H$ CDR3 often occupies the center of the binding pocket, and thus mutations in this region are likely to result in an increase in affinity (Clackson et al. (1995) *Science*, 267: 383-386). In one embodiment, four $V_H$ CDR3 residues are randomized at a time (see, e.g., Schier et al. (1996) *Gene*, 169: 147-155; Schier and Marks (1996) *Human Antibodies and Hybridomas.* 7: 97-105, 1996; and Schier et al. (1996) *J Mol. Biol.* 263: 551-567).

E) Creation of Other Antibody Forms.

Using the known and/or identified sequences (e.g. $V_H$ and/or $V_L$ sequences) of the HCA-F1, HCA-F2, HCA-M1, and/or HCA-S1 antibodeies shown in Table 1 other antibody forms can readily be created. Such forms include, but are not limited to multivalent antibodies, full antibodies (e.g., IgG, IgA, IgM), scFv, (scFv')$_2$, Fab, (Fab')$_2$, chimeric antibodies, and the like.

1) Creation of Homodimers.

For example, to create (scFv')$_2$ antibodies, two scFV antibodies internalized by the macropinocytosis pathway are joined, either through a linker (e.g., a carbon linker, a peptide, etc.) or through a disulfide bond between, for example, two cysteines. Thus, for example, to create disulfide linked scFv, a cysteine residue can be introduced by site directed mutagenesis at the carboxy-terminus of the antibodies described herein.

An scFv can be expressed from this construct, purified by IMAC, and analyzed by gel filtration. To produce (scFv')$_2$ dimers, the cysteine is reduced by incubation with 1 mM 3-mercaptoethanol, and half of the scFv blocked by the addition of DTNB. Blocked and unblocked scFvs are incubated together to form (scFv')$_2$ and the resulting material can be analyzed by gel filtration. The affinity of the resulting dimmer can be determined using standard methods, e.g. by BIAcore.

In one illustrative embodiment, the (scFv')$_2$ dimer is created by joining the scFv' fragments through a linker, more preferably through a peptide linker. This can be accomplished by a wide variety of means well known to those of skill in the art. For example, one preferred approach is described by Holliger et al. (1993) *Proc. Natl. Acad. Sci. USA*, 90: 6444-6448 (see also WO 94/13804).

It is noted that using the $V_H$ and/or $V_L$ sequences provided herein Fabs and (Fab')$_2$ dimers can also readily be prepared. Fab is a light chain joined to $V_H$-$C_H$1 by a disulfide bond and can readily be created using standard methods known to those of skill in the art. The F(ab)'$_2$ can be produced by dimerizing the Fab, e.g. as described above for the (scFv')$_2$ dimer.

2) Chimeric Antibodies.

The antibodies contemplated herein also include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see, e.g., U.S. Pat. No. 4,816,567; Morrison et al. (1984) *Proc. Natl. Acad. Sci.* 81: 6851-6855, etc.).

While the prototypic antibodies provided herein are fully human antibodies, chimeric antibodies are contemplated, particularly when such antibodies are to be used in species other than humans (e.g., in veterinary applications). Chimeric antibodies are antibodies comprising a portions from two different species (e.g. a human and non-human portion). Typically, the antigen combining region (or variable region) of a chimeric antibody is derived from a one species source and the constant region of the chimeric antibody (which confers biological effector function to the immunoglobulin) is derived from another source. A large number of methods of generating chimeric antibodies are well known to those of skill in the art (see, e.g., U.S. Pat. Nos. 5,502,167, 5,500,362, 5,491,088, 5,482,856, 5,472,693, 5,354,847, 5,292,867, 5,231,026, 5,204,244, 5,202,238, 5,169,939, 5,081,235, 5,075,431, and 4,975,369, and PCT application WO 91/0996).

In general, the procedures used to produce chimeric antibodies consist of the following steps (the order of some steps may be interchanged): (a) identifying and cloning the correct gene segment encoding the antigen binding portion of the antibody molecule; this gene segment (known as the VDJ, variable, diversity and joining regions for heavy chains or VJ, variable, joining regions for light chains, or simply as the V or variable region or $V_H$ and $V_L$ regions) may be in either the cDNA or genomic form; (b) cloning the gene segments encoding the human constant region or desired part thereof; (c) ligating the variable region to the constant region so that the complete chimeric antibody is encoded in a transcribable and translatable form; (d) ligating this construct into a vector containing a selectable marker and gene control regions such as promoters, enhancers and poly(A) addition signals; (e) amplifying this construct in a host cell (e.g., bacteria); (f) introducing the DNA into eukaryotic cells (transfection) most often mammalian lymphocytes; and culturing the host cell under conditions suitable for expression of the chimeric antibody.

Antibodies of several distinct antigen binding specificities have been manipulated by these protocols to produce chimeric proteins (e.g., anti-TNP: Boulianne et al. (1984) *Nature*, 312: 643; and anti-tumor antigens: Sahagan et al. (1986) *J. Immunol.*, 137: 1066). Likewise several different effector functions have been achieved by linking new sequences to those encoding the antigen binding region. Some of these include enzymes (Neuberger et al. (1984) *Nature* 312: 604), immunoglobulin constant regions from another species and constant regions of another immunoglobulin chain (Sharon et al. (1984) *Nature* 309: 364; Tan et al., (1985) *J. Immunol.* 135: 3565-3567).

In certain embodiments, a recombinant DNA vector is used to transfect a cell line to produce a cell that expresses antibodies internalized by the macropinocytosis pathway. The novel recombinant DNA vector contains a "replacement gene" to replace all or a portion of the gene encoding the immunoglobulin constant region in the cell line (e.g., a replacement gene may encode all or a portion of a constant region of a human immunoglobulin, a specific immunoglobulin class, or an enzyme, a toxin, a biologically active peptide, a growth factor, inhibitor, or a linker peptide to facilitate conjugation to a drug, toxin, or other molecule, etc.), and a "target sequence" that allows for targeted homologous recombination with immunoglobulin sequences within the antibody producing cell.

In another embodiment, a recombinant DNA vector is used to transfect a cell line that produces an antibody having a desired effector function, (e.g., a constant region of a human immunoglobulin) in which case, the replacement gene contained in the recombinant vector may encode all or a portion of a region of an antibodies internalized by the macropinocytosis pathway and the target sequence contained in the recombinant vector allows for homologous recombination and targeted gene modification within the antibody producing cell. In either embodiment, when only a portion of the variable or constant region is replaced, the resulting chimeric antibody can define the same antigen and/or have the same effector function yet be altered or improved so that the chimeric antibody may demonstrate a greater antigen specificity, greater affinity binding constant, increased effector function, or increased secretion and production by the transfected antibody producing cell line, etc.

Regardless of the embodiment practiced, the processes of selection for integrated DNA (via a selectable marker), screening for chimeric antibody production, and cell cloning, can be used to obtain a clone of cells producing the chimeric antibody.

Thus, a piece of DNA that encodes a modification for a monoclonal antibody can be targeted directly to the site of the expressed immunoglobulin gene within a B-cell or hybridoma cell line. DNA constructs for any particular modification can be made to alter the protein product of any monoclonal cell line or hybridoma. The level of expression of chimeric antibody should be higher when the gene is at its natural chromosomal location rather than at a random position. Detailed methods for preparation of chimeric (humanized) antibodies can be found in U.S. Pat. No. 5,482,856.

3) Intact Human Antibodies.

In another embodiment, this invention provides for intact, fully human antibodies internalized by the macropinocytosis pathway. Such antibodies can readily be produced in a manner analogous to making chimeric human antibodies. In this instance, instead of using a recognition function derived, e.g. from a murine, the fully human recognition function (e.g., VH and $V_L$) of the antibodies described herein is utilized.

4) Diabodies.

In certain embodiments, diabodies comprising one or more of the $V_H$ and $V_L$ domains described herein are contemplated. The term "diabodies" refers to antibody fragments typically having two antigen-binding sites. The fragments typically comprise a heavy chain variable domain ($V_H$) connected to a light chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161, and Holliger et al. (1993) *Proc. Nat. Acad. Sci. USA* 90: 6444-6448.

5) Unibodies.

In certain embodiments using the sequence information provided herein, the antibodies described herein can be constructed as unibodies. UniBody antibody technology produces a stable, smaller antibody format with an anticipated longer therapeutic window than certain small antibody formats. In certain embodiments unibodies are produced from IgG4 antibodies by eliminating the hinge region of the antibody. Unlike the full size IgG4 antibody, the half molecule fragment is very stable and is termed a uniBody. Halving the IgG4 molecule leaves only one area on the UniBody that can bind to a target. Methods of producing unibodies are described in detail in PCT Publication WO2007/059782, which is incorporated herein by reference in its entirety (see, also, Kolfschoten et al. (2007) *Science* 317: 1554-1557).

6) Affibodies.

In certain embodiments the sequence information provided herein is used to construct affibody molecules are internalized by the macropinocytosis pathway. Affibody molecules are class of affinity proteins based on a 58-amino acid residue protein domain, derived from one of the IgG-binding domains of staphylococcal protein A. This three helix bundle domain has been used as a scaffold for the construction of combinatorial phagemid libraries, from which affibody variants that target the desired molecules can be selected using phage display technology (see, e.g., Nord et al. (1997) *Nat. Biotechnol.* 15: 772-777; Ronmark et al. (2002) *Eur. J. Biochem.*, 269: 2647-2655.). Details of Affibodies and methods of production are known to those of skill (see, e.g., U.S. Pat. No. 5,831,012 which is incorporated herein by reference in its entirety).

It will be recognized that the antibodies described above can be provided as whole intact antibodies (e.g., IgG), antibody fragments, or single chain antibodies, using methods well known to those of skill in the art. In addition, while the antibody can be from essentially any mammalian species, to reduce immunogenicity, it is desirable to use an antibody that is of the species in which the antibody and/or chimeric moiety is to be used. In other words, for use in a human, it is desirable to use a human, humanized, or chimeric human antibody.

Immunoconjugates Comprising Antibodies that are Internalized by the Macropinocytosis Pathway The antibodies described herein that are internalized via a macropinocytosis pathway (e.g., HCA-F1, HCA-F2, etc.) can be used alone as therapeutics (e.g., to inhibit growth and/or proliferation of a prostate cancer cell) or they can be coupled to an effector forming immunoconjugates that provide efficient and specific delivery of the effector (e.g. cytotoxins, labels, radionuclides, ligands, antibodies, drugs, liposomes, nanoparticles, viral particles, cytokines, and the like) into cancer cells, particularly cancer cells where the macropinocytosis pathway is upregulated (e.g., ras-transformed cancer cells).

Immunoconjugates can be formed by conjugating the antibodies or antigen binding portions thereof described herein to an effector (e.g., a detectable label, another therapeutic agent, etc.). Suitable agents include, for example, a cytotoxic or cytostatic agent (e.g., a chemotherapeutic agent), a toxin (e.g. an enzymatically active toxin of bacterial, fungal, plant or animal origin, or fragments thereof), and/or a radioactive isotope (i.e., a radioconjugate).

In certain embodiments, the effector comprises a detectable label. Suitable detectable labels include, but are not limited to radio-opaque labels, nanoparticles, PET labels, MRI labels, radioactive labels, and the like. Among the radionuclides and useful in various embodiments of the present invention, gamma-emitters, positron-emitters, x-ray emitters and fluorescence-emitters are suitable for localization, diagnosis and/or staging, and/or therapy, while beta and alpha-emitters and electron and neutron-capturing agents, such as boron and uranium, also can be used for therapy.

The detectable labels can be used in conjunction with an external detector and/or an internal detector and provide a means of effectively localizing and/or visualizing prostate cancer cells. Such detection/visualization can be useful in various contexts including, but not limited to pre-operative and intraoperative settings. Thus, in certain embodiment this invention relates to a method of intraoperatively detecting and prostate cancers in the body of a mammal. These methods typically involve administering to the mammal a composition comprising, in a quantity sufficient for detection by a detector (e.g. a gamma detecting probe), an prostate cancer specific antibody labeled with a detectable label (e.g. antibodies of this invention labeled with a radioisotope, e.g. $^{161}$Tb, $^{123}$I, $^{125}$I, and the like), and, after allowing the active substance to be taken up by the target tissue, and preferably after blood clearance of the label, subjecting the mammal to a radioimmunodetection technique in the relevant area of the body, e.g. by using a gamma detecting probe.

In certain embodiments the label-bound antibody can be used in the technique of radioguided surgery, wherein relevant tissues in the body of a subject can be detected and located intraoperatively by means of a detector, e.g. a gamma detecting probe. The surgeon can, intraoperatively, use this probe to find the tissues in which uptake of the compound labeled with a radioisotope, that is, e.g. a low-energy gamma photon emitter, has taken place. In certain embodiments such methods are particularly useful in localizing and removing secondary cancers produced by metastatic cells from a primary tumor.

In addition to detectable labels, certain preferred effectors include, but are not limited to cytotoxins (e.g. *Pseudomonas* exotoxin, ricin, abrin, Diphtheria toxin, and the like), or cytotoxic drugs or prodrugs, in which case the chimeric molecule may act as a potent cell-killing agent specifically targeting the cytotoxin to prostate cancer cells.

In still other embodiments, the effector can include a liposome encapsulating a drug (e.g. an anti-cancer drug such as abraxane, doxorubicin, pamidronate disodium, anastrozole, exemestane, cyclophosphamide, epirubicin, toremifene, letrozole, trastuzumab, megestroltamoxifen, paclitaxel, docetaxel, capecitabine, goserelin acetate, zoledronic acid, vinblastine, etc.), an antigen that stimulates recognition of the bound cell by components of the immune system, an antibody that specifically binds immune system components and directs them to the prostate cancer, and the like.

Illustrative Effectors.

Imaging Compositions.

In certain embodiments, the macropinocytosis pathway internalizing antibodies can be used to direct detectable labels to and into a tumor site. This can facilitate tumor detection and/or localization. It can be effective for detecting primary tumors, or, in certain embodiments, secondary tumors produced by, e.g., prostate metastatic cells. In certain embodiments, the effector component of the immunoconjugate comprises a "radio-opaque" label, e.g. a label that can be easily visualized using x-rays. Radio-opaque materials are well known to those of skill in the art. The most common radio-opaque materials include iodide, bromide or barium salts. Other radiopaque materials are also known and include, but are not limited to, organic bismuth derivatives (see, e.g., U.S. Pat. No. 5,939,045), radio-opaque polyurethanes (see, e.g., U.S. Pat. No. 5,346,981), organobismuth composites (see, e.g., U.S. Pat. No. 5,256,334), radio-opaque barium polymer complexes (see, e.g., U.S. Pat. No. 4,866,132), and the like.

The macropinocytosis pathway internalizing antibodies described herein can be coupled directly to the radio-opaque moiety or they can be attached to a "package" (e.g., a chelate, a liposome, a polymer microbead, a nanoparticle, etc.) carrying, containing, or comprising the radio-opaque material, e.g., as described below.

In addition to radio-opaque labels, other labels are also suitable for use. Detectable labels suitable for use in immunoconjugates include any composition detectable by spectroscopic, photochemical, biochemical, immunochemical, electrical, optical or chemical means. Useful labels include, but are not limited to radiolabels (e.g., $^3$H, $^{125}$I, $^{35}$S, $^{14}$C, or $^{32}$P), PET labels, MRI labels, radio-opaque labels, and the like.

In certain embodiments, suitable radiolabels include, but are not limited to, $^{99}$Tc, $^{203}$Pb, $^{67}$Ga, $^{68}$Ga, $^{72}$As, $^{111}$In, $^{113m}$In, $^{97}$Ru, $^{62}$Cu, 641Cu, $^{52}$Fe, $^{52m}$Mn, $^{51}$Cr, $^{186}$Re, $^{188}$Re, $^{77}$As, $^{90}$Y, $^{67}$Cu, $^{169}$Er, $^{121}$Sn, $^{127}$Te, $^{142}$Pr, $^{43}$Pr, $^{198}$Au, $^{199}$Au, $^{161}$Tb, $^{109}$Pd, $^{165}$Dy $^{149}$Pm, $^{151}$Pm, $^{153}$Sm, $^{157}$Gd $^{159}$Gd, $^{166}$Ho, $^{172}$Tm, $^{169}$Yb, $^{175}$Yb, $^{177}$Lu, $^{105}$Rh, and $^{111}$Ag.

Means of detecting such labels are well known to those of skill in the art. Thus, for example, certain radiolabels may be detected using photographic film, scintillation detectors, PET imaging, MRI, and the like. Fluorescent markers can be detected using a photodetector to detect emitted illumination. Enzymatic labels are typically detected by providing the enzyme with a substrate and detecting the reaction product produced by the action of the enzyme on the substrate, and colorimetric labels are detected by simply visualizing the colored label.

Radiosensitizers.

In certain embodiments, the effector can comprise a radiosensitizer that enhances the cytotoxic effect of ionizing radiation (e.g., such as might be produced by $^{60}$Co or an x-ray source) on a cell. Numerous radiosensitizing agents are known and include, but are not limited to benzoporphyrin derivative compounds (see, e.g., U.S. Pat. No. 5,945,439), 1,2,4-benzotriazine oxides (see, e.g., U.S. Pat. No. 5,849,738), compounds containing certain diamines (see, e.g., U.S. Pat. No. 5,700,825), BCNT (see, e.g., U.S. Pat. No. 5,872,107), radiosensitizing nitrobenzoic acid amide derivatives (see, e.g., U.S. Pat. No. 4,474,814), various heterocyclic derivatives (see, e.g., U.S. Pat. No. 5,064,849), platinum complexes (see, e.g., U.S. Pat. No. 4,921,963), and the like.

Alpha Emitters.

In certain embodiments, the effector can include an alpha emitter, i.e. a radioactive isotope that emits alpha particles. Alpha-emitters have recently been shown to be effective in the treatment of cancer (see, e.g., McDevitt et al. (2001) Science 294:1537-1540; Ballangrud et al. (2001) Cancer Res. 61: 2008-2014; Borchardt et al. (2003) Cancer Res. 63: 5084-50). Suitable alpha emitters include, but are not limited to Bi, $^{213}$Bi, $^{211}$At, and the like.

Chelates

Many of the pharmaceuticals and/or radiolabels described herein can be provided as a chelate. The chelating molecule is typically coupled to a molecule (e.g. biotin, avidin, streptavidin, etc.) that specifically binds an epitope tag attached to a macropinocytosis pathway internalizing antibody described herein.

Chelating groups are well known to those of skill in the art. In certain embodiments, chelating groups are derived from ethylene diamine tetra-acetic acid (EDTA), diethylene triamine penta-acetic acid (DTPA), cyclohexyl 1,2-diamine tetra-acetic acid (CDTA), ethyleneglycol-O,O'-bis(2-aminoethyl)-N,N,N',N'-tetra-acetic acid (EGTA), N,N-bis(hydroxybenzyl)-ethylenediamine-N,N'-diacetic acid (HBED), triethylene tetramine hexa-acetic acid (TTHA), 1,4,7,10-tetraazacyclododecane-N,N'-,N'',N'''-tetra-acetic acid (DOTA), hydroxyethyldiamine triacetic acid (HEDTA), 1,4,8,11-tetra-azacyclotetradecane-N,N',N'',N'''-tetra-acetic acid (TETA), substituted DTPA, substituted EDTA, and the like.

Examples of certain preferred chelators include unsubstituted or, substituted 2-iminothiolanes and 2-iminothiacyclohexanes, in particular 2-imino-4-mercaptomethylthiolane.

One chelating agent, 1,4,7,10-tetraazacyclododecane-N, N, N'',N'''-tetraacetic acid (DOTA), is of particular interest because of its ability to chelate a number of diagnostically and therapeutically important metals, such as radionuclides and radiolabels.

Conjugates of DOTA and proteins such as antibodies have been described. For example, U.S. Pat. No. 5,428,156 teaches a method for conjugating DOTA to antibodies and antibody fragments. To make these conjugates, one carboxylic acid group of DOTA is converted to an active ester which can react with an amine or sulfhydryl group on the antibody or antibody fragment. Lewis et al. (1994) Bioconjugate Chem. 5: 565-576, describes a similar method wherein one carboxyl group of DOTA is converted to an active ester, and the activated DOTA is mixed with an antibody, linking the antibody to DOTA via the epsilon-amino group of a lysine residue of the antibody, thereby converting one carboxyl group of DOTA to an amide moiety.

In certain embodiments the chelating agent can be coupled, directly or through a linker, to an epitope tag or to a moiety that binds an epitope tag. Conjugates of DOTA and biotin have been described (see, e.g., Su (1995) *J Nucl. Med.*, 36 (5 Suppl):154P, which discloses the linkage of DOTA to biotin via available amino side chain biotin derivatives such as DOTA-LC-biotin or DOTA-benzyl-4-(6-amino-caproamide)-biotin). Yau et al., WO 95/15335, disclose a method of producing nitro-benzyl-DOTA compounds that can be conjugated to biotin. The method comprises a cyclization reaction via transient projection of a hydroxy group; tosylation of an amine; deprotection of the transiently protected hydroxy group; tosylation of the deprotected hydroxy group; and intramolecular tosylate cyclization. Wu et al. (1992) *Nucl. Med. Biol.*, 19(2): 239-244 discloses a synthesis of macrocylic chelating agents for radiolabeling proteins with $^{111}$IN and $^{90}$Y. Wu et al. makes a labeled DOTA-biotin conjugate to study the stability and biodistribution of conjugates with avidin, a model protein for studies. This conjugate was made using a biotin hydrazide which contained a free amino group to react with an in situ generated activated DOTA derivative.

Cytotoxins.

The macropinocytosis pathway internalizing antibodies described herein can be used to deliver a variety of cytotoxic drugs including therapeutic drugs, a compound emitting radiation, molecules of plants, fungal, or bacterial origin, biological proteins, and mixtures thereof. The cytotoxic drugs can be intracellularly acting cytotoxic drugs, such as short-range radiation emitters, including, for example, short-range, high-energy α-emitters as described above.

Enzymatically active toxins and fragments. thereof are exemplified by diphtheria toxin A fragment, nonbinding active fragments of diphtheria toxin, exotoxin A (from *Pseudomonas aeruginosa*), ricin A chain, abrin A chain, modeccin A chain, .alpha.-sacrin, certain *Aleurites fordii* proteins, certain Dianthin proteins, *Phytolacca americana* proteins (PAP, PAPII and PAP-S), *Morodica charantia* inhibitor, curcin, crotin, *Saponaria officinalis* inhibitor, gelonin, mitogillin, restrictocin, phenomycin, enomycin, and the tricothecenes, for example. A variety of radionuclides are available for the production of radioconjugated antibodies. Examples include, but are not limited to $^{212}$Bi, $^{131}$I, $^{131}$In, $^{90}$Y $^{186}$Re, and the like.

In certain embodiments the cytotoxins can include, but are not limited to *Pseudomonas* exotoxins, *Diphtheria* toxins, ricin, abrin and derivatives thereof. *Pseudomonas* exotoxin A (PE) is an extremely active monomeric protein (molecular weight 66 kD), secreted by *Pseudomonas aeruginosa*, which inhibits protein synthesis in eukaryotic cells through the inactivation of elongation factor 2 (EF-2) by catalyzing its ADP-ribosylation (catalyzing the transfer of the ADP ribosyl moiety of oxidized NAD onto EF-2).

The toxin contains three structural domains that act in concert to cause cytotoxicity. Domain Ia (amino acids 1-252) mediates cell binding. Domain II (amino acids 253-364) is responsible for translocation into the cytosol and domain III (amino acids 400-613) mediates ADP ribosylation of elongation factor 2, which inactivates the protein and causes cell death. The function of domain Ib (amino acids 365-399) remains undefined, although a large part of it, amino acids 365-380, can be deleted without loss of cytotoxicity. See Siegall et al. (1989) *J. Biol. Chem.* 264: 14256-14261.

In certain embodiments the antibody is attached to a preferred molecule in which domain Ia (amino acids 1 through 252) is deleted and amino acids 365 to 380 have been deleted from domain Ib. In certain embodiments all of domain Ib and a portion of domain II (amino acids 350 to 394) can be deleted, particularly if the deleted sequences are replaced with a linking peptide.

In addition, the PE and other cytotoxic proteins can be further modified using site-directed mutagenesis or other techniques known in the art, to alter the molecule for a particular desired application. For example, means to alter the PE molecule in a manner that does not substantially affect the functional advantages provided by the PE molecules described here can also be used and such resulting molecules are intended to be covered herein.

Methods of cloning genes encoding PE fused to various ligands are well known to those of skill in the art (see, e.g., Siegall et al. (1989) *FASEB J.*, 3: 2647-2652; and Chaudhary et al. (1987) *Proc. Natl. Acad. Sci. USA*, 84: 4538-4542).

Like PE, diphtheria toxin (DT) kills cells by ADP-ribosylating elongation factor 2 thereby inhibiting protein synthesis. Diphtheria toxin, however, is divided into two chains, A and B, linked by a disulfide bridge. In contrast to PE, chain B of DT, which is on the carboxyl end, is responsible for receptor binding and chain A, which is present on the amino end, contains the enzymatic activity (Uchida et al. (1972) *Science*, 175: 901-903; Uchida et al. (1973) *J. Biol. Chem.*, 248: 3838-3844).

In certain embodiments, the antibody-Diphtheria toxin immunoconjugates of this invention have the native receptor-binding domain removed by truncation of the Diphtheria toxin B chain. One illustrative modified Dipththeria toxin is DT388, a DT in which the carboxyl terminal sequence beginning at residue 389 is removed (see, e.g., Chaudhary et al. (1991) *Bioch. Biophys. Res. Comm.*, 180: 545-551). Like the PE chimeric cytotoxins, the DT molecules can be chemically conjugated to the prostate cancer specific antibody, but, in certain preferred embodiments, the antibody will be fused to the Diphtheria toxin by recombinant means (see, e.g., Williams et al. (1990) *J. Biol. Chem.* 265: 11885-11889).

Another suitable toxin is saporin. Saporin is a plant toxin that acts as a ribosome-inactivating protein that inhibits protein synthesis typically resulting in cellular apoptosis.

Viral Particles.

In certain embodiments, the effector comprises a viral particle (e.g., a filamentous phage, an adeno-associated virus (AAV), a lentivirus, and the like). The antibody can be conjugated to the viral particle and/or can be expressed on the surface of the viral particle (e.g. a filamentous phage). The viral particle can additionally include a nucleic acid that is to be delivered to the target (e.g., prostate cancer) cell. The use of viral particles to deliver nucleic acids to cells is described in detail in WO 99/55720, U.S. Pat. Nos. 6,670, 188, 6,642,051, and 6,669,936. Illustrative nucleic acids include, but are not limited to siRNAs (e.g., an EphA2 siRNA).

Other Therapeutic Moieties (Drugs).

Other suitable effector molecules include pharmacological agents (drugs) or encapsulation systems containing various pharmacological agents. Thus, in various embodiments, it is recognized that the macropinocytosis pathway internalizing antibody can be attached directly or through a linker to a drug that is to be delivered directly to the tumor or to an encapsulation system (e.g., a lipid, liposome, microparticle, nanoparticle, dendrimer, etc.) containing the drug. The term "drug" includes any substance that, when administered into the body of a living organism, alters normal bodily function. Generally a drug is a substance used in the treatment, cure, prevention, or diagnosis of disease or used to otherwise enhance physical or mental well-being. In one embodiment, the drug is an anti-neoplastic and/or cytostatic and/or cytotoxic drug (e.g., an anti-cancer drug).

Anti-cancer drugs are well known to those of skill in the art and include, but are not limited to, anti-cancer antibodies (e.g., trastuzumab (HERCEPTIN®), rituximab (RITUXAN®), etc.), antimetabolites, alkylating agents, topoisomerase inhibitors, microtubule targeting agents, kinase inhibitors, protein synthesis inhibitors, somatostatin analogs, glucocorticoids, aromatose inhibitors, mTOR inhibitors, protein Kinase B (PKB) inhibitors, phosphatidylinositol, 3-Kinase (PI3K) Inhibitors, cyclin dependent kinase inhibitors, anti-TRAIL molecules, MEK inhibitors, and the like. In certain embodiments the anti-cancer compounds include, but are not limited to flourouracil (5-FU), capecitabine/XELODA, 5-Trifluoromethyl-2'-deoxyuridine, methotrexate sodium, raltitrexed/Tomudex, pemetrexed/Alimta®, cytosine Arabinoside (Cytarabine, Ara-C)/Thioguanine, 6-mercaptopurine (Mercaptopurine, 6-MP), azathioprine/Azasan, 6-thioguanine (6-TG)/Purinethol (TEVA), pentostatin/Nipent, fludarabine phosphate/Fludara®, cladribine (2-CdA, 2-chlorodeoxyadenosine)/Leustatin, floxuridine (5-fluoro-2)/FUDR (Hospira, Inc.), ribonucleotide Reductase Inhibitor (RNR), cyclophosphamide/Cytoxan (BMS), neosar, ifosfamide/Mitoxana, thiotepa, BCNU-1,3-bis(2-chloroethyl)-1-nitosourea, 1,-(2-chloroethyl)-3-cyclohexyl-lnitrosourea, methyl CCNU, hexamethylmelamine, busulfan/Myleran, procarbazine HCL/Matulane, dacarbazine (DTIC), chlorambucil/Leukaran®, melphalan/Alkeran, cisplatin (Cisplatinum, CDDP)/Platinol, carboplatin/Paraplatin, oxaliplatin/Eloxitan, bendamustine, carmustine, chloromethine, dacarbazine (DTIC), fotemustine, lomustine, mannosulfan, nedaplatin, nimustine, prednimustine, ranimustine, satraplatin, semustine, streptozocin, temozolomide, treosulfan, triaziquone, triethylene melamine, thioTEPA, triplatin tetranitrate, trofosfamide, uramustine, doxorubicin HCL/Doxil, daunorubicin citrate/Daunoxome®, mitoxantrone HCL/Novantrone, actinomycin D, etoposide/Vepesid, topotecan HCL/Hycamtin, teniposide (VM-26), irinotecan HCL(CPT-11)/, Camptosar®, camptothecin, Belotecan, rubitecan, vincristine, vinblastine sulfate, vinorelbine tartrate, vindesine sulphate, paclitaxel/Taxol, docetaxel/Taxotere, nanoparticle paclitaxel, abraxane, ixabepilone, larotaxel, ortataxel, tesetaxel, vinflunine, and the like. In certain embodiments the anti-cancer drug(s) comprise one or more drugs selected from the group consisting of carboplatin (e.g., PARAPLATIN®), Cisplatin (e.g., PLATINOL®, PLATINOL-AQ®), Cyclophosphamide (e.g., CYTOXAN®, NEOSAR®), Docetaxel (e.g., TAXOTERE®), Doxorubicin (e.g., ADRIAMYCIN®), Erlotinib (e.g., TARCEVA®), Etoposide (e.g., VEPESID®), Fluorouracil (e.g., 5-FU®), Gemcitabine (e.g., GEMZAR®), imatinib mesylate (e.g., GLEEVEC®), Irinotecan (e.g., CAMPTOSAR®), Methotrexate (e.g., FOLEX®, MEXATE®, AMETHOPTERIN®), Paclitaxel (e.g., TAXOL®, ABRAXANE®), Sorafinib (e.g., NEXAVAR®), Sunitinib (e.g., SUTENT®), Topotecan (e.g., HYCAMTIN®), Vinblastine (e.g., VELBAN®), Vincristine (e.g., ONCOVIN®, VINCASAR PFS®). In certain embodiments the anti-cancer drug comprises one or more drugs selected from the group consisting of retinoic acid, a retinoic acid derivative, doxirubicin, vinblastine, vincristine, cyclophosphamide, ifosfamide, cisplatin, 5-fluorouracil, a camptothecin derivative, interferon, tamoxifen, and taxol. In certain embodiments the anti-cancer compound is selected from the group consisting of abraxane, doxorubicin, pamidronate disodium, anastrozole, exemestane, cyclophosphamide, epirubicin, toremifene, letrozole, trastuzumab, megestroltamoxifen, paclitaxel, docetaxel, capecitabine, goserelin acetate, zoledronic acid, vinblastine, etc.), an anti-sense molecule, an SiRNA, and the like.

In certain embodiments, the drug is a tubulin inhibitor. In certain embodiments the tubulin inhibitor is selected from the group consisting of an auristatin; and a maytansine derivative. In certain embodiments the drug is an auristatin. Auristatins include synthetic derivatives of the naturally occurring compound Dolastatin-10. Auristatins are a family of antineoplastic/cytostatic pseudopeptides. Dolastatins are structurally unique due to the incorporation of four unusual amino acids (Dolavaine, Dolaisoleuine, Dolaproine, and Dolaphenine) identified in the natural biosynthetic product. In addition this class of natural product has numerous asymmetric centets defined by total synthesis studies by Pettit et al (U.S. Pat. No. 4,978,744). It would appear from structure activity relationships that the Dolaisoleuine and Dolaproine residues appear necessary for antineoplastic activity (U.S. Pat. Nos. 5,635,483 and 5,780,588).

In one illustrative, but non-limiting embodiment, the auristatin is selected from the group consisting of auristatin E (AE), monomethylauristatin E (MMAE), auristatin F (MMAF), vcMMAE, and vcMMAF.

In certain embodiments the drug is a maytansine or a structural analogue of maytansine. Maytansines include structurally complex antimitotic polyketides. Maytansines are potent inhibitors of microtubulin assembly which promotes apoptosis in tumor cells. In certain embodiments the maytansine is selected from the group consisting of mertansine (DM1), and a structural analogue of maytansine such as DM3 or DM4. In certain embodiments the drug is mertansine (DM1).

In certain embodiments the drug is DNA interacting agent. In certain embodiments the drug is a DNA interacting agent selected from the group consisting of: (a) calicheamicins, duocarmycins, and pyrrolobenzodiazepines (PBDs).

In certain embodiments the drug is a calicheamicin. Calicheamicin is a potent cytotoxic agent that causes double-strand DNA breaks, resulting in cell death. Calicheamicin is a naturally occurring enediyne antibiotic (see, e.g., Smith et al. (1996) J. Med. Chem., 39: 2103-2117). In certain embodiments the the calicheamicin is calicheamicin gamma 1.

In certain embodiments the drug is a duocarmycin. Duocarmycins are potent anti-tumor antibiotics that exert their biological effects through binding sequence-selectively in the minor groove of DNA duplex and alkylating the N3 of adenine (see, e.g., Boger (1994) Pure & Appl. Chem., 66(4): 837-844). In certain embodiments the duocarmycin is selected from the group consisting of duocarmycin A, duocarmycin B1, duocarmycin B2, duocarmycin C1, duocarmycin C2, duocarmycin D, duocarmycin SA, cyclopropylbenzoindole (CBI) duocarmycin, centanamycin, rachelmycin (CC-1065), adozelesin, bizelesin, and Carzelesin.

In certain embodiments the drug is a pyrrolobenzodiazepine. Pyrrolobenzodiazepines (PBDs) are a class of naturally occurring anti-tumor antibiotics. PBDs exert their anti-tumor activity by covalently binding to the DNA in the minor groove specifically at purine-guanine-purine units. They insert on to the N2 of guamine via an aminal linkage and, due to their shape, they cause minimal disruption to the DNA helix. It is believed that the formation of the DNA-PBD adduct inhibits nucleic acid synthesis and causes excision-dependent single and double stranded breaks in the DNA helix. As synthetic derivatives the joining of two PBD units together via a flexible polymethylene tether allows the PBD dimers to cross-link opposing DNA strands producing highly lethal lesions.

In certain embodiments, the drug is a synthetic derivative of two pyrrolobenzodiazepines units joined together via a flexible polymethylene tether. In certain embodiments the pyrrolobenzodiazepine is selected from the group consisting of anthramycin (and dimers thereof), mazethramycin (and dimers thereof), tomaymycin (and dimers thereof), prothracarcin (and dimers thereof), chicamycin (and dimers thereof), neothramycin A (and dimers thereof), neothramycin B (and dimers thereof), DC-81 (and dimers thereof), Sibiromycin (and dimers thereof), porothramycin A (and dimers thereof), porothramycin B (and dimers thereof), sibanomycin (and dimers thereof), abbeymycin (and dimers thereof), SG2000, and SG2285.

In certain embodiments the effector comprises an encapsulation system, such as a viral capsid, a microporous nanoparticle (e.g., a silica or polymer nanoparticle), a dendrimer, a lipid, a liposome, or micelle that contains a therapeutic composition such as a drug (e.g., any one or more of the drugs described above), a nucleic acid (e.g. an antisense nucleic acid or another nucleic acid to be delivered to the cell), or another therapeutic moiety that is preferably shielded from direct exposure to the circulatory system. Means of preparing lipids, liposomes, dendrimers, and nanoparticles attached to antibodies are well known to those of skill in the art (see, e.g., U.S. Pat. No. 4,957,735, Connor et al. (1985) *Pharm. Ther.*, 28: 341-365, and the like).

B) Attachment of the Antibody to the Effector.

One of skill will appreciate that the macropinocytosis pathway internalizing antibodies described herein and the effector molecule(s) can be joined together in any order. Thus, where antibody is a single chain polypeptide, the effector molecule can be joined to either the amino or carboxy termini of the targeting molecule. The antibody can also be joined to an internal region of the effector molecule, or conversely, the effector molecule can be joined to an internal location of the antibody, as long as the attachment does not interfere with the respective activities of the molecules.

The antibody and the effector can be attached by any of a number of means well known to those of skill in the art. Typically the effector is conjugated, either directly or through a linker (spacer), to the antibody. However, in certain embodiments, where both the effector molecule is or comprises a polypeptide it is preferable to recombinantly express the chimeric molecule as a single-chain fusion protein.

Conjugation of the Effector Molecule to the Antibody.

In one embodiment, the macropinocytosis pathway internalizing antibody is chemically conjugated to the effector molecule (e.g., a cytotoxin, a label, a ligand, or a drug or liposome, etc.). Means of chemically conjugating molecules are well known to those of skill.

The procedure for attaching an effector to an antibody will vary according to the chemical structure of the effector and/or antibody. Polypeptides typically contain variety of functional groups; e.g., carboxylic acid (COOH) or free amine (—NH$_2$) groups, that are available for reaction with a suitable functional group on an effector molecule to bind the effector thereto.

Alternatively, the antibody and/or the effector can be derivatized to expose or attach additional reactive functional groups. The derivatization can involve attachment of any of a number of linker molecules such as those available from Pierce Chemical Company, Rockford Ill.

A "linker", as used herein, is a molecule that is used to join the targeting molecule to the effector molecule. The linker is capable of forming covalent bonds to both the targeting molecule and to the effector molecule. Suitable linkers are well known to those of skill in the art and include, but are not limited to, straight or branched-chain carbon linkers, heterocyclic carbon linkers, or peptide linkers. Where the targeting molecule and the effector molecule are polypeptides, the linkers may be joined to the constituent amino acids through their side groups (e.g., through a disulfide linkage to cysteine). However, in a preferred embodiment, the linkers will be joined to the alpha carbon amino or carboxyl groups of the terminal amino acids.

The immunoconjugates can be made using a variety of bifunctional protein coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., *Science* 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody (see, e.g., WO94/11026).

Many procedures and linker molecules for attachment of various compounds including radionuclide metal chelates, toxins and drugs to proteins such as antibodies are known (see, e.g., European Patent Application No. 188,256; U.S. Pat. Nos. 4,671,958, 4,659,839, 4,414,148, 4,699,784; 4,680,338; 4,569,789; and 4,589,071; and Borlinghaus et al. (1987) *Cancer Res.* 47: 4071-4075). In particular, production of various immunotoxins is well-known within the art and can be found, for example in Thorpe et al. (1982) *Monoclonal Antibodies in Clinical Medicine*, Academic Press, pp. 168-190, Waldmann (1991) *Science,* 252: 1657, U.S. Pat. Nos. 4,545,985 and 4,894,443, and the like.

In some circumstances, it is desirable to free the effector from the antibody when the immunoconjugate has reached its target site. Therefore, immunoconjugates comprising linkages that are cleavable in the vicinity of the target site may be used when the effector is to be released at the target site. Cleaving of the linkage to release the agent from the antibody may be prompted by enzymatic activity or conditions to which the immunoconjugate is subjected either inside the target cell or in the vicinity of the target site. When the target site is a tumor, a linker which is cleavable under conditions present at the tumor site (e.g. when exposed to tumor-associated enzymes or acidic pH) may be used.

A number of different cleavable linkers are known to those of skill in the art. See U.S. Pat. Nos. 4,618,492; 4,542,225, and 4,625,014. The mechanisms for release of an agent from these linker groups include, for example, irradiation of a photolabile bond and acid-catalyzed hydrolysis. U.S. Pat. No. 4,671,958, for example, includes a description of immunoconjugates comprising linkers which are cleaved at the target site in vivo by the proteolytic enzymes of the patient's complement system. In view of the large number of methods that have been reported for attaching a variety of radiodiagnostic compounds, radiotherapeutic compounds, drugs, toxins, and other agents to antibodies one skilled in the art will be able to determine a suitable method for attaching a given agent to an antibody or other polypeptide.

Conjugation of Chelates.

In certain embodiments, the effector comprises a chelate that is attached to an antibody or to an epitope tag. The the macropinocytosis pathway internalizing antibody bears a corresponding epitope tag or antibody so that simple contacting of the antibody to the chelate results in attachment of the antibody with the effector. The combining step can be performed before the moiety is used (targeting strategy) or the target tissue can be bound to the antibody before the chelate is delivered. Methods of producing chelates suitable for coupling to various targeting moieties are well known to those of skill in the art (see, e.g., U.S. Pat. Nos. 6,190,923, 6,187,285, 6,183,721, 6,177,562, 6,159,445, 6,153,775, 6,149,890, 6,143,276, 6,143,274, 6,139,819, 6,132,764, 6,123,923, 6,123,921, 6,120,768, 6,120,751, 6,117,412, 6,106,866, 6,096,290, 6,093,382, 6,090,800, 6,090,408, 6,088,613, 6,077,499, 6,075,010, 6,071,494, 6,071,490, 6,060,040, 6,056,939, 6,051,207, 6,048,979, 6,045,821, 6,045,775, 6,030,840, 6,028,066, 6,022,966, 6,022,523, 6,022,522, 6,017,522, 6,015,897, 6,010,682, 6,010,681, 6,004,533, and 6,001,329).

Production of Fusion Proteins.

Where the antibody and/or the effector is relatively short (i.e., less than about 50 amino acids) they can be synthesized using standard chemical peptide synthesis techniques. Where both molecules are relatively short the chimeric molecule may be synthesized as a single contiguous polypeptide. Alternatively the targeting molecule and the effector molecule may be synthesized separately and then fused by condensation of the amino terminus of one molecule with the carboxyl terminus of the other molecule thereby forming a peptide bond. Alternatively, the targeting and effector molecules can each be condensed with one end of a peptide spacer molecule thereby forming a contiguous fusion protein.

Solid phase synthesis in which the C-terminal amino acid of the sequence is attached to an insoluble support followed by sequential addition of the remaining amino acids in the sequence is the preferred method for the chemical synthesis of the polypeptides of this invention. Techniques for solid phase synthesis are described by Barany and Merrifield, *Solid-Phase Peptide Synthesis*; pp. 3-284 in *The Peptides: Analysis, Synthesis, Biology. Vol. 2: Special Methods in Peptide Synthesis, Part A.*, Merrifield, et al. *J. Am. Chem. Soc.*, 85: 2149-2156 (1963), and Stewart et al., *Solid Phase Peptide Synthesis,* 2nd ed. Pierce Chem. Co., Rockford, Ill. (1984).

In certain embodiments, the chimeric fusion proteins of the present invention are synthesized using recombinant DNA methodology. Generally this involves creating a DNA sequence that encodes the fusion protein, placing the DNA in an expression cassette under the control of a particular promoter, expressing the protein in a host, isolating the expressed protein and, if required, renaturing the protein.

DNA encoding the fusion proteins of this invention can be prepared by any suitable method, including, for example, cloning and restriction of appropriate sequences or direct chemical synthesis by methods such as the phosphotriester method of Narang et al. (1979)*Meth. Enzymol.* 68: 90-99; the phosphodiester method of Brown et al. (1979) *Meth. Enzymol.* 68: 109-151; the diethylphosphoramidite method of Beaucage et al. (1981) *Tetra. Lett.*, 22: 1859-1862; and the solid support method of U.S. Pat. No. 4,458,066.

Chemical synthesis produces a single stranded oligonucleotide. This can be converted into double stranded DNA by hybridization with a complementary sequence, or by polymerization with a DNA polymerase using the single strand as a template. One of skill would recognize that while chemical synthesis of DNA is limited to sequences of about 100 bases, longer sequences can be obtained by the ligation of shorter sequences.

Alternatively, subsequences can be cloned and the appropriate subsequences cleaved using appropriate restriction enzymes. The fragments can then be ligated to produce the desired DNA sequence.

In certain embodiments DNA encoding fusion proteins of the present invention can be cloned using PCR cloning methods.

While the antibody and the effector are, in certain embodiments, essentially joined directly together, one of skill will appreciate that the molecules can be separated by a spacer, e.g., a peptide spacer consisting of one or more amino acids (e.g., $(Gly_4Ser)_3$, SEQ ID NO:10). Generally the spacer will have no specific biological activity other than to join the proteins or to preserve some minimum distance or other spatial relationship between them. However, the constituent amino acids of the spacer may be selected to influence some property of the molecule such as the folding, net charge, or hydrophobicity.

The nucleic acid sequences encoding the fusion proteins can be expressed in a variety of host cells, including *E. coli*, other bacterial hosts, yeast, and various higher eukaryotic cells such as the COS, CHO and HeLa cells lines and myeloma cell lines. The recombinant protein gene will be operably linked to appropriate expression control sequences for each host.

The plasmids of the invention can be transferred into the chosen host cell by well-known methods such as calcium chloride transformation for *E. coli* and calcium phosphate treatment or electroporation for mammalian cells. Cells transformed by the plasmids can be selected by resistance to antibiotics conferred by genes contained on the plasmids, such as the amp, gpt, neo and hyg genes.

Once expressed, the recombinant fusion proteins can be purified according to standard procedures of the art, including ammonium sulfate precipitation, affinity columns, column chromatography, gel electrophoresis and the like (see, generally, R. Scopes (1982) *Protein Purification*, Springer-Verlag, N.Y.; Deutscher (1990) *Methods in Enzymology* Vol. 182: *Guide to Protein Purification.*, Academic Press, Inc. N.Y.). Substantially pure compositions of at least about 90 to 95% homogeneity are preferred, and 98 to 99% or more homogeneity are most preferred for pharmaceutical uses. Once purified, partially or to homogeneity as desired, the polypeptides may then be used therapeutically.

One of skill in the art would recognize that after chemical synthesis, biological expression, or purification, the fusion protein may possess a conformation substantially different than the native conformations of the constituent polypeptides. In this case, it may be necessary to denature and reduce the polypeptide and then to cause the polypeptide to re-fold into the preferred conformation. Methods of reducing and denaturing proteins and inducing re-folding are well known to those of skill in the art (see, e.g., Debinski et al. (1993) *J Biol. Chem.*, 268: 14065-14070; Kreitman and Pastan (1993) *Bioconjug. Chem.*, 4: 581-585; and Buchner, et al. (1992) *Anal. Biochem.*, 205: 263-270).

One of skill would recognize that modifications can be made to the fusion proteins without diminishing their biological activity. Some modifications may be made to facilitate the cloning, expression, or incorporation of the targeting molecule into a fusion protein. Such modifications are well known to those of skill in the art and include, for example, a methionine added at the amino terminus to provide an initiation site, or additional amino acids placed on either terminus to create conveniently located restriction sites or termination codons.

Pharmaceutical Compositions.

The macropinocytosis pathway internalizing antibodies described herein and/or immunoconjugates thereof are useful for parenteral, topical, oral, or local administration (e.g. injected into a tumor site), aerosol administration, or transdermal administration, for prophylactic, but principally for therapeutic treatment. The pharmaceutical compositions can be administered in a variety of unit dosage forms depending upon the method of administration. For example, unit dosage forms suitable for oral administration include powder, tablets, pills, capsules and lozenges. It is recognized that the antibodies described herein and/or immunoconjugates thereof and pharmaceutical compositions comprising antibodies described herein and/or immunoconjugates thereof, when administered orally, are preferably protected from digestion. This can be accomplished by a number of means known to those of skill in the art, e.g., by complexing the protein with a composition to render it resistant to acidic and enzymatic hydrolysis or by packaging the protein in an appropriately resistant carrier such as a liposome. Means of protecting proteins from digestion are well known in the art.

In various embodiments a composition, e.g., a pharmaceutical composition, containing one or a combination of the macropinocytosis pathway internalizing antibodies, or antigen-binding portion(s) thereof, or immunoconjugates thereof, formulated together with a pharmaceutically acceptable carrier are provided.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound, i.e., antibody, immunoconjugate, may be coated in a material to protect the compound from the action of acids and other natural conditions that may inactivate the compound.

In certain embodiments the antibody and/or immunoconjugate can be administered in the "native" form or, if desired, in the form of salts, esters, amides, prodrugs, derivatives, and the like, provided the salt, ester, amide, prodrug or derivative is suitable pharmacologically, i.e., effective in the present method(s). Salts, esters, amides, prodrugs and other derivatives of the active agents can be prepared using standard procedures known to those skilled in the art of synthetic organic chemistry and described, for example, by March (1992) *Advanced Organic Chemistry; Reactions, Mechanisms and Structure,* 4th Ed. N.Y. Wiley-Interscience, and as described above.

By way of illustration, a pharmaceutically acceptable salt can be prepared for any of the antibodies and/or immunoconjugates described herein having a functionality capable of forming a salt. A pharmaceutically acceptable salt is any salt that retains the activity of the parent compound and does not impart any deleterious or untoward effect on the subject to which it is administered and in the context in which it is administered.

In various embodiments pharmaceutically acceptable salts may be derived from organic or inorganic bases. The salt may be a mono or polyvalent ion. Of particular interest are the inorganic ions, lithium, sodium, potassium, calcium, and magnesium. Organic salts may be made with amines, particularly ammonium salts such as mono-, di- and trialkyl amines or ethanol amines. Salts may also be formed with caffeine, tromethamine and similar molecules.

Methods of formulating pharmaceutically active agents as salts, esters, amide, prodrugs, and the like are well known to those of skill in the art. For example, salts can be prepared from the free base using conventional methodology that typically involves reaction with a suitable acid. Generally, the base form of the drug is dissolved in a polar organic solvent such as methanol or ethanol and the acid is added thereto. The resulting salt either precipitates or can be brought out of solution by addition of a less polar solvent. Suitable acids for preparing acid addition salts include, but are not limited to both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, e.g., hydrochloric acid, hydrobromic acid, sulfuric acid, nitric acid, phosphoric acid, and the like. An acid addition salt can be reconverted to the free base by treatment with a suitable base. Certain particularly preferred acid addition salts of the active agents herein include halide salts, such as may be prepared using hydrochloric or hydrobromic acids. Conversely, preparation of basic salts of the active agents of this invention are prepared in a similar manner using a pharmaceutically acceptable base such as sodium hydroxide, potassium hydroxide, ammonium hydroxide, calcium hydroxide, trimethylamine, or the like. Particularly preferred basic salts include alkali metal salts, e.g., the sodium salt, and copper salts.

For the preparation of salt forms of basic drugs, the pKa of the counterion is preferably at least about 2 pH units lower than the pKa of the drug. Similarly, for the preparation of salt forms of acidic drugs, the pKa of the counterion is preferably at least about 2 pH units higher than the pKa of the drug. This permits the counterion to bring the solution's pH to a level lower than the $pH_{max}$ to reach the salt plateau, at which the solubility of salt prevails over the solubility of free acid or base. The generalized rule of difference in pKa units of the ionizable group in the active pharmaceutical ingredient (API) and in the acid or base is meant to make the proton transfer energetically favorable. When the pKa of the API and counterion are not significantly different, a solid complex may form but may rapidly disproportionate (i.e., break down into the individual entities of drug and counterion) in an aqueous environment.

Preferably, the counterion is a pharmaceutically acceptable counterion. Suitable anionic salt forms include, but are not limited to acetate, benzoate, benzylate, bitartrate, bromide, carbonate, chloride, citrate, edetate, edisylate, estolate, fumarate, gluceptate, gluconate, hydrobromide, hydrochloride, iodide, lactate, lactobionate, malate, maleate, mandelate, mesylate, methyl bromide, methyl sulfate, mucate, napsylate, nitrate, pamoate (embonate), phosphate and diphosphate, salicylate and disalicylate, stearate, succinate, sulfate, tartrate, tosylate, triethiodide, valerate, and the like, while suitable cationic salt forms include, but are not limited to aluminum, benzathine, calcium, ethylene diamine, lysine, magnesium, meglumine, potassium, procaine, sodium, tromethamine, zinc, and the like.

Preparation of esters typically involves functionalization of hydroxyl and/or carboxyl groups that are present within the molecular structure of the antibody and/or immunoconjugate. In certain embodiments, the esters are typically acyl-substituted derivatives of free alcohol groups, i.e., moieties that are derived from carboxylic acids of the formula RCOOH where R is alky, and preferably is lower alkyl. Esters can be reconverted to the free acids, if desired, by using conventional hydrogenolysis or hydrolysis procedures.

Amides can also be prepared using techniques known to those skilled in the art or described in the pertinent literature. For example, amides may be prepared from esters, using suitable amine reactants, or they may be prepared from an anhydride or an acid chloride by reaction with ammonia or a lower alkyl amine.

Pharmaceutical compositions comprising the antibodies and/or immunoconjugates described herein can be administered alone or in combination therapy, i.e., combined with other agents. For example, the combination therapy can include a an antibody or immunoconjugate with at least one or more additional therapeutic agents, such as the anti-cancer agents described infra. The pharmaceutical compositions can also be administered in conjunction with radiation therapy and/or surgery.

A composition comprising the antibodies and/or immunoconjugates described herein can be administered by a variety of methods known in the art. As will be appreciated by the skilled artisan, the route and/or mode of administration will vary depending upon the desired results. The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art (see, e.g., Sustained and Controlled Release Drug Delivery Systems, J. R. Robinson, ed., Marcel Dekker, Inc., New York, 1978).

In certain embodiments administration of the macropinocytosis pathway internalizing antibody or immunoconjugate may be facilitated by coating the antibody or immunoconjugate composition, or co-administering the antibody or immunoconjugate, a material to prevent its inactivation. For example, the compound may be administered to a subject in an appropriate carrier, for example, liposomes, or a diluent. Pharmaceutically acceptable diluents include, but are not limited to, saline and aqueous buffer solutions. Liposomes include, but are not limited to, water-in-oil-in-water CGF emulsions as well as conventional liposomes (Strejan et al. (1984) *J. Neuroimmunol*, 7: 27).

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of is contemplated. Supplementary active compounds can also be incorporated into the compositions.

In various embodiments the therapeutic compositions are typically sterile and stable under the conditions of manufacture and storage. The composition(s) can be formulated as a solution, a microemulsion, in a lipid or liposome, or other ordered structure suitable to contain high drug concentration(s). In certain embodiments the carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound (e.g., antibodies and/or immunoconjugates described herein) in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, illustrative methods of preparation include vacuum drying, and freeze-drying (lyophilization) that yield a powder of the active ingredient plus any additional desired ingredient from a previously sterile-filtered solution thereof.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. For example, in certain embodiments, the antibodies and/or immunoconjugates described herein may be administered once or twice daily, or once or twice weekly, or once or twice monthly by subcutaneous injection.

It is especially advantageous to formulate parenteral compositions in unit dosage form for ease of administration and uniformity of dosage. Unit dosage form as used herein refers to physically discrete units suited as unitary dosages for the subjects to be treated. Each unit contains a predetermined quantity of active compound calculated to produce the desired therapeutic effect in association with the required pharmaceutical carrier. The specifications for the unit dosage forms are dictated by and directly dependent on (a) the unique characteristics of the active compound and the particular therapeutic effect to be achieved, and (b) the limitations inherent in the art of compounding such an active compound for the treatment of individuals.

In certain embodiments the formulation comprises a pharmaceutically anti-oxidant. Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

For the therapeutic compositions, formulations of the antibodies and/or immunoconjugates described herein include those suitable for oral, nasal, topical (including buccal and sublingual), rectal, vaginal and/or parenteral administration. The formulations may conveniently be presented in unit dosage form and may be prepared by any methods known in the art of pharmacy. The amount of active ingredient which can be combined with a carrier material to produce a single dosage form will vary depending upon the subject being treated, and the particular mode of administration. The amount of active ingredient that can be combined with a carrier material to produce a single dosage form will generally be that amount of the composition which produces a therapeutic effect. Generally, out of one hundred percent, this amount will range from about 0.001 percent to about ninety percent of active ingredient, preferably from about 0.005 percent to about 70 percent, most preferably from about 0.01 percent to about 30 percent.

Formulations of antibodies and/or immunoconjugates described herein that are suitable for vaginal administration also include pessaries, tampons, creams, gels, pastes, foams or spray formulations containing such carriers as are known in the art to be appropriate. Dosage forms for the topical or transdermal administration of antibodies and/or immunoconjugates described herein include powders, sprays, ointments, pastes, creams, lotions, gels, solutions, patches and inhalants. In certain embodiments the active compound may be mixed under sterile conditions with a pharmaceutically acceptable carrier, and with any preservatives, buffers, or propellants that may be required.

The phrases "parenteral administration" and "administered parenterally" as used herein means modes of administration other than enteral and topical administration, usually by injection, and include, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection, and infusion.

Examples of suitable aqueous and nonaqueous carriers that may be employed in the pharmaceutical compositions comprising antibodies and/or immunoconjugates described herein include, but are not limited to water, ethanol, polyols (such as glycerol, propylene glycol, polyethylene glycol, and the like), and suitable mixtures thereof, vegetable oils, such as olive oil, and injectable organic esters, such as ethyl oleate, and the like. Proper fluidity can be maintained, for example, by the use of coating materials, such as lecithin, by the maintenance of the required particle size in the case of dispersions, and by the use of surfactants.

In various embodiments these compositions may also contain adjuvants such as preservatives, wetting agents, emulsifying agents and dispersing agents. Particular examples of adjuvants that are well-known in the art include, for example, inorganic adjuvants (such as aluminum salts, e.g., aluminum phosphate and aluminum hydroxide), organic adjuvants (e.g., squalene), oil-based adjuvants, virosomes (e.g., virosomes that contain a membrane-bound hemagglutinin and neuraminidase derived from the influenza virus).

Prevention of presence of microorganisms in formulations may be ensured both by sterilization procedures, and/or by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

When the antibodies and/or immunoconjugates described herein are administered as pharmaceuticals, to humans and animals, they can be given alone or as a pharmaceutical composition containing, for example, 0.001 to 90% (more preferably, 0.005 to 70%, such as 0.01 to 30%) of active ingredient in combination with a pharmaceutically acceptable carrier.

Regardless of the route of administration selected, the antibodies and/or immunoconjugates described herein, that may be used in a suitable hydrated form, and/or the pharmaceutical compositions, are formulated into pharmaceutically acceptable dosage forms by conventional methods known to those of skill in the art.

Actual dosage levels of the active ingredients (e.g., antibodies and/or immunoconjugates described herein) in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts. A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved. In general, a suitable daily dose of antibodies and/or immunoconjugates described herein will be that amount of the compound which is the lowest dose effective to produce a therapeutic effect. Such an effective dose will generally depend upon the factors described above. In certain embodiments, it is preferred that administration be intravenous, intramuscular, intraperitoneal, or subcutaneous, preferably administered proximal to the site of the target. If desired, the effective daily dose of a therapeutic composition may be administered a single dosage, or as two, three, four, five, six or more sub-doses administered separately at appropriate intervals throughout the day, optionally, in unit dosage forms. While it is possible for antibodies and/or immunoconjugates described herein to be administered alone, it is typically preferable to administer the compound(s) as a pharmaceutical formulation (composition).

In certain embodiments the therapeutic compositions can be administered with medical devices known in the art. For example, in a illustrative embodiment, antibodies and/or immunoconjugates described herein can be administered with a needleless hypodermic injection device, such as the devices disclosed in U.S. Pat. Nos. 5,399,163, 5,383,851, 5,312,335, 5,064,413, 4,941,880, 4,790,824, or 4,596,556. Examples of useful well-known implants and modules are described for example in U.S. Pat. No. 4,487,603, which discloses an implantable micro-infusion pump for dispensing medication at a controlled rate, in U.S. Pat. No. 4,486,194, which discloses a therapeutic device for administering medications through the skin, in U.S. Pat. No. 4,447,233, which discloses a medication infusion pump for delivering medication at a precise infusion rate, in U.S. Pat. No. 4,447,224, which discloses a variable flow implantable infusion apparatus for continuous drug delivery, in U.S. Pat.

No. 4,439,196, which discloses an osmotic drug delivery system having multi-chamber compartments, and in U.S. Pat. No. 4,475,196, which discloses an osmotic drug delivery system. Many other such implants, delivery systems, and modules are known to those skilled in the art.

In certain embodiments, the macropinocytosis pathway internalizing antibodies and/or immunoconjugates described herein can be formulated to ensure proper distribution in vivo. For example, the blood-brain barrier (BBB) excludes many highly hydrophilic compounds. To ensure that the therapeutic compounds of the invention cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., Ranade (1989) *J. Clin. Pharmacol.* 29: 685). Illustrative targeting moieties include, but are not limited to folate or biotin (see, e.g., U.S. Pat. No. 5,416,016); mannosides (Umezawa et al., (1988) *Biochem. Biophys. Res. Commun.* 153: 1038); antibodies (Bloeman et al. (1995) *FEBS Lett.* 357:140; Owais et al. (1995) *Antimicrob. Agents Chemother.* 39:180); surfactant protein A receptor (Briscoe et al. (1995) *Am. J Physiol.* 1233:134).
Kits.

Where a radioactive, or other, effector is used as a diagnostic and/or therapeutic agent, it is frequently impossible to put the ready-for-use composition at the disposal of the user, because of the often poor shelf life of the radiolabeled compound and/or the short half-life of the radionuclide used. In such cases the user can carry out the labeling reaction with the radionuclide in the clinical hospital, physician's office, or laboratory. For this purpose, or other purposes, the various reaction ingredients can then be offered to the user in the form of a so-called "kit". The kit is preferably designed so that the manipulations necessary to perform the desired reaction should be as simple as possible to enable the user to prepare from the kit the desired composition by using the facilities that are at his disposal. Therefore the invention also relates to a kit for preparing a composition according to this invention.

In certain embodiments, such a kit comprises one or more antibodies or immumoconjugates described herein. The antibodies or immumoconjugates can be provided, if desired, with inert pharmaceutically acceptable carrier and/or formulating agents and/or adjuvants is/are added. In addition, the kit optionally includes a solution of a salt or chelate of a suitable radionuclide (or other active agent), and (iii) instructions for use with a prescription for administering and/or reacting the ingredients present in the kit.

The kit to be supplied to the user may also comprise the ingredient(s) defined above, together with instructions for use, whereas the solution of a salt or chelate of the radionuclide, defined sub (ii) above, which solution has a limited shelf life, may be put to the disposal of the user separately.

The kit can optionally, additionally comprise a reducing agent and/or, if desired, a chelator, and/or instructions for use of the composition and/or a prescription for reacting the ingredients of the kit to form the desired product(s). If desired, the ingredients of the kit may be combined, provided they are compatible.

In certain embodiments, the immunoconjugate can simply be produced by combining the components in a neutral medium and causing them to react. For that purpose the effector may be presented to the antibody, for example, in the form of a chelate.

When kit constituent(s) are used as component(s) for pharmaceutical administration (e.g. as an injection liquid) they are preferably sterile. When the constituent(s) are provided in a dry state, the user should preferably use a sterile physiological saline solution as a solvent. If desired, the constituent(s) may be stabilized in the conventional manner with suitable stabilizers, for example, ascorbic acid, gentisic acid or salts of these acids, or they may comprise other auxiliary agents, for example, fillers, such as glucose, lactose, mannitol, and the like.

While the instructional materials, when present, typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

EXAMPLES

The following examples are offered to illustrate, but not to limit the claimed invention.

Example 1

High-Content Analysis of Antibody Phage-Display Libraries Identifies Tumor Selective Macropinocytosis-Dependent Rapidly Internalizing Antibodies Abbreviations The following abbreviations are used in this example: HCA: High content analysis; ScFv: single chain variable fragment; PCC: Pearson's correlation coefficient; CFU: Colony forming unit; MFI: mean fluorescence intensity; EEA: early endosomal antigen; LAMP: lysosomal-associated membrane protein; IgG: immunoglobulin G; ND70-TR: Texas Red-conjugated neutral dextran 70 kDa; FBS: Fetal bovine serum; HEK: human embryonic kidney; LCM: Laser capture microdissection; EphA2: ephrin type-A receptor 2; HRP: horseradish peroxidase; IC50: half maximal inhibitory concentration; MAbs: monoclonal antibodies.
Summary of Example 1.

Many forms of antibody-based targeted therapeutics, including antibody drug conjugates, utilize the internalizing function of the targeting antibody to gain intracellular entry into tumor cells. Ideal antibodies for developing such therapeutics should be capable of both tumor-selective binding and efficient endocytosis. The macropinocytosis pathway is capable of both rapid and bulk endocytosis, and recent studies have demonstrated that it is selectively upregulated by cancer cells. It was hypothesized that receptor-dependent macropinocytosis can be achieved using tumor-targeting antibodies that internalize via the macropinocytosis pathway, improving potency and selectivity of the antibody-based targeted therapeutic. While phage antibody display libraries have been utilized to find antibodies that bind and internalize to target cells, it is believed that no methods have been described to screen for antibodies that internalize specifically via macropinocytosis.

A novel screening strategy to identify phage antibodies that bind and rapidly enter tumor cells via macropinocytosis is described herein. An automated microscopic imaging-based, High Content Analysis platform was used to identify novel internalizing phage antibodies that colocalize with macropinocytic markers from antibody libraries that we have generated previously by laser capture microdissection-based selection, which are enriched for internalizing antibodies binding to tumor cells in situ residing in their tissue microenvironment (Ruan et al. (2006) *Mol. Cell Proteomics.* 5: 2364-2373). Full-length human IgG molecules derived from macropinocytosing phage antibodies retained the ability to internalize via macropinocytosis, validating our screening strategy. The target antigen for a cross-species binding antibody with a highly active macropinocytosis activity was identified as ephrin type-A receptor 2. Antibody-toxin conjugates created using this macropinocytosing IgG were capable of potent and receptor-dependent killing of a panel of EphA2-positive tumor cell lines in vitro. These studies identify novel methods to screen for and validate antibodies capable of receptor-dependent macropinocytosis, allowing further exploration of this highly efficient and tumor-selective internalization pathway for targeted therapy development.

Materials and Methods

Tissue Culture

Prostate cancer cell lines DU145 and LNCaP, breast cancer cell line MDA-MB-231, lung cancer cell line A549, cervical cancer cell line HeLa, epidermoid carcinorma cell line A431, and human embryonic kidney (HEK) 293A cell line were purchased from the American Type Culture Collection (ATCC). Human foreskin normal fibroblast line Hs27 was purchased from UCSF Cell Culture Core Facility. Benign prostatic hyperplasia (BPH-1) cells were originally obtained from Dr. Gerald Cunha's lab at UCSF (Hayward et al. (1995) *In vitro Cell Dev. Biol. Anim.* 31: 14-24) and maintained in the lab. All cells were grown in high-glucose, L-glutamine, and sodium pyruvate-supplemented complete DMEM (Caisson Labs) with the addition of 10% fetal bovine serum (Fisher Scientific) and penicillin-streptomycin solution (Axenia BioLogix). Cells were grown in 5% $CO_2$ at 37° C. on tissue culture-treated flasks (BD Biosciences). Cells were passaged utilizing 0.25% trypsin-EDTA (Life Technologies).

Preparation of Phage Antibody Display Library Selection Output for Screening

Phage antibody library selection outputs generated previously by LCM-based selection on prostate tumor tissues (Ruan et al. (2006)*Mol. Cell Proteomics,* 5: 2364-2373) were streaked onto 2×YT agar plates containing 12.5 µg/ml tetracycline to yield monoclonal phage antibodies. Individual colonies were inoculated in 2×YT containing 12.5 µg/ml tetracycline and grown in deep 96-well plates (Fisher Scientific) at 37° C. with 225 RPM shaking for 18 h. The plates were centrifuged to pellet the bacteria and supernatants containing phage particles were transferred into a new 96-well plate for HCA experiments (see below). Positive clones from initial HCA screenings were re-tested using purified phage using polyethylene glycol (PEG8000) as previously described (. Ruan et al. (2006) *Mol. Cell Proteomics,* 5: 2364-2373; Zhu et al. (2010) *Mol. Cancer Ther.* 9: 2131-2141; An et al. (2008) *Mol. Cancer Ther.* 7: 569-578; Liu et al. (2004) *Cancer Res.* 64: 704-710). Antibody sequences were determined using 96-well plate-based DNA sequencing (Functional Biosciences).

Recombinant Antibody Cloning, Expression, and Purification

For IgG production, heavy and light chain variable fragments were subcloned into IgG-AbVec (kindly provided by Dr. Patrick Wilson at University of Chicago) γ and λ mammalian expression vectors, as previously described, to produce secretable IgG1 antibodies (Smith et al. (2009) *Nat. Protoc.* 4: 372-384). For scFv-Fc fusion production, scFv was subcloned from phage into pFUSE-hIgG1 Fc2 (InvivoGen). Mammalian transfection complexes containing antibody expression DNA and polyethylenimine (Sigma-Aldrich) in Opti-MEM (Life Technologies) were added to HEK 293A cells in the presence of serum-free DMEM containing Nutridoma-SP (Roche) and penicillin-streptomycin. Antibody-containing media were harvested after 4 days and affinity-purified using protein A agarose (Pierce/Fisher). Antibody concentrations were determined using the BLITZ® Bio-Layer interferometry System (ForteBio).

HCA Screening

Supernatants from 96-well bacterial culture plates (see above) were used for initial HCA screening. DU145 cells were seeded in 96-well plates (BD Biosciences) overnight, and incubated with phage-containing supernatants and 50 µg/ml Texas Red-conjugated 70-kDa neutral dextran (ND70-TR, Life Technologies) in DMEM/10% FBS at 37° C. with 5% $CO_2$ overnight. Cells were washed 3× with PBS, fixed with 4% paraformaldehyde (Santa Cruz Biotechnology) in PBS for 10 min, washed 3× in PBS, and then permeabilized in PBS containing 1% fraction V bovine serum albumin (Fisher Scientific) and 0.1% TritonX-100 (Sigma). Phage were detected with 3.5 µg/ml biotin-conjugated, rabbit anti-fd bacteriophage (Sigma-Aldrich) for 1 h at RT followed by 1 µg/ml ALEXA FLUOR® 488-conjugated streptavidin (Jackson ImmunoResearch) for 15 min at RT. Hoechst 33342 (Thermo Scientific) at 1 µg/ml for 30 min at RT was used to detect nuclei. The 96-well plates were imaged on a CellInsight™ NXT HCS platform (Thermo Scientific) with a semi-aprochromat 20× LUCPLFLN objective (Olympus) utilizing >6 fields per well with a minimum of 300 cells per well. Pearson's correlation coefficient analysis between ND70-TR and phage particles were conducted using Thermo Scientific HCS Studio software suite on all imaged fields and averaged per well.

Confocal Analysis:

DU145 cells were seeded in 8-well Lab-Tek II chambered coverglass (Thermo Scientific) overnight for confocal microscopy studies. Cells were incubated with antibodies (IgGs at 10 µg/ml or purified phage at $10^9$ cfu/ml) and 50 µg/ml ND70-TR in DMEM/10% FBS at 37° C. with 5% $CO_2$ for indicated periods (see text), washed, fixed and permeabilized as described above. To label subcellular structures, rabbit antibodies against early endosomes, lysosomes, caveolin-2, and clathrin heavy chain (Cell Signaling) were added to permeabilized cells at 1:100 dilutions for 3 h at RT. Cell-associated human IgGs were detected with 1 µg/ml ALEXA FLUOR® 647-conjugated goat anti-human IgG (Jackson ImmunoResearch) for 30 min at RT. Cell-associated phage were detected with 3.5 µg/ml biotin-conjugated, rabbit anti-fd bacteriophage for 1 h at RT followed by 1 µg/ml ALEXA FLUOR® 488-conjugated streptavidin (Jackson ImmunoResearch) for 15 min at RT. Antibodies against organelles were detected with ALEXA FLUOR® 488- or phycoerythrin-conjugated goat anti-rabbit for 30 min at RT. Hoechst 33342 at 1 µg/ml for 30 min at RT was used to detect nuclei. Cells in 8-well glass chambered coverglass were then imaged on the FLUOVIEW® FV10i laser confocal microscope (Olympus) equipped with two galvanometer scanning mirrors. Confocal images were taken with an Olympus 60×phase contrast water-immersion objective with NA 1.2. Image analyses including Pearson's and Mander's correlation coefficients, Z-projection, Z-projection dissection, and 3D renderings were performed with the included Olympus confocal software suite.

Internalization Kinetics Assay

DU145 cells seeded in 8-well chambered coverglass were pulsed with antibodies at 10 µg/ml in complete DMEM/FBS for 30 min at 4° C., followed by a chase in 37° C. warmed, complete DMEM/FBS and incubated at 37° C. with 5% $CO_2$. Individual wells at varying time points were then washed in PBS and fixed in 4% paraformaldehyde before undergoing immunofluorescence as described above. For flow cytometry-based internalization kinetics assay, DU145 cells were seeded in 6-well plate, then treated with antibodies at 10 µg/ml for varying amounts of time. Then cells were trypsinized, probed with anti-human secondary antibody, and analyzed on a flow cytometer. Cytochalasin D (Sigma) was resuspended in DMSO and cells were pulsed with 50 µg/ml of the drug in serum-free DMEM at 37° C., followed by a chase in complete DMEM/FBS containing the drug and antibodies.

Immunoprecipitation of the Target Antigen

Purified HCA-F1 scFv-Fc fusions were first chemically cross-linked to protein A agarose beads. Briefly, antibodies were affinity-bound onto protein A agarose (Life Technologies) in a tube. Beads were then spun down and washed with 0.2 M sodium borate, pH 9.0. Dry dimethyl pimelimidate (DMP, Sigma) was added to the beads in the presence of sodium borate to yield a final concentration of 13 mg/ml and incubated at RT for 30 min. Beads were washed with sodium borate and DMP crosslinking was repeated a second time. Chemical crosslinking was terminated through washes with 0.2 M ethanolamine, pH 8.0, for 2 h at RT. Finally, unconjugated antibodies were eluted from beads using 0.1 M glycine, pH 2.8, followed by washes with PBS. Exposed surface proteins on DU145 cells were biotinylated using EZ-Link Sulfo-NHS-LC-Biotin (Thermo Pierce) according to manufacturer's recommendations and then lysed using standard RIPA buffer (50 mM Tris, pH 7-8, 150 mM NaCl, 0.1% SDS, 0.5% sodium deoxycholate, 1% NP-40). Immunoprecipitation was performed as described previously (Liu et al. (2007) *J Mol. Med. (Berl)*. 85: 1113-1123; Conrad et al. (2009) *J Mol. Med. (Berl)*. 87: 507-514). Briefly, 5 mg of biotinylated lysates were first pre-cleared against protein A agarose for 1 h at RT and then incubated with scFv-Fc-conjugated protein A beads overnight at 4° C. Beads were then washed with 500 mM NaCl in PBS, spun down, and boiled in SDS sample buffer to be run on two 4-12% Tris-glycine SDS-PAGE gels (Life Technologies). One gel was GelCode-stained (Thermo) and the other gel was used for Western blotting using standard procedures. Horseradish peroxidase-conjugated streptavidin was used in the Western Blot to assess which protein band to extract from the GelCode-stained gel.

Antigen Identification by Mass Spectrometry Analysis

Extracted gel bands were trypsin-digested and analyzed via tandem mass spectrometry (MS/MS, University of Minnesota) (see, e.g., Table 3). Charge state deconvolution and deisotoping were not performed. All MS/MS samples were analyzed using Sequest (Thermo Fisher Scientific; version 27, rev. 12). Sequest was set up to search the rs_human9606_031313_cRAP123 database (unknown version, 36010 entries) assuming the digestion enzyme trypsin. Sequest was searched with a fragment ion mass tolerance of 0.80 Da and a parent ion tolerance of 0.079 Da and 0.32 Da. Iodoacetamide derivative of cysteine and oxidation of methionine were specified as fixed and variable modifications, respectively, in Sequest. Scaffold (version 4.0.5, Proteome Software Inc.) was used to validate protein identifications to create peak lists. Peptide identifications were accepted if they could be established at greater than 95.0% probability by the Peptide Prophet algorithm (Keller et al. (2002) *Anal. Chem.* 74: 5383-5392). Protein identifications were accepted if they could be established at greater than 90.0% probability and contained at least 2 identified peptides. Protein probabilities were assigned by the Protein Prophet algorithm (Nesvizhskii et al. (2003) *Anal. Chem.* 75: 4646-4458). Peptide and protein false discovery rates, as determined by Protein Prophet algorithm, are 0.4% and 0.1%, respectively. Proteins that contained similar peptides and could not be differentiated based on MS/MS analysis alone were grouped to satisfy the principles of parsimony.

Antibody-Toxin Cytotoxicity Assay

The human IgG HCA-F1 was biotinylated with EZ-Link Sulfo-NHS-LC-Biotin (Thermo Pierce) according to manufacturer's recommendations. A panel of tumor and non-tumorigenic cell lines were seeded in 96-well plates at a density of 1,000-2,000 cells per well and grown for 16 h at 37° C. in 5% $CO_2$. Biotinylated IgG HCA-F1 was then incubated with streptavidin-ZAP (saporin conjugated with streptavidin, Advanced Targeting Systems) at a molar ratio of 1:1 and incubated on ice for 30 min to form the antibody-toxin (saporin) conjugate, which was then added to cells and incubated for 96 h at 37° C. in 5% $CO_2$. Cell viability was then determined by CCK-8 assay (Dojindo) according to manufacturer's recommendations using the Synergy HT microtiter plate reader (Bio-Tek). IC50 values were determined by curve fit using Prism (GraphPad Software).

Results

HCA-Based Screening Strategy

The HCA-based strategy that we used to identify antibodies capable of internalizing into tumor cells via macropinocytosis is outlined in FIG. 2A. The key feature is the development of an HCA platform that allows quantitative measurement of colocalization between phage antibodies and a macropinocytic marker, ND70-TR. To identify clinically relevant macropinocytosing antibodies, we screened phage antibody libraries that we have generated previously by laser capture microdissection (LCM)-based selection, which are highly enriched for internalizing antibodies that bind to prostate tumor cells in situ residing in the tumor tissue microenvironment (Ruan et al. (2006) *Mol. Cell Proteomics*. 5: 2364-2373).

Figure 2B:
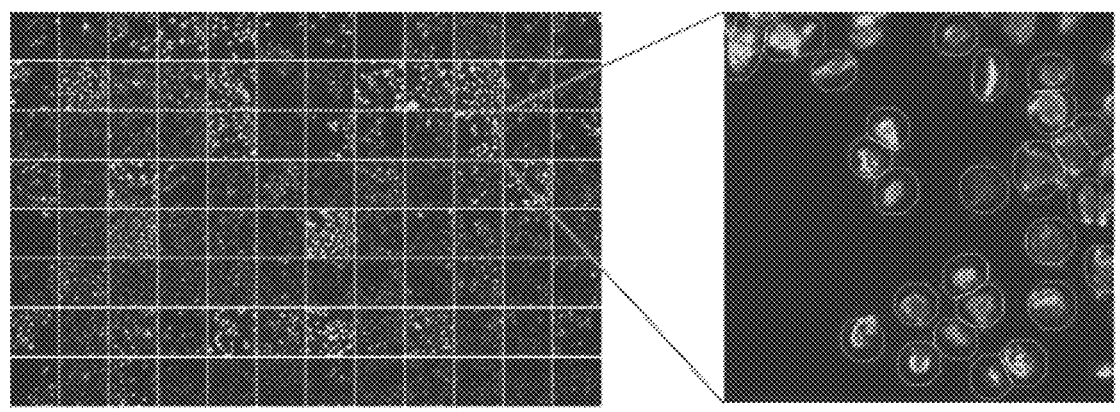
Figure 2C:
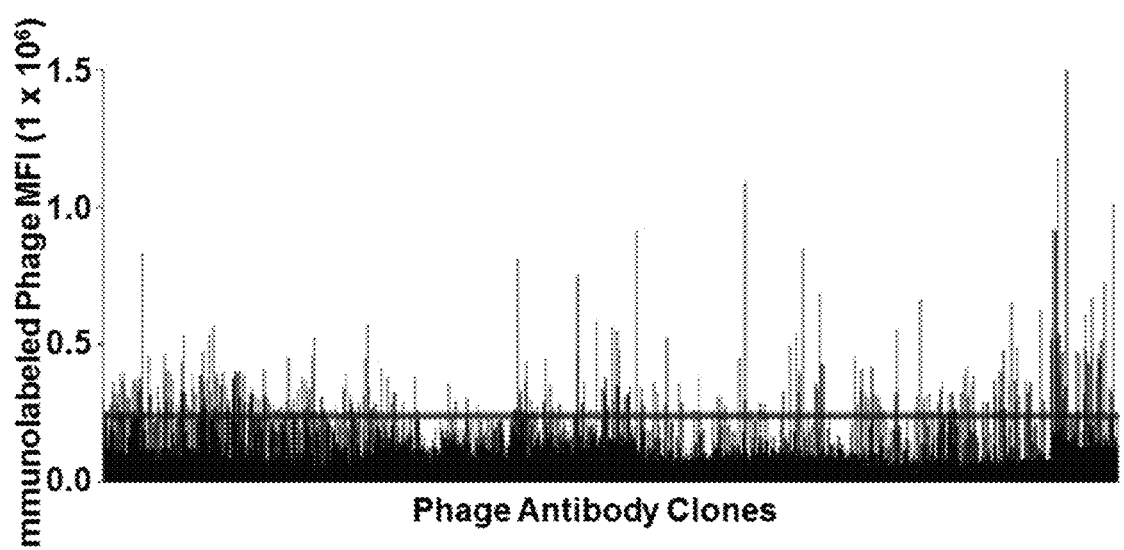
Figure 10:
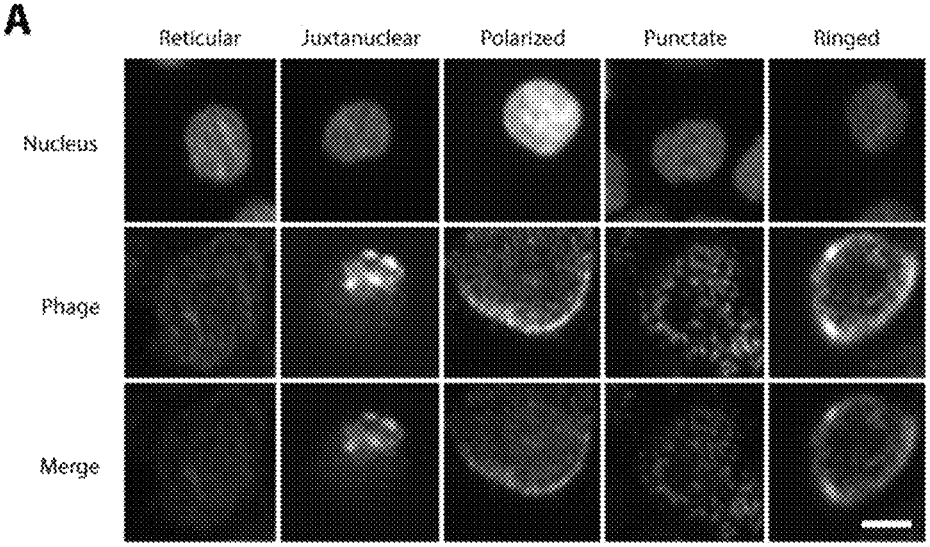
FIG. 10, panels A-B, shows patterns of cell-associated phage antibodies. Panel A) Various patterns of cell-associated phage antibodies. DU145 cells were incubated with phage containing supernatants at 37° C. for 2 h, washed, fixed, permeabilized, and phage detected by anti-fd antibodies (green). Nuclei were stained with Hoechst 33342. Scale bar: 20 µm. Panel B) Summary of phage antibody patterns; n=13 unique phage clones. These patterns are not mutually exclusive as a monoclonal phage often exhibits multiple patterns as indicated
Figure 11:
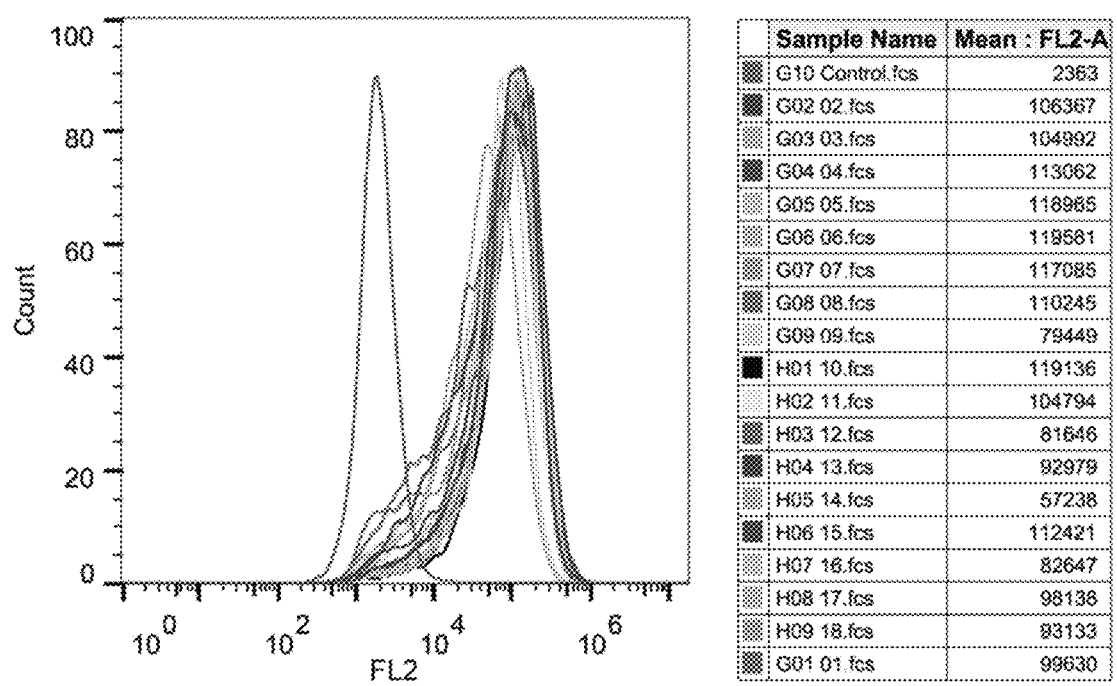
FIG. 11 shows FACS analysis of phage antibody binding to DU145 cells. Bound phage were detected by biotin-labeled anti-fd antibody followed by streptavidin-PE. MFI values are shown in the right panel.

Analysis of Phage Antibody Binding Patterns by Automated Fluorescence Microscopy Phage infected bacteria were arrayed into 96-well plates and phage-containing supernatants were incubated with prostate cancer DU145 cells in 96-well plates in the presence of complete DMEM/10% FBS for 24 h at 37° C. Phage antibody binding patterns were analyzed by automated fluorescent microscopy (FIG. 2B). A broad range of patterns of cell-associated phages was observed but internalization could not be clearly determined (FIG. 10). Image-based quantitation of phage binding was performed to generate a mean fluorescence intensity (MFI) value for each phage antibody (FIG. 2C). We selected the top 25% (MFI >250, 000) or 360 phage clones for more detailed analysis of internalizing properties (FIG. 2C). FACS analysis of a fraction of these phage clones on DU145 cells yielded MFI values consistent with the microscopic imaging-based analysis (FIG. 11).

HCA Identifies Phage Antibodies that Internalize Via Macropinocytosis

Figure 12:
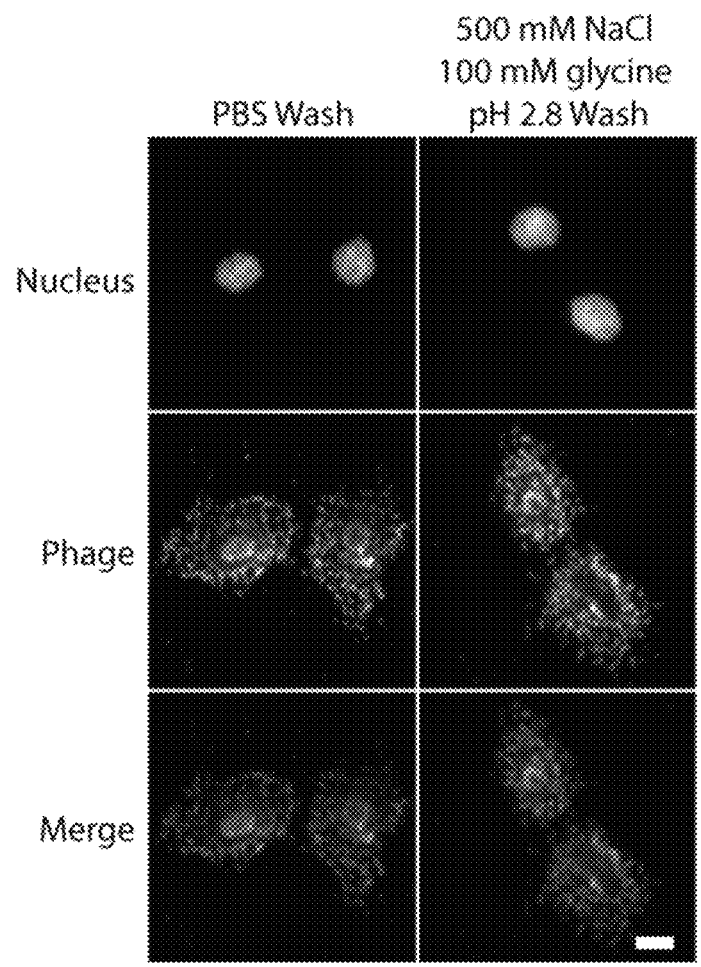
FIG. 12 shows resistance to high-salt, low-pH glycine buffer washes by cell surface-bound phage antibodies. DU145 cells were first fixed and then incubated with phage-containing supernatants, followed by washes with a pH 2.8 buffer containing 500 mM NaCl and 100 mM glycine. Phages were immunolabeled using biotin-labeled rabbit anti-fd antibodies followed by streptavidin-cy3 (pseudo-colored as green). Nuclei were stained with Hoechst 33342. Scale bar: 20 µm.

Previous methods to select and screen for internalizing phage antibodies have utilized low pH, high salt washes in an attempt to strip surface-bound phage antibodies. While this approach can be successful, strong binding, high-affinity phage antibodies may be resistant to even these harsh conditions. Several of the strongest binding phage antibody clones were tested on fixed cells, which are incapable of internalization, and found that binding was resistant to low pH, high salt washes (FIG. 12). Thus, new methods are required to identify high affinity internalizing phage antibodies.

Figure 3:
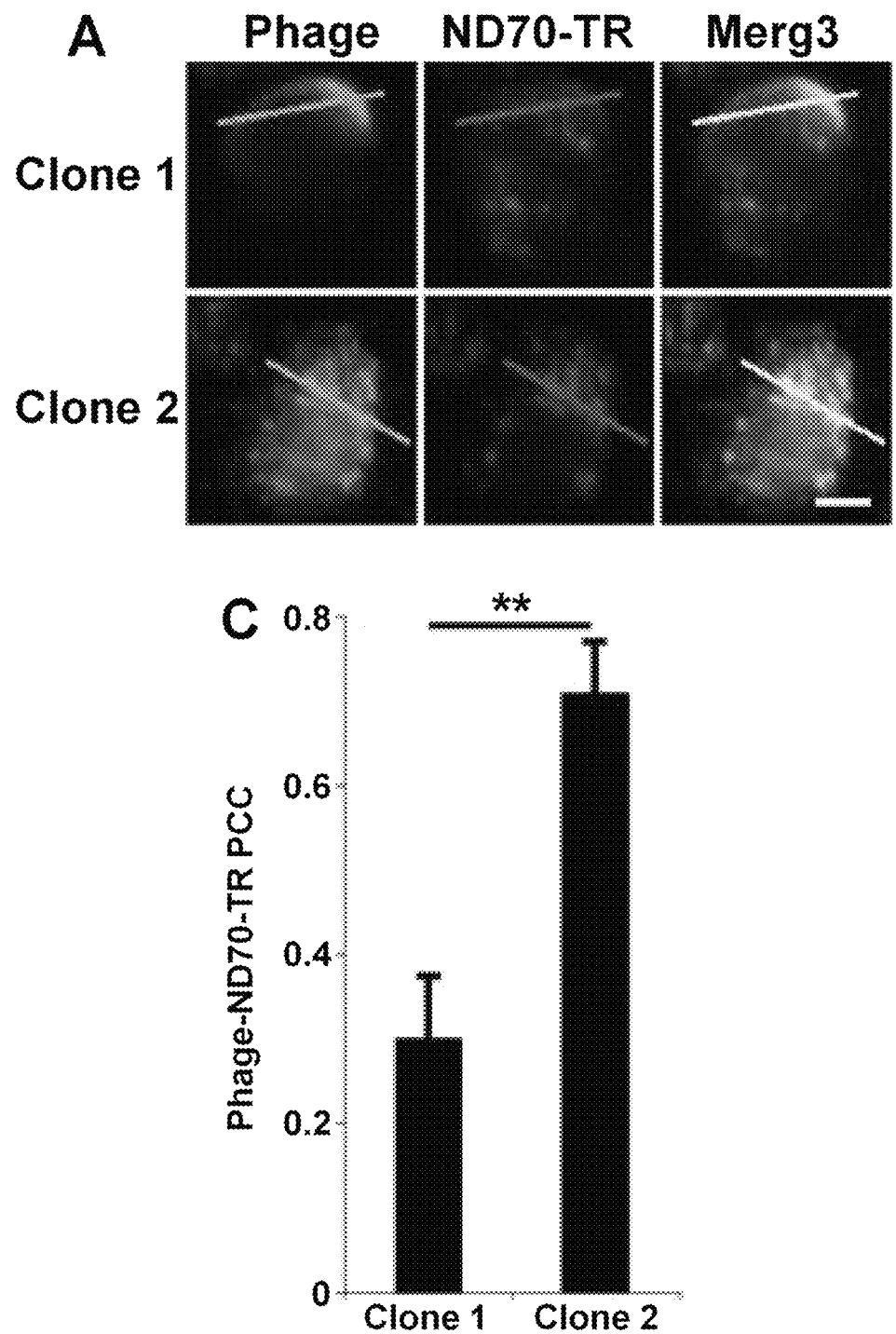
FIG. 3, panels A-E show colocalization of phage antibodies with the macropinocytosis marker ND70-TR. Panel A) Epifluorescent images of DU145 cells that were incubated with phage-containing supernatants and 50 µg/ml ND70-TR (red) for 24 h at 37° C. Cell-associated phage were then detected by biotin-labeled anti-fd antibody followed by streptavidin-AlexaFluor 488 (green). Colocalization results in color overlap (yellow). Panel B) To analyze colocalization, arbitrary lines were drawn across cells and fluorescent intensities along the drawn line were plotted for phages (green) and ND70-TR fluorescence (red). Co-variation of line intensity indicates colocalization. Representative images of two different phage antibodies with differing colocalization patterns are shown. Panel C) Pearson's correlation coefficient (PCC) was quantified and averaged from >30 cells per phage conditions. Error bars denote SEM for n=3; * and ** indicate P-values of <0.05 and <0.01, respectively, using two-tailed student's T-tests assuming unequal variance. Scale bar denotes 20 µm. Panel D) Colocalization screening. DU145 cells were plated onto 96-well plates and incubated with phages and ND70-TR (red) for 24 h at 37° C. Cells were immunolabeled against bacteriophages (green) and nuclei were stained with Hoechst 33342 (blue). Panel E) Mean PCC between immunolabeled phage and ND70-TR of 360 phage clones, quantified from minimum of 300 cells per phage clone. PCC values were normalized to control phage clones that exhibited poor internalization. Green horizontal line represents 200% of control, a threshold for further analysis.

To screen for phage antibody clones that internalize into DU145 cells via macropinocytosis, we performed HCA on the strongest binding clones (top 25%, or 360) utilizing ND70-TR as a fluid-phase macropinocytic marker (Schnatwinkel et al. (2004) PLoS Biol. 2: E261; Veithen et al. (1998) J. Cell Sci. 111(Pt 16): 2329-2335). Previous studies have established that fluorescent high molecular weight dextrans can be used to label macropinosomes (Schnatwinkel et al. (2004) PLoS Biol. 2: E261). Phage antibody-containing supernatants were co-incubated with ND70-TR over DU145 cells in culture media for 24 h at 37° C. Following washing, fixing and permeabilization, cell-associated phage were detected by anti-phage antibody, and subjected to HCA to assess colocalization with ND70-TR (FIG. 3, panel D). An initial image analysis revealed that some phage antibodies internalized into cells and colocalized with ND70-TR, primarily in juxtanuclear structures, while other clones exhibited poor colocalization with ND70-TR (FIG. 3, panels A, B). Next, a quantitative analysis was performed by measuring the Pearson's correlation coefficient (PCC) between immunolabeled phage and ND70-TR fluorescence. High PCC values identified phage antibodies that exhibited strong colocalization with ND70-TR, while low PCC values identified phage antibodies that exhibited poor colocalization with ND70-TR (FIG. 3, panel C). About 10%, or 36 clones, possessed greater than 2-fold PCC values when compared to controls (FIG. 3, panel E). Following sequencing, 14 unique antibody sequences were identified from the 36 clones.

Endocytosed Phages Macropinocytose En Route to Lysosomes in DU145 Cells

Figure 4:
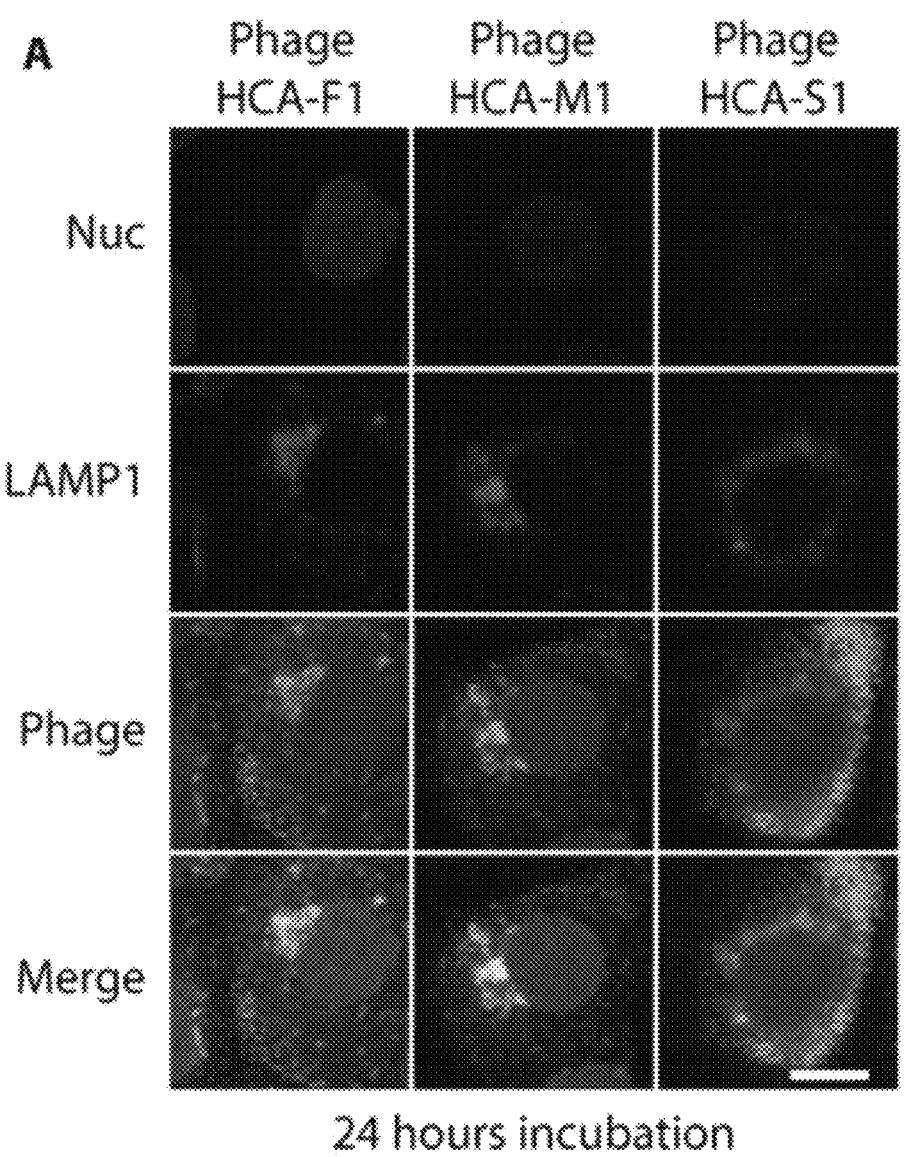
FIG. 4, panels A-C show confocal analysis of phage antibody internalization by DU145 cells. Confocal Z-slices of DU145 cells incubated with purified phage for Panel A) 24 h at 37° C. or Panel B) 8 h at 37° C. in the presence of ND70-TR. Cells were immunolabeled against phages (green), lysosomes (LAMP1, red), and nuclei (Hoechst 33342, blue). Scale bar: 20 µm. Panel C) Mean PCC of internalized phages and ND70-TR. Over 30 cells were analyzed per phage antibody. ** denotes two-tailed t-test P-values of <0.01. Error bars represent SEM for n=3.

We further characterized three phage antibody clones, named HCA-F1, HCA-M1, and HCA-S1, two of which possessed high (HCA-F1 and HCA-M1, >2-fold PCC values over control) and one with low (HCA-S1, <2-fold PCC value over control) correlation between immunolabeled phages and ND70-TR. Using fluorescent confocal microscopy, it was determined whether these clones could internalize into juxtanuclear structures coinciding with lysosomal markers. After 24 h incubation with DU145 cells, phage antibodies colocalized with lysosomal-associated membrane protein 1 (LAMP1). Phages HCA-F1 and HCA-M1 were visible as compact, vesicular structures present in a juxtanuclear area while phage HCA-S1 exhibited poor internalization (FIG. 4, panel A). Computed 3D tomography also demonstrated that endocytosed phage HCA-F1 colocalized with internalized ND70-TR. It was also determined whether phages could be visualized within early endosomes during early stages of endocytosis, however, phages did not colocalize with the endosomal marker, early endosomal antigen 1 (EEA1) (data not shown), suggesting that either the phages transited quickly through early endosomes or bypassed the early endosomes in route to lysosomes.

Phage Macropinocytose into DU145 Cells with Varying Kinetics

It was next determined whether phage antibodies HCA-F1, HCA-M1, and HCA-S1 can exhibit distinguishable internalization kinetics. Whereas two phage antibodies HCA-F1 and HCA-M1 displayed a similar internalization pattern after a 24 h incubation, only phage HCA-F1 was capable of internalizing into DU145 cells after an 8 h incubation (FIG. 4, panel B). PCC analysis between fluorescently immunolabeled, internalized phages and ND70-TR after an 8 h incubation showed significant differences between the three phage antibodies (FIG. 4, panel C). Mander's correlation coefficient analysis, which is similar to PCC analysis but places weight on fluorescent intensity, also corroborated these differences (data not shown).

Internalization of IgGs Derived from scFvs

Figure 5:
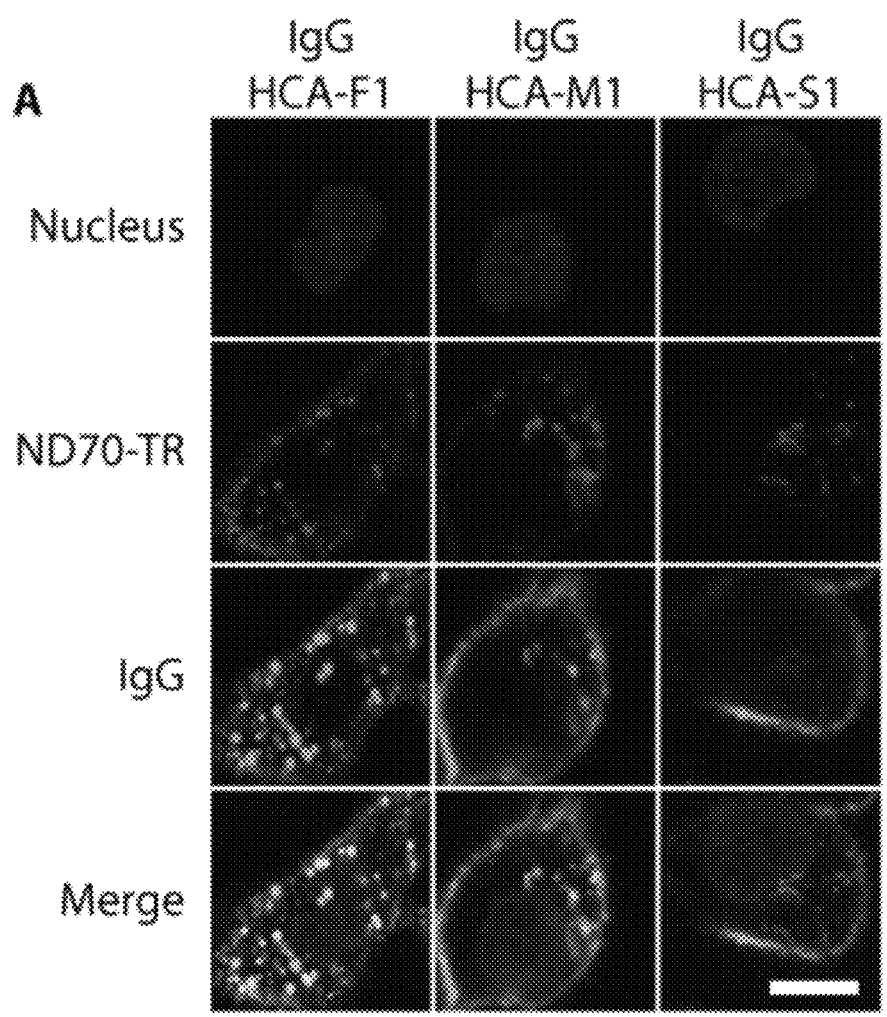
FIG. 5, panels A-B, show internalization and colocalization analysis of IgGs derived from scFvs. Panel A) DU145 cells co-incubated with three IgGs with different internalization properties at 10 µg/ml and 50 µg/ml ND70-TR (red) for 90 min at 37° C. Cells were immunolabeled against IgG using anti-human Fc (green). Nuclei were stained with Hoechst 33342 (blue). Single confocal Z-slice images are shown. Scale bar: 20 µm. Panel B) PCC analysis of colocalization of IgGs HCA-F1, HCA-M1, and HCA-S1 with ND70-TR using Z-slices crossing the entire cell, quantitating a minimum of 10 cells.  and * denote two-tailed t-test P-values of <0.01 and <0.001, respectively. Error bars represent SEM for n=3.
Figure 13:
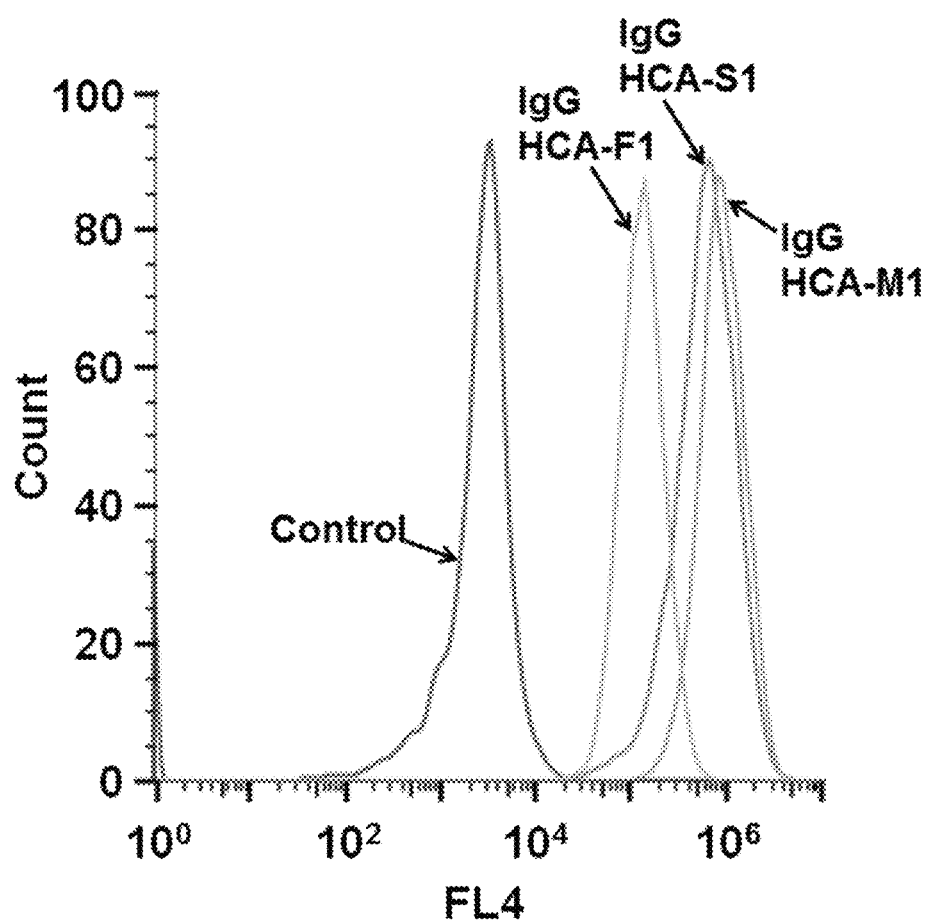
FIG. 13 show results of quality control studies: IgGs derived from scFv bind to DU145 cells. FACS analysis of DU145 cells incubated with IgG HCA-F1, HCA-M1, and HCA-S1 at 10 µg/ml for 90 min at RT. Cell-bound IgGs were detected by anti-human Fc secondary antibody conjugated with AlexaFluor 647.

ScFv from phages HCA-F1, HCA-M1, and HCA-S1 were cloned into full-length human IgG1 expression constructs and purified IgGs from transiently transfected human embryonic kidney (HEK) 293A cell supernatants. The purified IgGs HCA-F1, HCA-M1, and HCA-S1 demonstrated binding to DU145 cells via flow cytometry (FIG. 13) and colocalized with internalized ND70-TR in DU145 cells in a similar fashion to their parental phage antibodies (FIG. 5, panel A). 3D computed tomography showed that IgG HCA-F1 possesses the most robust internalization properties, internalizing almost immediately upon incubation with cells and yielding very low amounts of detectable IgG on the surface of the cell after 90 minutes of incubation. Similar to the data from the phage experiments, the PCC value between immunolabeled IgG and ND70-TR was significantly higher for IgG HCA-F1 than either IgG HCA-M1 or IgG HCA-S1 (FIG. 5, panel B).

Figure 6:
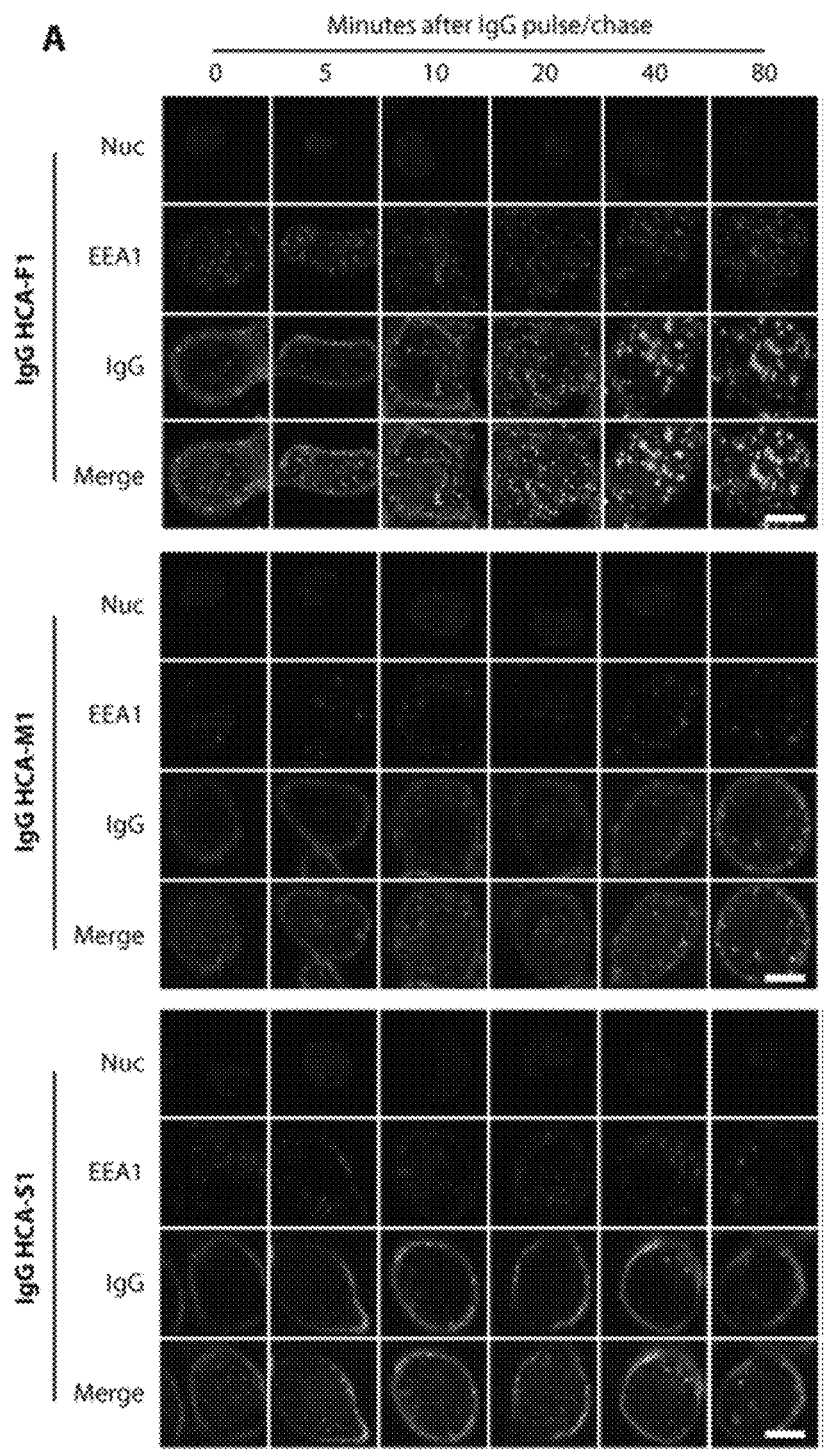
FIG. 6, panels A-D show kinetics of antibody internalization and subcellular localization. DU145 cells were incubated with three different IgGs (HCA-F1, HCA-M1, or HCA-S1) at 10 µg/ml for 15 min at 4° C. and then chased with complete DMEM/10% FBS for indicated time periods. Cells were then fixed, permeabilized and immunolabeled against human IgG (green) and Panel A) early endosomes (EEA1, red) or Panel B) lysosomes (LAMP1, red). Nuclei were stained with Hoechst 33342 (blue). Scale bar: 20 µm. Pearson's correlation coefficients between immunolabeled Panel C) EEA1 or Panel D) LAMP1 and immunolabeled IgG were averaged from a minimum of 30 cells. Error bars denote SEM of n=3.
Figure 14:
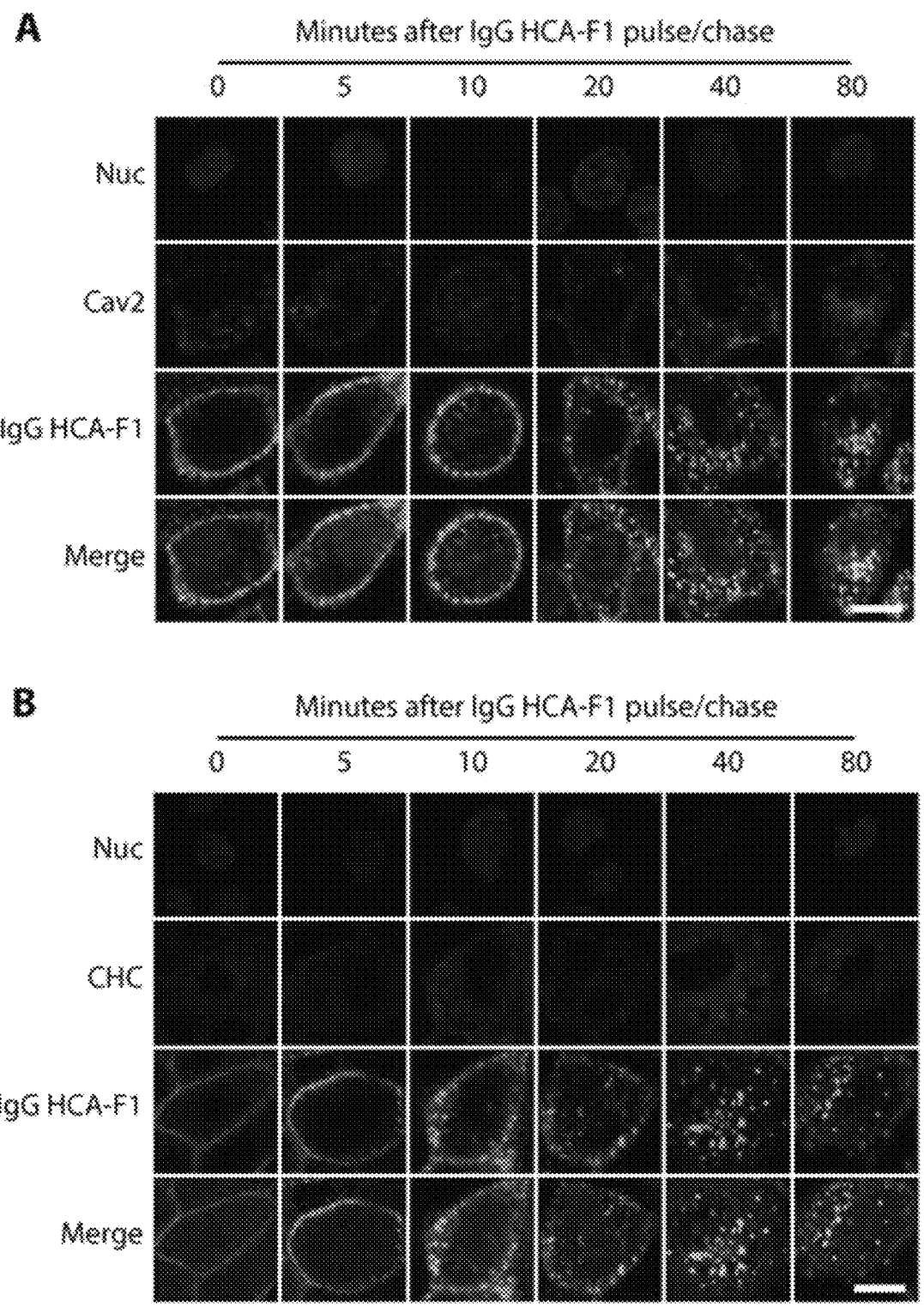
FIG. 14, panels A-B, shows that IgG HCA-F1 does not significantly colocalize with caveolin or clathrin heavy chain. DU145 cells pulsed with 10 µg/ml IgG HCA-F1 (green) in complete DMEM/10% FBS for 30 min at 4° C. were chased with 37° C. DMEM/10% FBS and fixed at varying time points. Cells were immunolabeled for organelles (red) Panel A) caveolin (Cav2) and Panel B) clathrin heavy chain (CHC). Nuclei were stained with Hoechst 33342. Single confocal Z-slices are shown. Scale bar: 20 µm.
Figure 15:
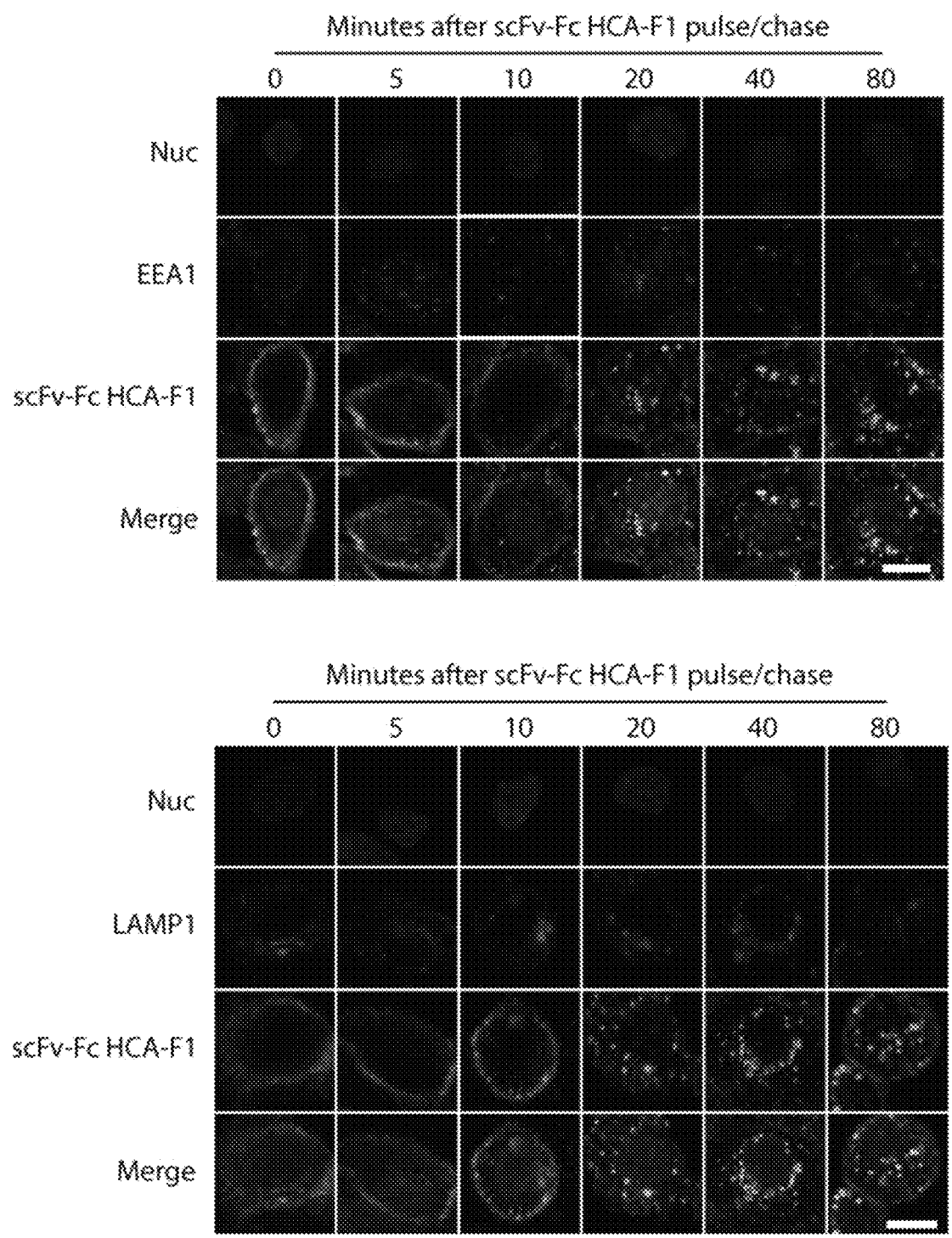
FIG. 15 shows that ScFv-Fc HCA-F1 internalizes and colocalizes with early endosomes and lysosomes in DU145 cells. DU-145 cells pulsed with 10 µg/ml scFv-Fc HCA-F1 for 30 min at 4° C. were then chased with 37° C. pre-warmed media and fixed at varying time points. Cells were immunolabeled against scFv-Fc HCA-F1 (green) and intracellular organelles (red), including early endosomes (EEA1) and lysosomes (LAMP1). Nuclei were stained with Hoechst 33342. Single confocal Z-slices are shown. Scale bar: 20 µm.

Immunolabeling against the endocytic markers EEA1 and LAMP1 was utilized to examine the colocalization of IgGs HCA-F1, HCA-M1, and HCA-S1 with early endosomes and lysosomes over varying time intervals. All of the IgGs bound to the surface of DU145 cells almost immediately after administration (FIG. 6, panels A-B). IgG HCA-F1 fluorescence increased in intensity over time in punctate-like structures at the expense of cell surface fluorescence (FIG. 6, panels A-B). IgG HCA-F1 addition also led to increased numbers of EEA1-labeled punctate structures when compared to either IgGs HCA-M1 or -S1 (FIG. 6, panel A). Antibody colocalization with both organelles was quantitated via PCC analysis across all time points. IgG HCA-F1 possessed significantly higher PCC values at earlier time points for both EEA1 and LAMP1 when compared to either IgG HCA-M1 or HCA-S1 (FIG. 6, panels C-D). IgG HCA-F1 did not significantly colocalize with caveolin-2 or clathrin heavy chain, especially at earlier time points (FIG. 14). Furthermore, the HCA-F1 scFv-Fc fusion also bound, internalized, and colocalized with both EEA1 and LAMP1 within DU145 cells in the same fashion as its IgG counterpart (FIG. 15).

IgG HCA-F1 Internalizes Via Macropinocytosis

Figure 7:
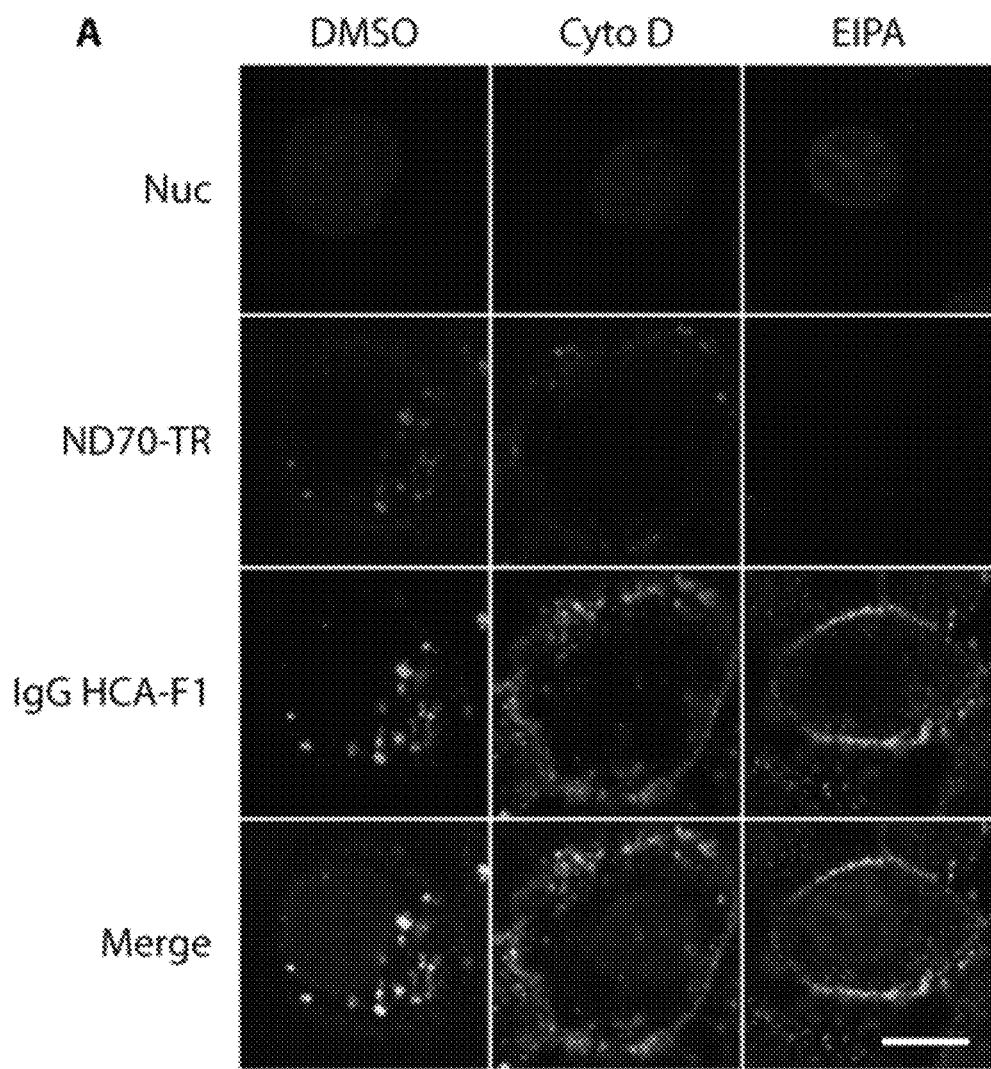
FIG. 7, panels A-B show that macropinocytosis inhibitors prevent internalization of IgG HCA-F1. DU145 cells were pre-treated with 50 µg/ml cytochalasin D, 7.5 µg/ml EIPA, or DMSO (control) for 30 min at 37° C. followed by co-incubation with 10 µg/ml IgG HCA-F1 and ND70-TR (red) in the presence of cytochalasin D, EIPA, or DMSO in complete DMEM/10% FBS for 40 min at 37° C. Cells were then immunolabeled for human IgG (green). Nuclei were stained with Hoechst 33342 (blue). Panel A) Individual confocal Z-slices of representative cells. CytoD: cytochalasin D. Scale bar: 20 µm. Panel B) The percentage of internalized IgG HCA-F1 was quantitated by measuring the ratio of internalized, cytosolic IgG HCA-F1 fluorescence over total cell IgG HCA-F1 fluorescence, analyzing >15 cells over 3 independent experiments. CytoD: cytochalasin D. *** indicates P-value of <0.001 using two-tailed student's T-test assuming unequal variance. Error bars represent SEM with n=3.

To confirm antibody internalization via macropinocytosis, antibody internalization was studied with and without inhibitors of macropinocytosis. Previous studies have demonstrated that cytochalasin D and ethylisopropylamiloride (EIPA) both inhibit macropinocytosis (Commisso et al. (2013) Nature. 497: 633-637; Gold et al. (2010) PLoS One. 5: el 1360; Veithen et al. (1996) J Cell Sci. 109(Pt 8): 2005-2012; West et al. (1989) J Cell Biol. 109: 2731-2739). DU145 cells pre-treated with cytochalasin D, EIPA, or DMSO for 30 min were chased with IgG HCA-F1 in the presence of drug or DMSO. Both cytochalasin D and EIPA significantly inhibited IgG HCA-F1 internalization into DU145 cells (FIG. 7, panel A). Measurements of internalized, immunolabeled IgG HCA-F1 fluorescence showed that both cytochalasin D and EIPA decreased endocytosed IgG HCA-F1 by >50% when compared to DMSO control (FIG. 7, panel B).

EphA2 Identified as Antigen Target for Macropinocytosing IgG HCA-F1

Figure 8:
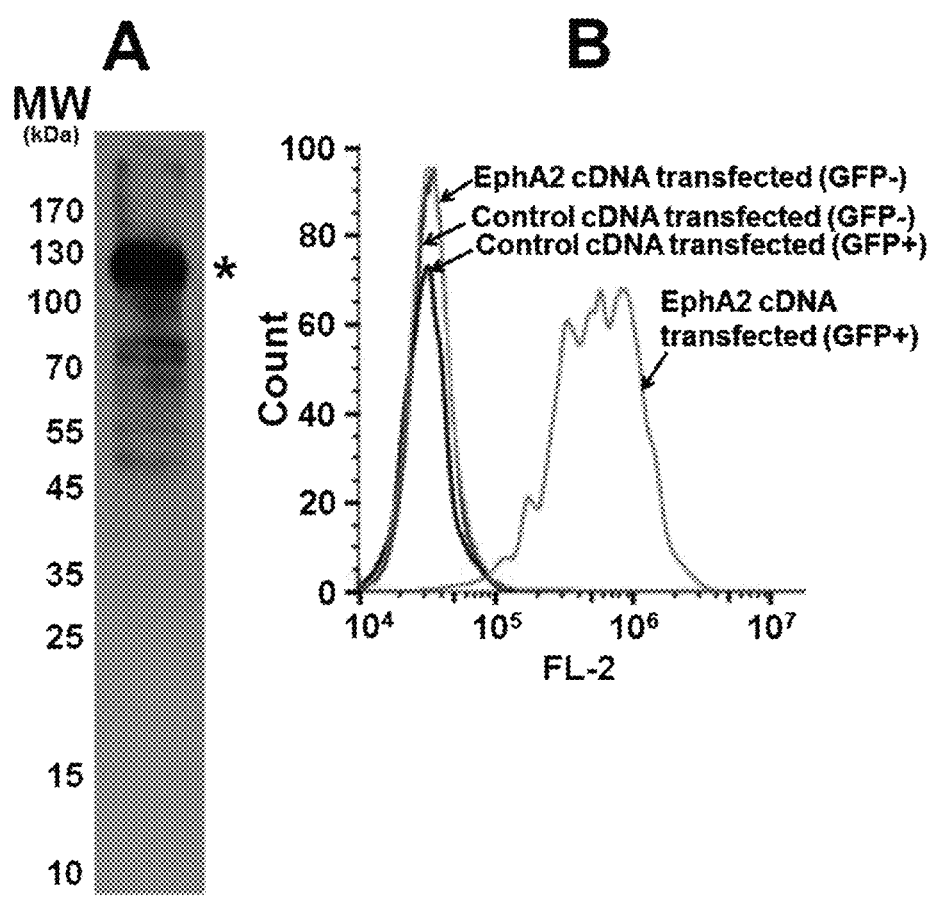
FIG. 8, panels A-C, show EphA2 identified as target antigen bound by macropinocytosing antibody IgG HCA-F1. Panel A) Immunoprecipitation of the target antigen from surface-biotinylated Du145 whole cell lysates using scFv HCA-F1-Fc fusion immobilized onto a solid matrix. The immunoprecipitation product was run on SDS-PAGE and subjected to Western blot analysis using streptavidin-HRP to locate the position of membrane proteins. The dominant band, denoted by "*", represents the approximate region from which the corresponding SDS-PAGE gel was extracted for mass spectrometry analysis. Panel B) Binding to ectopically expressed EphA2. Chinese hamster ovarian (CHO) cells were co-transfected with pEGFP-N2 (to label transfected cells) and pCMV6 expression constructs bearing either human EphA2 or Lgr5 (control). Cells were then incubated with IgG HCA-F1, followed by immunolabeling using anti-human Fc AlexaFluor 647. Cells were gated for GFP expression and plotted for AlexaFluor 647 fluorescence (FL4). Panel C) Plot of MFI values as analyzed by FACS. IgG HCA-F1 binds specifically to ectopically expressed EphA2, confirming the target identification.

We next sought to determine the target antigen bound by the rapidly interalizing macropinocytosing IgGHCA-FT. We surface-biotinylated DU145 cells, prepared cell lysates and performed immunoprecipitation with HCA-FT scFv-Fc immobilized to agarose beads. Immunoprecipitation products underwent parallel SDS-PAGE and immunoblotting. Immunoblotting results with streptavidin-conjugated horseradish peroxidase (HRP) showed a dominant band at ~110 kDa (FIG. 8, panel A). After excising the corresponding band from the Coomassie-stained gel, the extracted protein gel slice underwent trypsin-digestion and analysis via tandem mass spectrometry. The results identified a transmembrane protein, ephrin type-A receptor 2 (EphA2), as the target antigen (Table 2). For an independent verification, we ectopically expressed human EphA2 cDNA in Chinese hamster ovary (CHO) cells and found that IgG HCA-F1 bound strongly to these cells but not CHO cells transfected with a control cDNA (FIG. 8, panels B-C).

TABLE 2

EphA2 identified as the target antigen for IgG HCA-F1.

| Protein Name | Gene Name | Accession # | Size (kDa) | Unique Peptides Detected | Sequence Coverage % |
|---|---|---|---|---|---|
| Ephrin type_A receptor 2 precursor | EPHA2 | NP_004422 | 108 | 47 | 44 |

TABLE 3

Mass spectrometry analysis identify peptides of EphA2.

| Sequence | Sequest XCorr | Seqest delta Cn | Modifications | Observed | Actual Mass | Ch rg | Delta Da (x 10$^{-3}$) | Delta PPM | TIC | Strt/ Stp |
|---|---|---|---|---|---|---|---|---|---|---|
| (R)DcNS FPGGAS ScK(E) (SEQ ID NO: 11) | 2.6496 | 0.4959 | Carbamid omethyl (+57), Carbamid omethyl (+57) | 693.77 | 1,385.53 | 2 | -2.477 | -1.79 | 128 849 | 104/ 116 |
| (R)DcNS FPGGAS ScK(E) (SEQ ID NO: 11) | 2.1481 | 0.4668 | Carbamid omethyl (+57), Carbamid omethyl (+57) | 693.77 | 1,385.53 | 2 | -3.677 | -2.65 | 20, 897.20 | 104/ 116 |
| (R)DcNS FPGGAS ScK(E) (SEQ ID NO: 11) | 1.9465 | 0.441 | Carbamid omethyl (+57), Carbamid omethyl (+57) | 693.77GV | 1,385.53 | 2 | -4.177 | -3.01 | 15, 624.10 | 104/ 116 |
| (R)mHc AVDGE WLVPI GQcLcQ AGYEK (V) (SEQ ID NO: 12) | 4.623 | 0.529 | Oxidation (+16), Carbamid omethyl (+57), Carbamid omethyl (+57), Carbamid omethyl (+57) | 946.42 | 2,836.24 | 3 | -2.457 | -0.87 | 67, 765.50 | 245/ 268 |
| (R)MHc AVDGE WLVPI GQcLcQ AGYEK (V) (SEQ ID NO: 12) | 3.1364 | 0.575 | Carbamid omethyl (+57), Carbamid omethyl (+57), Carbamid omethyl (+57) | 941.0 | 2,820.25 | 3 | -4.442 | -1.57 | 31, 426.50 | 245/ 268 |
| (K)VED AcQAcS PGFFK (F) (SEQ ID NO: 13) | 2.4311 | 0.422 | Carbamid omethyl (+57), Carbamid omethyl (+57) | 808.35 | 1,614.68 | 2 | 0.5234 | 0.32 | 79, 332.10 | 269/ 282 |
| (K)VED AcQAcS | 2.3217 | 0.325 | Carbamid omethyl | 808.35 | 1,614.68 | 2 | -2.077 | -1.29 | 54, 619.60 | 269/ 269 |

TABLE 3-continued

Mass spectrometry analysis identify peptides of EphA2.

| Sequence | Sequest XCorr | Seqest delta Cn | Modifications | Observed | Actual Mass | Chrg | Delta Da (x 10⁻³) | Delta PPM | TIC | Strt/Stp |
|---|---|---|---|---|---|---|---|---|---|---|
| PGFFK (F) (SEQ ID NO: 14) | | | (+57), Carbamidomethyl (+57) | | | | | | | |
| (K)FEAS ESPcLEc PEHTLP SPEGAT ScEcEE GFFR(A) (SEQ ID NO: 15) | 2.3081 | 0.351 | Carbamidomethyl (+57), Carbamidomethyl (+57), Carbamidomethyl (+57), Carbamidomethyl (+57), Carbamidomethyl (+57) | 1282.86 | 3,845.55 | 3 | -9.907 | -2.58 | 33, 332.00 | 283/284 |
| (R)YSEP PHGLT R(T) (SEQ ID NO: 16) | 2.2298 | 0.306 | | 386.20 | 1,155.57 | 3 | -2.346 | -2.03 | 73, 404.30 | 385/394 |
| (R)YSEP PHGLT R(T) (SEQ ID NO: 16) | 2.3917 | 0.330 | | 578.79 | 1,155.57 | 2 | -2.146 | -1.86 | 113 986 | 385/394 |
| (R)YSEP PHGLT R(T) (SEQ ID NO: 16) | 2.1526 | 0.357 | | 578.79 | 1,155.57 | 2 | -1.646 | -1.42 | 45, 566.90 | 385/394 |
| (R)YSEP PHGLT R(T) (SEQ ID NO: 16) | 2.2759 | 0.257 | | 386.20 | 1,155.57 | 3 | -0.746 | -0.65 | 63, 530.60 | 385/394 |
| (R)YSEP PHGLT R(T) (SEQ ID NO: 16) | 2.0678 | 0.344 | | 578.79 | 1,155.57 | 2 | 0.354 | 0.31 | 47, 981.3 | 385/394 |
| (R)YSEP PHGLT R(T) (SEQ ID NO: 16) | 2.0638 | 0.280 | | 386.20 | 1,155.57 | 3 | -2.246 | -1.94 | 494 067 | 385/394 |
| (R)YSEP PHGLT R(T)* (SEQ ID NO: 16) | 2.2515 | 0.195 | | 386.20 | 1,155.57 | 3 | -0.546 | -0.47 | 122 285 | 385/394 |
| (R)YSEP PHGLT R(T)** (SEQ ID NO: 16) | 1.9858 | 0.188 | | 386.20 | 1,155.57 | 3 | -2.246 | -1.94 | 207 445 | 385/394 |
| (R)NGV SGLVTS R(S) (SEQ ID NO: 17) | 2.8737 | 0.443 | | 495.27 | 988.5277 | 2 | -2.446 | -2.47 | 314 423 | 416/425 |

TABLE 3-continued

Mass spectrometry analysis identify peptides of EphA2.

| Sequence | Sequest XCorr | Seqest delta Cn | Modifications | Observed | Actual Mass | Chrg | Delta Da (x 10$^{-3}$) | Delta PPM | TIC | Strt/ Stp |
|---|---|---|---|---|---|---|---|---|---|---|
| (R)TAS VSINQT EPPK(V) ** (SEQ ID NO: 18) | 1.4272 | 0.314 | | 686.36 | 1,370.70 | 2 | -3.146 | -2.29 | 31, 114.50 | 429/ 441 |
| (R)TAS VSINQT EPPKVR (L) (SEQ ID NO: 19) | 3.0843 | 0.502 | | 813.94 | 1,625.86 | 2 | -9.146 | -5.62 | 48, 697.80 | 429/ 443 |
| (R)TAS VSINQT EPPKVR (L) (SEQ ID NO: 20) | 2.6076 | 0.324 | | 542.96 | 1,625.87 | 3 | -6.946 | -4.27 | 263 | 429/ 443 |
| (R)STTS LSVSW SIPPPQ QSR(V) (SEQ ID NO: 20) | 2.7719 | 0.421 | | 979.50 | 1,956.99 | 2 | -0.246 | -0.13 | 51, 078.80 | 448/ 465 |
| (R)STTS LSVSW SIPPPQ QSR(V)* ** (SEQ ID NO: 21) | 2.0494 | 0.262 | | 979.50 | 1,956.99 | 2 | 1.254 | 0.64 | 25, 873.20 | 448/ 465 |
| (R)VWK YEVTY R(K) (SEQ ID NO: 21) | 2.0319 | 0.262 | | 415.22 | 1,242.64 | 3 | -2.246 | -1.81 | 130 884 | 466/ 474 |
| (R)KKG DSNSY NVR(R) (SEQ ID NO: 22) | 2.8284 | 0.407 | | 634.32 | 1,266.63 | 2 | 0.254 | .20 | 27, 676.30 | 475/ 485 |
| (R)KKG DSNSY NVR(R) (SEQ ID NO: 23) | 1.6464 | 0.265 | | 423.2 | 1,266.63 | 3 | -0.746 | -0.59 | 42 355.60 | 475/ 485 |
| (R)QSPE DVYFS K(S) (SEQ ID NO: 23) | 2.3752 | 0.348 | | 600.28 | 1,198.55 | 2 | 1.454 | 1.21 | 189 723 | 569/ 578 |
| (K)FTTE IHPScV TR(Q) (SEQ ID NO: 24) | 3.0577 | 0.408 | Carbamid omethyl (+57) | 724.35 | 1,446.69 | 2 | -0.6113 | -0.42 | 160 757 | 604/ 615 |
| (K)FTTE IHPScV TR(Q)** * (SEQ ID NO :25) | 2.2528 | 0.213 | Carbamid omethyl (+57) | 483.24 | 1,446.69 | 3 | -0.7113 | -0.49 | 262 928 | 604/ 615 |

TABLE 3-continued

Mass spectrometry analysis identify peptides of EphA2.

| Sequence | Seqest XCorr | Seqest delta Cn | Modifi- cations | Observed | Actual Mass | Ch rg | Delta Da (x 10$^{-3}$) | Delta PPM | TIC | Strt/ Stp |
|---|---|---|---|---|---|---|---|---|---|---|
| (R)QKVI GAGEF GEVYK (G) (SEQ ID NO: 25) | 1.9156 | 0.398 | | 762.91 | 1,523.80 | 2 | 2.054 | 1.35 | 35, 365.50 | 616/ 629 |
| (R)QKVI GAGEF GEVYK (G)** (SEQ ID NO: 26) | 1.8738 | 0.224 | | 508.94 | 1,523.80 | 3 | −0.346 | −0.23 | 200 820 | 616/ 629 |
| (K)VIG AGEFG EVYK (G) (SEQ ID NO: 26) | 2.5299 | 0.468 | | 634.83 | 1,267.65 | 2 | 2.154 | 1.70 | 389 857 | 618/ 629 |
| (K)QRV DFLGE AGIMG QFSHH NIIR(L) (SEQ ID NO: 27) | 4.3377 | 0.574 | | 632.08 | 2,524.28 | 4 | 5.354 | 2.12 | 65, 605.40 | 656/ 677 |
| (K)QRV DFLGE AGIMG QFSHH NIIR(L) (SEQ ID NO: 27) | 3.8947 | 0.552 | | 505.86 | 2,524.28 | 5 | 4.154 | 1.65 | 77, 030.10 | 656/ 677 |
| (K)QRV DFLGE AGImG QFSHH NIIR(L) (SEQ ID NO: 27) | 3.2965 | 0.454 | Oxidation (+16) | 509.00 | 2,540.27 | 5 | 1.139 | 0.45 | 149 402 | 656/ 677 |
| (R)VDF LGEAGI mGQFS HHNIIR (L) (SEQ ID NO: 28) | 3.1313 | 0.412 | Oxidation (+16) | 753.04 | 2,256.11 | 3 | 0.06101 | −0.03 | 54, 320.90 | 658/ 677 |
| (R)VDF LGEAGI mGQFS HHNIIR (L) (SEQ ID NO: 28) | 3.2648 | 0.380 | Oxidation (+16) | 565.0 | 2,256.11 | 4 | −1.261 | −0.56 | 98, 523.40 | 658/ 677 |
| (R)NILV NSNLVc K(V) (SEQ ID NO: 29) | 2.983 | 0.142 | Carbamid omethyl (+57) | 637.35 | 1,272.69 | 2 | 0.9887 | 0.78 | 569 450 | 744/ 754 |
| (R)VLE DDPEA TYTTSG GK(I) (SEQ ID NO: 30) | 2.6914 | 0.508 | | 841.89 | 1,681.77 | 2 | −3.146 | −1.87 | 85, 590.20 | 763/ 778 |

TABLE 3-continued

Mass spectrometry analysis identify peptides of EphA2.

| Sequence | Sequest XCorr | Seqest delta Cn | Modifications | Observed | Actual Mass | Ch rg | Delta Da (x $10^{-3}$) | Delta PPM | TIC | Strt/ Stp |
|---|---|---|---|---|---|---|---|---|---|---|
| (R)VLE DDPEA TYTTSG GK(I) (SEQ ID NO: 30) | 1.8545 | 0.422 | | 841.89 | 1,681.77 | 2 | -0.546 | -0.32 | 18, 354.50 | 763/ 778 |
| (R)VLE DDPEA TYTTSG GKIPIR (W) (SEQ ID NO: 31) | 3.3147 | 0.487 | | 721.37 | 2,161.09 | 3 | -1.246 | -0.58 | 91, 933.40 | 763/ 782 |
| (R)WTA PEAISY R(K) (SEQ ID NO:32) | 2.3826 | 0.300 | | 597.30 | 1,192.59 | 2 | 1.454 | 1.22 | 165 682 | 783/ 792 |
| (K)FADI VSILDK (L) (SEQ ID NO: 33) | 2.3497 | 0.408 | | 560.82 | 1,119.62 | 2 | -1.346 | -1.20 | 104 5020 | 864/ 873 |
| (R)VSIR LPSTSG SEGVPF R(T) (SEQ ID NO: 34) | 4.5897 | 0.550 | | 596.96 | 1,787.95 | 3 | -4.646 | -2.60 | 136 449 | 891/ 907 |
| (R)LPST SGSEG VPFR(T) (SEQ ID NO: 35) | 3.2221 | 0.440 | | 667.34 | 1,332.67 | 2 | -0.646 | -0.48 | 117 106 | 895/ 907 |
| (R)LPST SGSEG VPFR(T) (SEQ ID NO: 35) | 3.0411 | 0.451 | | 667.34 | 1,332.67 | 2 | 0.654 | 0.49 | 237 650 | 895/ 907 |
| (K)VVQ MTNDD IKR(I) (SEQ ID NO: 36) | 2.9539 | 0.429 | | 659.84 | 1,317.67 | 2 | -3.046 | -2.31 | 36, 696.70 | 936/ 946 |
| (K)VVQ mTNDD IKR(I) (SEQ ID NO: 36) | 2.3773 | 0.282 | Oxidation (+16) | 667.84 | 1,333.66 | 2 | -2.161 | -1.62 | 212 225 | 936/ 946 |
| (R)IAYS LLGLK (D)**** (SEQ ID NO: 37) | 1.9363 | 0.271 | | 489.30 | 976.5941 | 2 | -1.746 | -1.79 | 145 459 | 958/ 966 |

*Prob 99%; Prob 95%; *Prob 98%; ****Prob 99%

Receptor-Dependent Macropinocytosis of the Anti-EphA2 IgG

Figure 9:
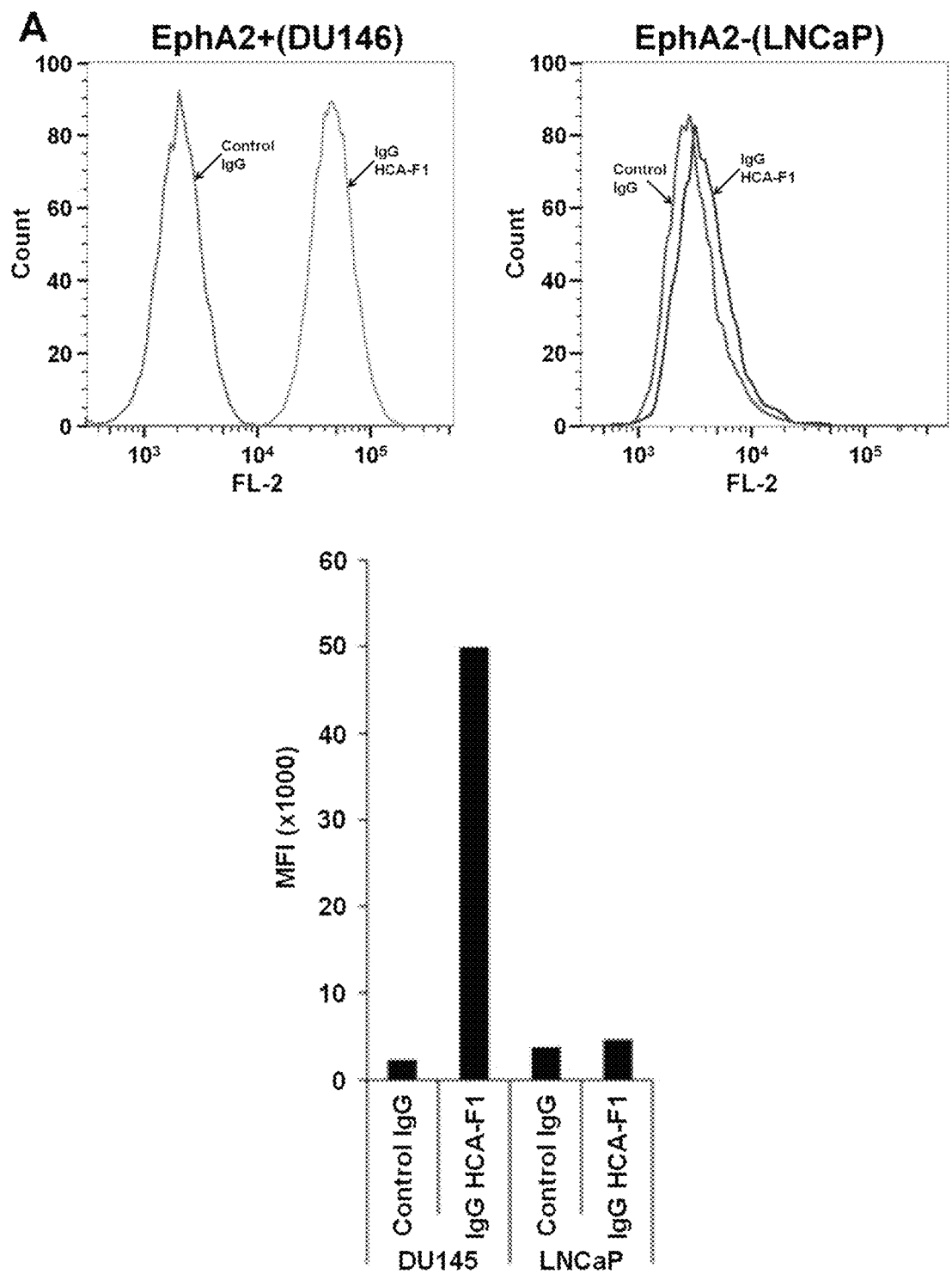
FIG. 9, panels A-B show functional internalization assay using IgG HCA-F1-toxin conjugates. Panel A) FACS analysis showing EphA2-positive (DU145) and EphA2-negative (LNCaP, control) cells. IgG HCA-F1 was incubated with the cells and binding was detected with anti-human Fc. MFI values are shown in the far right panel. Panel B) IgG HCA-F1 was conjugated to saporin and incubated with target (DU145) and control (LNCaP) cells. Controls: toxin only and IgG HCA-F1 only. Cell viability was measured 4 days later using the CCK-8 assay.
Figure 16:
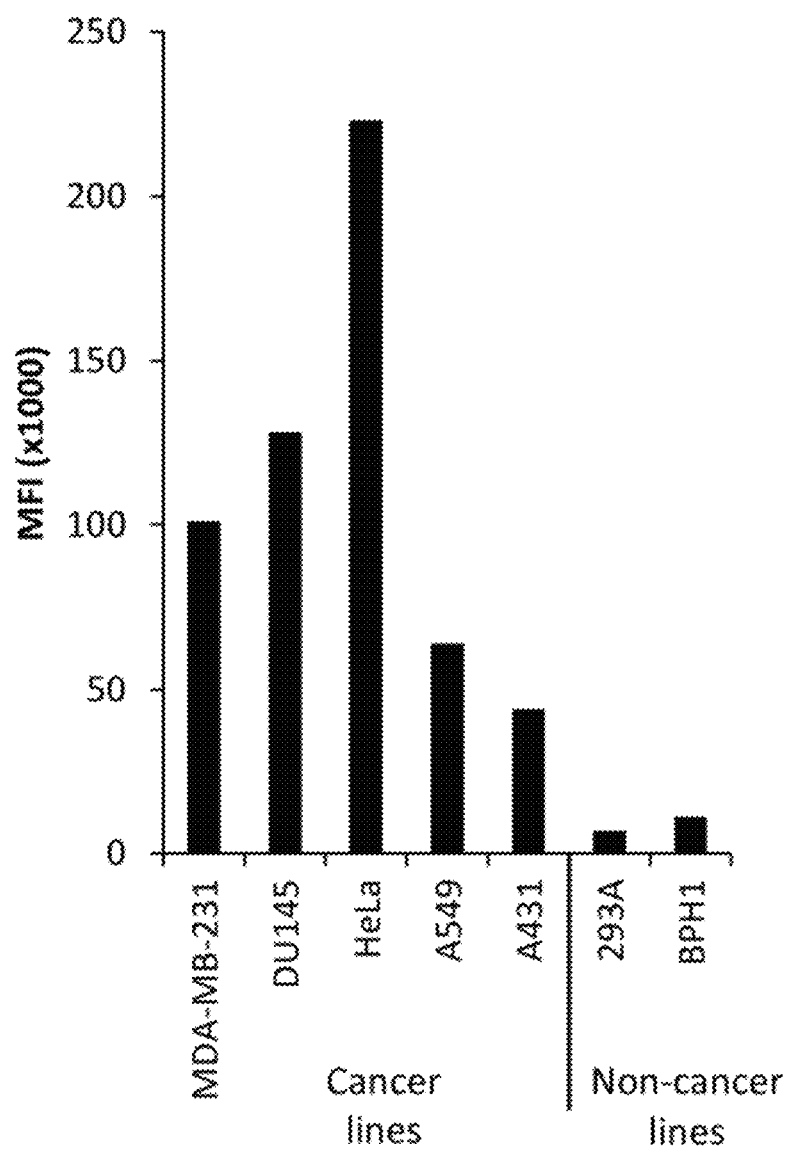
FIG. 16 shows MFI value plot showing IgG HCA-F1 binding patterns on a panel of cancer and non-cancer cell lines. Cells were incubated with 10 µg/ml IgG HCAF1, washed and bound IgG detected with anti-human Fc.
Figure 17:
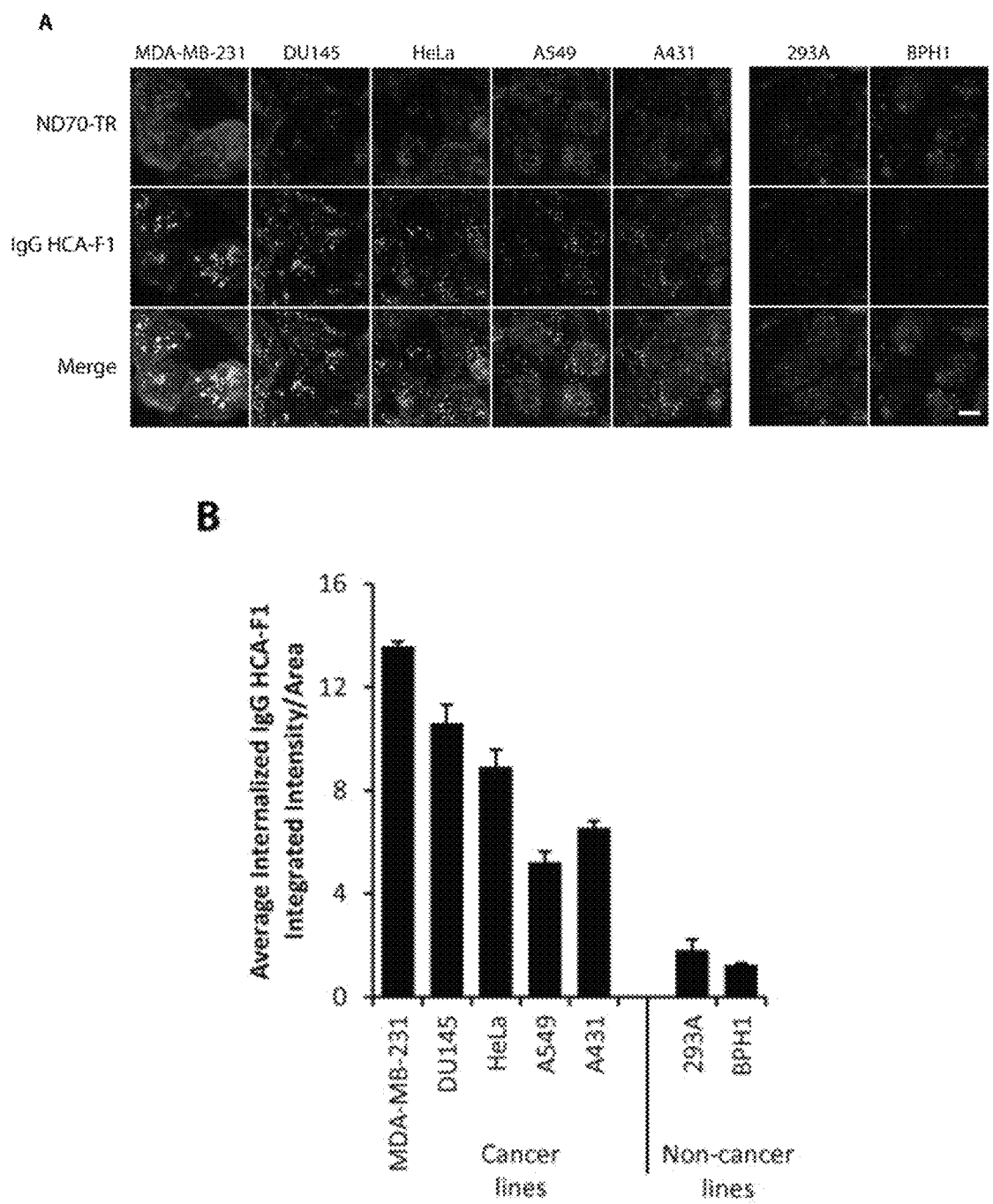
FIG. 17, panels A-B, shows that IgG HCA-F1 preferentially internalizes into cancer cell lines when compared to non-cancer cell lines. Panel A) Confocal Z-projection micrographs of various cells incubated with 10 µg/ml IgG HCA-F1 and 20 µg/ml ND70-TR for 90 min at 37° C., followed by immunolabeling against human Fc. Nuclei were stained with Hoechst 33342. The five cancer cell lines are on the left (MDA-MB-231, DU145, HeLa, A549, and A431) while the two non-cancer cell lines are on the right (293A and BPH1). Scale bar: 15 µm. Panel B) Average internalized IgG HCA-F1 integrated intensity/area for each cell line, measuring a minimum of 10 cells. Error bars denote SEM from n=3.

As EphA2 is widely overexpressed by cancer cells (Wykosky and Debinski (2008)*Mol. Cancer Res.* 6: 1795-1806; Tandon et al. (2011) *Expert Opin. Ther. Targets.* 15: 31-51), we next examined whether IgG HCA-F1 is capable of binding to other cancer cell lines and internalizing via macropinocytosis. We analyzed the binding of IgG HCA-F1 to five human cancer cell lines (prostate cancer DU145, breast cancer MDA-MB-231, lung cancer A549, cervical cancer HeLa, epidermoid carcinoma A431) and two non-cancer cell lines (Hs27 and BPH-1) by FACS. IgG HCA-F1 binding was higher for all five cancer cell lines when compared to the non-cancer cell lines (FIG. 16). IgG HCA- F1 did not bind to the LNCaP line that does not express EphA2 (FIG. 9, panel A), demonstrating the receptor-dependent nature of this type of cell entry. To assess binding to cross-species epitopes, we also performed FACS analysis of IgG HCA-F1 on a mouse melanoma cell line B16F10 and observed binding, which suggests that IgG HCA-F1 bind to an EphA2 epitope conserved across species (data not shown). To investigate the specificity of internalization, IgG HCA-F1 and ND70-TR were co-incubated over the aforementioned panel of both cancer and non-cancer cell lines. Confocal imaging using equal exposure times confirmed that IgG HCA-F1 bound strongly to cancer cell lines when compared to non-cancer cell lines (FIG. 17, panel A). Internalized IgG HCA-F1 was quantified by measuring mean fluorescent intensities of IgG HCA-F1 within individual, confocal slices of cytosolic areas of cells. Quantitation of internalized IgG HCA-F1 across all cell lines revealed that cancer cell lines possess greater amounts of internalized IgG HCA-F1 when compared to non-cancer cell lines (FIG. 17).

Antibody-Toxin Conjugate Exhibits Potent Cytotoxicity In Vitro

To obtain functional evidence for internalization, we investigated whether an IgG HCA-F1-based antibody-toxin conjugate could lead to targeted killing of tumor cells. We created an IgG HCA-F1-toxin conjugate by first modifying IgG HCA-F1 with amine-reactive biotin, followed by attachment of streptavidin-conjugated saporin, a highly potent ribosome-inactivating protein toxin. Saporin lacks a chain required for cell insertion and is thus non-toxic by itself. The antibody-toxin conjugates were incubated at varying concentrations with both DU145 (EphA2 positive) and LNCAP (EphA2-negative) cells and examined cell viability after 4 days. The IgG HCA-F1-toxin conjugate exhibited potent cytotoxicity against DU145 cells ($IC_{50}$ about 19 pM) but not on control LNCaP cells (FIG. 9, panel B), demonstrating functionally a receptor-dependent internalization mechanism. Toxin conjugated to a control nonbinding human IgG did not kill tumor cells, neither did toxin alone nor naked HCA-F1 IgG. These studies provide functional evidence for rapid internalization by our anti-EphA2 antibody IgG HCA-F1 and demonstrate potential for the development of targeted therapeutics against EphA2-positive tumors.

Discussion

Recent studies suggest that macropinocytosis is a rapid and efficient cellular internalization pathway that is upregulated selectively by tumor cells (Commisso et al. (2013) Nature. 497: 633-637; Reyes-Reyes et al. (2010) Cancer Res. 70: 8617-8629). Exploring this pathway for targeted therapy development has the potential of improving potency and selectivity for tumor targeting agents. While studies have been done previously to identify internalizing antibodies from phage antibody display libraries (Zhu et al. (2010) Mol. Cancer Ther. 9: 2131-2141; An et al. (2008) Mol. Cancer Ther. 7: 569-578; Liu et al. (2004) Cancer Res. 64: 704-710; Poul et al. (2000) J Mol. Biol. 301: 1149-1161; Rudnick et al. (2011) Cancer Res. 71: 2250-2259), no method has been developed to identify macropinocytosing antibodies. In this study, we developed an HCA-based high throughput method to identify macropinocytosing antibodies from phage antibody display libraries. Following conversion into full-length human IgG1s, we determined by confocal microscopy that one of the antibodies, IgG HCA-F1, rapidly internalizes via macropinocytosis and colocalizes with early endosome and lysosome markers. The microscopic internalization studies were confirmed by functional internalization assays based on the plant toxin saporin that lacks an internalization mechanism on its own. The rapid internalization of the HCA-F1 IgG resulted in potent cytotoxicity of antibody-toxin conjugate against a broad panel of tumor cells expressing the target antigen, demonstrating functionally that this antibody is efficiently internalized by target cells.

Previous methods to select and screen for internalizing phage antibodies have utilized low pH, high salt wash buffers in an attempt to strip away surface-bound phage antibodies (An et al. (2008) Mol. Cancer Ther. 7: 569-578; Liu et al. (2004) Cancer Res. 64: 704-710; Poul et al. (2000) J. Mol. Biol. 301: 1149-1161). While this approach has been at least partially successful, strong binding high affinity phage antibodies may be resistant to even these harsh conditions. Indeed, when we tested strong binding phage antibodies on fixed cells which are incapable of internalization, we found that binding was resistant to low pH, high salt washes. In addition, we found that analysis of patterns of cell-associated phage that were generated by non-confocal HCA instruments was not sufficient to determine if the phage is internalized. Many heterogeneous patterns were observed, and it was difficult to reliably associate any of the patterns with internalization, let alone macropinocytosis. Thus, our new methods based on multi-marker microscopic HCA establish an effective means for the identification of internalizing and furthermore macropinocytosing antibodies from phage display libraries.

Our studies showed that there are major differences in internalization kinetics between an antibody in soluble form and on phage, which must be taken into consideration for screening design. For example, when tested in full-length IgG or scFv-Fc fusion forms, the highly active macropinocytosing antibody HCA-F1 starts internalization almost immediately and completes the process in 40-80 min, while the same antibody in phage format does so in 8 h. The large size of the phage particle may have slowed down the internalization process considerably regardless of how rapidly the antibody internalizes in soluble forms. In addition, although in soluble forms different antibodies utilized disparate internalization pathways, in phage forms they seem to converge into the macropinocytosis pathway. This is not entirely surprising considering the size of the phage particle. Nonetheless, despite the generally retarded rate and the near uniform route of phage particle internalization (phage macropinocytosis), the kinetic differences in phage antibody internalization are a function of the underlying scFv, with HCA-F1-like phage internalizing in 8 h, HCA-M1-like in 24 h and HCA-S1-like >24 h. These kinetics differences allowed us to develop screening schemes to uncover rapidly internalizing antibodies such as the macropinocytosing antibody HCA-F1. In this context, we would like to re-emphasize that HCA screening using phage directly is convenient and compatible with the high throughout format, but the result must be verified using antibodies in soluble forms.

Another peculiar feature of phage internalization is revealed by our organelle-labeling experiment. While phage antibodies are seen to colocalize to lysosomes, they could not be readily seen entering cells via the early endosomal pathway. We reconciled this observation by hypothesizing that large, macropinocytosed phage particles may be trafficking via endosomes distinct from traditional coated vesicle-formed endosomes, which has been previously observed (Hewlett et al. (1994) J Cell Biol. 124: 689-703). For IgG however, we were able to observe that the phage-derived IgG could internalize via macropinocytosis towards the lysosomal organelles via the endosomal pathway.

EphA2 is known to be expressed by various tumor cells and play roles in tumor invasion and metastasis (Wykosky and Debinski (2008)*Mol. Cancer Res.* 6: 1795-1806). Several groups have developed anti-EphA2 antibodies (Ansuini et al. (2009) *J. Oncol.* 2009: 951917; Jackson et al. (2008) *Cancer Res.* 68: 9367-9374; Zhou et al. (2010) *J. Mol. Biol.* 404: 88-99), and it appears that different epitopes mediate different rates of internalization (Ansuini et al. (2009) *J. Oncol.* 2009: 951917). No phage antibody library selection scheme has been developed previously that allows for selection of macropinocytosing antibodies binding to EphA2 or other antigens. Our unbiased screening has uncovered an antibody that binds to EphA2 and is rapidly internalized by the macropinocytosis pathway, thereby creating novel agents against this receptor.

EphA2 has been the target for many forms of cancer therapy development. Nanoparticles conjugated with anti-EphA2 antibodies have been used for siRNA delivery (Shen et al. (2013) *Clin. Cancer Res.* 19: 1806-1815; Tanaka et al. (2010) *Cancer Res.* 70: 3687-3696). In addition, an anti-EphA2 antibody auristatin E conjugate was tested in a phase I trial for solid tumor treatment (Jackson et al. (2008) *Cancer Res.* 68: 9367-9374; Annunziata et al. (2013) *Invest. New Drugs.* 31: 77-84). This particular anti-EphA2 antibody-auristatin E-conjugate showed unacceptably high toxicity at sub-therapeutic doses (Annunziata et al. (2013) *Invest. New Drugs.* 31: 77-84). Given that different EphA2 epitopes distinctly influence the kinetics and pathway of internalization, it is possible that the aforementioned setback with the anti-EphA2 antibody-auristatin E-conjugate is an isolated phenomenon relating to the particular antibody used. In any event, anti-EphA2 antibodies can be utilized to deliver payloads other than auristatin. As such there still could be further development of an anti-EphA2 antibody-based therapeutic in the future. Our anti-EphA2 antibody is internalized by the tumor selective macropinocytosis pathway, and may thus have a different potency/toxicity profile than those previously reported EphA2 targeting agents. Given that the macropinocytosing epitope bound by our HCA-F1 antibody is conserved across species, any targeted therapeutics developed from this antibody can be tested in small rodents to obtain meaningful toxicology profiles.

We have previously developed an LCM-based selection strategy to enrich for phage antibodies binding to tumor cells in situ residing in their tissue microenvironment as opposed to cell line artifacts (Ruan et al. (2006)*Mol. Cell Proteomics.* 5: 2364-2373). In this report we further screened the LCM selection output using our HCA-based method and identified novel macropinocytosing human antibodies targeting clinically relevant tumor antigens. Integrating LCM and HCA into phage antibody display library selection thus allows identification of novel antibodies that target true tumor antigens expressed by tumor cells residing in their tissue microenvironment and enter target cells via tumor selective pathways such as macropinocytosis. Targeted therapeutics based on these novel antibodies have the potential to improve potency in tumor killing and reduce toxicity on normal tissues, thus widening the therapeutic window and improving effectiveness of such antibody-targeted therapeutics.

Example 2

Potent Tumor Cell Killing by a Macropinocytosing Antibody-Drug Conjugate (ADC)

Figure 18:
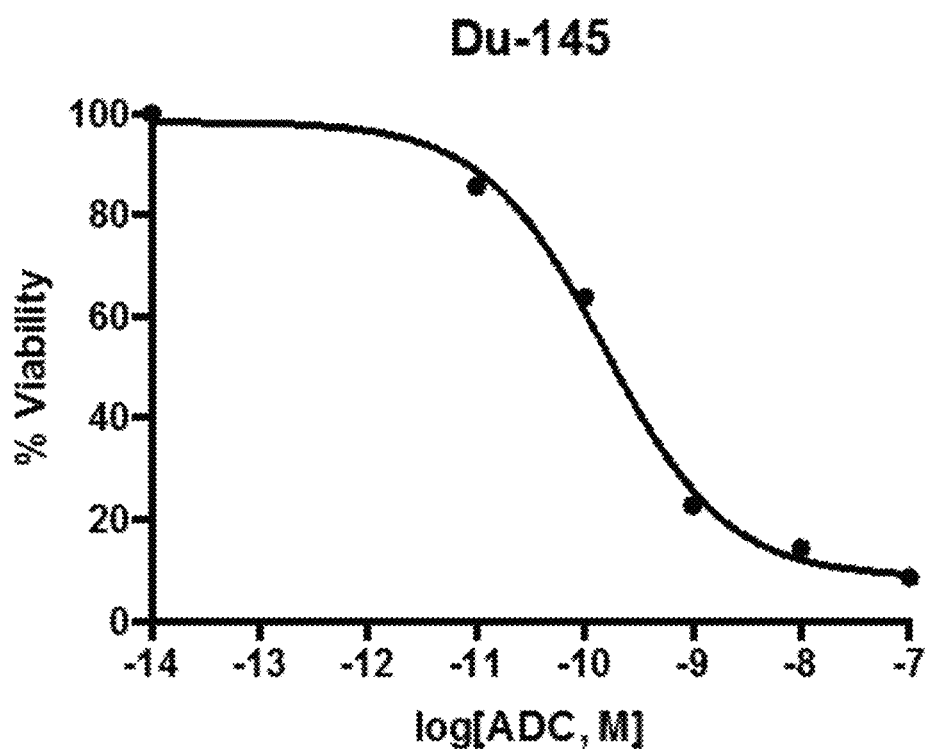
FIG. 18 illustrates potent tumor cell killing by a macropinocytosing antibody-drug conjugate (ADC).

FIG. 18 illustrates potent tumor cell killing by a macropinocytosing antibody-drug conjugate (ADC). The macropincytosing antibody HCA-F1 was conjugated to monomethyl auristatin F (MMAF) via a maleimidocaproyl-valine-citrulline-p-aminobenzyloxycarbonyl (MC-vcPAB) linker. The prostate cancer cell line Du-145 cells were seeded at 1,500 cells per well in 96-well plates, and incubated with the HCA-F1 ADC at 37° C. for 96 hours. Viability was determined using the Calcein-AM assay. EC50, estimated by curve fit using GraphPad, is 155 pM.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. An isolated antibody that is internalized into a cell via a macropinocytosis pathway, wherein said antibody comprises:
   a variable heavy (VH) domain comprising VH CDR1 consisting of the amino acid sequence SYAMH (SEQ ID NO:44) VH CDR2 consisting of the amino acid sequence VISYDGSNKYYADSVKG (SEQ ID NO:45), and VH CDR3 consisting of the amino acid sequence APAYSYGPFDY (SEQ ID NO:46) of antibody HCA-M1; and
   a variable light (VL) domain comprising VL CDR1 consisting of the amino acid sequence QGDSLRSYYAS (SEQ ID NO:51), VL CDR2 consisting of the amino acid sequence YGKNNRPS (SEQ ID NO:52), and VL CDR3 consisting of the amino acid sequence HSRDSSGTHLRV (SEQ ID NO:54) of antibody HCA-M1.

2. The antibody of claim 1, wherein said antibody is a human antibody.

3. The antibody of claim 1, wherein said antibody is internalized via a macropinocytosis pathway in a cell in which macropinocytosis is upregulated.

4. The antibody of claim 1, wherein said antibody is an antibody selected from the group consisting of an intact immunoglobulin, a Fab, a (Fab')$_2$, an scFv, and an (ScFv')$_2$.

5. The antibody of claim 1, wherein said antibody comprises the variable heavy (VH) domain of HCA-M1 (SEQ ID NO:8) and the variable light (VL) domain of HCA-M1 (SEQ ID NO:4).

6. An immunoconjugate comprising an antibody of claim 1 attached to an effector wherein said effector is selected from the group consisting of a second antibody, a detectable label, a cytotoxin or cytostatic agent, a liposome containing a drug, a radionuclide, a drug, a prodrug, a viral particle, a cytokine, a chelate, and an siRNA.

7. A pharmaceutical formulation said formulation comprising:
   a pharmaceutically acceptable excipient and a composition comprising an antibody of claim 1.

8. The immunoconjugate of claim 6, wherein said antibody is attached to an siRNA.

9. The immunoconjugate of claim 6, wherein said antibody is attached to a cytotoxin.

10. The immunoconjugate of claim 6, wherein said antibody is attached to a cytotoxic and/or cytostatic drug.

11. The immunoconjugate of claim 10, wherein said antibody is attached directly or through a linker to one or more of the following:
    said drug
    a lipid or liposome complexed with and/or containing said drug;
    a polymeric drug carrier comprising said drug; and
    a nanoparticle drug carrier comprising said drug.

12. The immunoconjugate of claim 10, wherein said drug is an anti-cancer drug.

13. The immunoconjugate of claim 10, wherein said drug is selected from the group consisting of a tubulin inhibitor, a DNA interacting agent, and a pathway or enzyme inhibitor.

14. The immunoconjugate claim 10, wherein said drug is selected from the group consisting of auristatin, 1,-(2-chloroethyl)-3-cyclohexyl-lnitrosourea, 1,3-bis(2-chloroethyl)-1-nitrosourea (BCNU), 5-fluorouracil, 5-trifluoromethyl-2'-deoxyuridine, 6-mercaptopurine, 6-thioguanine (6-TG), abraxane, abraxane, actinomycin D, anastrozole, azathioprine, belotecan, bendamustine, busulfan, camptothecin, camptothecin derivative, capecitabine, capecitabine, carboplatin, carboplatin, carmustine, chlorambucil, chloromethine, cisplatin, cladribine, colchicine, combretastatin, cyclophosphamide, cytosine Arabinoside, dacarbazine (DTIC), daunorubicin citrate, docetaxel, dolastatin, doxorubicin, epirubicin, erlotinib, etoposide, exemestane, flourouracil (5-FU), floxuridine (5-fluoro-2), fludarabine phosphate, fotemustine, gemcitabine, goserelin acetate, hexamethylmelamine, ifosfamide, imatinib mesylate, interferon, irinotecan, ixabepilone, larotaxel, letrozole, lomustine, mannosulfan, megestroltamoxifen, melphalan, methotrexate, methyl (CCNU), mitoxantrone, mTOR/PI3K inhibitor, nedaplatin, neosar, nimustine, ortataxel, oxaliplatin, paclitaxel, pamidronate disodium, pemetrexed, pentostatin, prednimustine, procarbazine HCL, raltitrexed, ranimustine, retinoic acid, a retinoic acid derivative, ribonucleotide reductase inhibitor (RNR), rubitecan, satraplatin, semustine, sorafinib, streptozocin, sunitinib, tamoxifen, taxol, temozolomide, teniposide (VM-26), tesetaxel, thiotepa, thioTEPA, topotecan, topotecan HCL, toremifene, trastuzumab, treosulfan, triaziquone, triethylene melamine, triplatin tetranitrate, trofosfamide, uramustine, vinblastine, vincristine, vindesine sulphate, vinflunine, vinorelbine tartrate, zoledronic acid, Auristatin E (AE), Monomethylauristatin E (MMAE), Auristatin F (MMAF), vcMMAE, and vcMMAF.

15. The immunoconjugate of claim 14, wherein said drug an auristatin is selected from the group consisting of Auristatin E (AE), Monomethylauristatin E (MMAE), Auristatin F (MMAF), vcMMAE, monomethyl auristatin F, and vcMMAF.

16. The immunoconjugate of claim 15, wherein said drug is monomethyl auristatin F.

17. The immunoconjugate of claim 10, wherein said drug is conjugated to said antibody via a maleimidocaproyl-valine-citrulline-p-aminobenzyloxycarbonyl (MC-vcPAB) linker.

18. The immunoconjugate of claim 6, wherein said antibody is attached to a chelate comprising a radioisotope.

19. The immunoconjugate of claim 18, wherein said antibody is attached to a chelate comprising a radioisotope selected from the group consisting of $^{99}$Tc, $^{203}$Pb, $^{67}$Ga, $^{68}$Ga $^{72}$As, $^{111}$In, $^{113}$n $^{97}$Ru, $^{62}$Cu, $^{641}$Cu, $^{52}$Fe, $^{52}$Mn, $^{5}$Cr, $^{186}$Re, $^{188}$Re, $^{77}$As, $^{90}$Y $^{67}$Cu, $^{169}$Er, $^{121}$Sn, $^{127}$Te, $^{142}$Pr, $^{143}$Pr $^{198}$Au, $^{199}$Au, $^{161}$Tb, $^{109}$Pd, $^{165}$Dy, $^{149}$Pm, $^{151}$Pm, $^{153}$Sm, $^{157}$Gd, $^{159}$Gd, $^{166}$Ho, $^{172}$Tm, $^{169}$Yb, $^{175}$Yb, $^{177}$Lu $^{105}$Rh, and $^{111}$Ag.

* * * * *